(12) United States Patent
De Vivo et al.

(10) Patent No.: US 9,630,914 B2
(45) Date of Patent: Apr. 25, 2017

(54) MULTITARGET FAAH AND COX INHIBITORS AND THERAPEUTICAL USES THEREOF

(71) Applicants: FONDAZIONE ISTITUTO ITALIANO DI TECNOLOGIA, Genoa (IT); THE REGENTS OF THE UNIVERSITY OF CALIFORNIA, Oakland, CA (US); ALMA MATER STUDIORUM—UNIVERSITA' DI BOLOGNA, Bologna (IT)

(72) Inventors: Marco De Vivo, Genoa (IT); Rita Scarpelli, Rome (IT); Andrea Cavalli, S. Lazzaro di Savena (IT); Marco Migliore, Sassari (IT); Daniele Piomelli, Irvine, CA (US); Damien Habrant, Norroy le Veneur (FR); Angelo Favia, Genoa (IT)

(73) Assignees: Fondazione Istituto Italiano Di Tecnologia, Genoa (IT); The Regents of the University of California, Oakland, CA (US); Alma Mater Studiorum—Universita' Di Bologna, Bologna (IT)

( * ) Notice: Subject to any disclaimer, the term of this patent is extended or adjusted under 35 U.S.C. 154(b) by 175 days.

(21) Appl. No.: 14/420,237

(22) PCT Filed: Aug. 1, 2013

(86) PCT No.: PCT/EP2013/066197
§ 371 (c)(1),
(2) Date: Feb. 6, 2015

(87) PCT Pub. No.: WO2014/023643
PCT Pub. Date: Feb. 13, 2014

(65) Prior Publication Data
US 2015/0203447 A1  Jul. 23, 2015

(30) Foreign Application Priority Data
Aug. 6, 2012 (WO) ............... PCT/EP2012/065336

(51) Int. Cl.
| | | |
|---|---|---|
| *A61K 31/165* | (2006.01) | |
| *C07C 271/56* | (2006.01) | |
| *C07C 271/28* | (2006.01) | |
| *C07C 271/44* | (2006.01) | |
| *C07C 271/58* | (2006.01) | |

(52) U.S. Cl.
CPC .......... *C07C 271/56* (2013.01); *C07C 271/28* (2013.01); *C07C 271/44* (2013.01); *C07C 271/58* (2013.01); *C07C 2101/02* (2013.01); *C07C 2101/04* (2013.01); *C07C 2101/08* (2013.01); *C07C 2101/14* (2013.01)

(58) Field of Classification Search
USPC ........................................ 514/304, 299, 530
See application file for complete search history.

(56) References Cited

U.S. PATENT DOCUMENTS

| | | | | |
|---|---|---|---|---|
| 7,176,201 | B2* | 2/2007 | Piomelli | ............... C07C 271/56 514/237.8 |
| 2004/0127518 | A1* | 7/2004 | Piomelli | ............... C07C 271/56 514/332 |
| 2008/0249127 | A1* | 10/2008 | Laine | ................... C07D 451/06 514/304 |

FOREIGN PATENT DOCUMENTS

WO   2006020358   2/2006

OTHER PUBLICATIONS

Alexander J P, et al. "Mechanism of Carbamate Inactivation of FAAH: Implications for the design of Covalent Inhibitors and In Vivo Functional Probes for Enzymes," Chemical & Biology vol. 12, No. 11, Nov. 1, 2005; 1179-1187.
International Search Report dated Oct. 4, 2013 corresponding to International Patent Application No. PCT/EP2013/066197; 7 pages.
Written Opinion dated Oct. 4, 2013 corresponding to International Patent Application No. PCT/EP2013/066197;7 pages.

* cited by examiner

*Primary Examiner* — Pancham Bakshi
(74) *Attorney, Agent, or Firm* — Ohlandt, Greeley, Ruggiero & Perle, LLP

(57) ABSTRACT

Multitarget inhibitors of the enzymes Fatty Acid Amide Hydrolase (FAAH), Cyclooxygenase-1 (COX-1) and/or Cyclooxygenase-2 (COX-2) having a specific carbamate moiety on the meta or ortho position of the A ring of a substituted biphenyl core and having an halogen in the ortho position of the B ring of the biphenyl core. Also concerns the therapeutical application of the multitarget inhibitors, in particular, in the prevention and treatment of cancer.

6 Claims, 2 Drawing Sheets

MULTITARGET FAAH AND COX INHIBITORS AND THERAPEUTICAL USES THEREOF

STATEMENT AS TO RIGHTS TO INVENTIONS MADE UNDER FEDERALLY SPONSORED RESEARCH AND DEVELOPMENT

This research was made, in part, with government support under NIH Grant R01 DA12413 awarded by the National Institutes of Health; the United States Government has certain rights in the invention.

CROSS-REFERENCES TO RELATED APPLICATIONS

Not applicable.

FIELD OF THE INVENTION

The invention provides novel compounds that simultaneously inhibit the enzymes Fatty Acid Amide Hydrolase (FAAH), Cyclooxygenase-1 (COX-1) and/or Cyclooxygenase-2 (COX-2), and therapeutic uses of such compounds.

The compounds of the invention find application in the medical field, in the treatment of pathological conditions in which simultaneous inhibition of FAAH, COX-1 and/or COX-2 activities is desirable.

The combined FAAH and COX-1 and/or COX-2 inhibitors are useful in the treatment of cancer and precancerous conditions and find additional applications in the treatment of inflammatory diseases, pain, eating disorders, anxiety and cardiovascular disorders.

BACKGROUND OF THE INVENTION

COX-1 and COX-2 are two enzymes that convert arachidonic acid into prostaglandin $H_2$. In mammals, different tissues express varying levels of COX-1 and COX-2. COX-1 is a constitutive enzyme found in most mammalian cells. COX-2 is an inducible enzyme expressed at low levels in most healthy tissues, but stimulated during inflammation. Both COX-1 and COX-2 are inhibited by compounds belonging to the class of non-steroidal anti-inflammatory drugs (NSAIDs), which include aspirin and indomethacin. COX-2 is selectively inhibited by the so-called coxibs, which include celecoxib and rofecoxib.

Both non-selective COX-1/COX-2 inhibitors and COX-2-selective inhibitors exert serious side effects when administered to humans. COX-1 inhibition has been correlated to peptic ulcerations, dyspepsia and kidney disease, while selective COX-2 inhibition has been correlated to increased cardiovascular risk.

FAAH is an intracellular serine hydrolase responsible for the deactivating hydrolysis of a family of naturally occurring fatty-acid ethanolamides (FAEs), which include endogenous agonists at cannabinoid receptors, such as anandamide, and at peroxisome proliferator-activated receptor-alpha (PPAR-α), such as oleoylethanolamide (OEA) and palmitoylethanolamide (PEA). Two isoforms of FAAH exist, called FAAH-1 and FAAH-2. Both isoforms are generically referred to here as FAAH. Pharmacological inhibition of FAAH activity magnifies and prolongs the biological actions of these lipid-derived messengers, offering a potential strategy to treat pathological conditions such as pain and inflammation.

Inflammatory pathologies afflict hundreds of millions of people worldwide. Yet the use of current therapies is limited by potentially serious side effects, such as gastric damage, kidney damage and increased risk of stroke.

Therefore, a need still exists for new therapeutically active compounds, which are effective in the treatment of inflammation and related conditions whose administration results in a reduced risk of side effects in humans.

One of the objects of the present invention is to provide compounds acting as combined inhibitors of FAAH, COX-1 and/or COX-2. These compounds are effective in the treatment of conditions where the regulation of these enzymes is desirable.

SUMMARY OF THE INVENTION

In accordance with a first aspect, the present invention provides a compound of Formula (I):

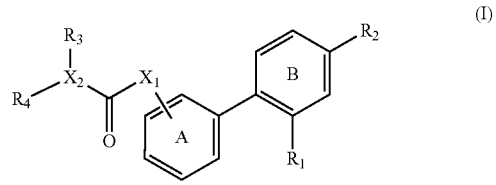

or a pharmaceutically acceptable salt thereof,
wherein
the phenyl ring A is substituted in the meta or ortho position with the group

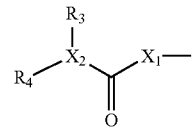

and wherein
$R_1$ is halogen,
$R_2$ is a substituted $(C_1-C_6)$alkyl, or a group —$CHR_5$—(C=O)—$R_6$
where $R_5$ is H, or an optionally substituted $(C_1-C_6)$alkyl, and $R_6$ is —OH or $NR_7R_8$,
where $R_7$ and $R_8$ are independently H, an optionally substituted group selected from $(C_1-C_{10})$alkyl, hetero$(C_1-C_{10})$alkyl, $(C_3-C_9)$cycloalkyl, hetero$(C_3-C_9)$cycloalkyl, aryl, and heteroaryl, or if taken together with the N atom to which they are attached, $R_7$ and $R_8$ form an optionally substituted N-heterocycle or an optionally substituted heteroaryl with the N atom to which they are each attached,
$X_1$ is O or $NR_9$, where $R_9$ is H or an optionally substituted alkyl,
$X_2$ is O or N,
$R_3$ and $R_4$ are independently H, an optionally substituted group selected from $(C_1-C_{10})$alkyl, hetero$(C_1-C_{10})$alkyl, $(C_3-C_9)$cycloalkyl, hetero$(C_3-C_9)$cycloalkyl, aryl and heteroaryl, or if taken together with the N atom to which they are attached when $X_2$ is N, $R_3$ and $R_4$ form an optionally substituted N-heterocycle or an optionally substituted heteroaryl with the N atom to which they are each attached,
with the proviso that
when $X_1$ is O, $X_2$ is not O,
when $X_1$ is $NR_9$, $X_2$ is not N, when $X_2$ is O, one of the groups $R_3$ or $R_4$ is absent,
when $X_1$ is $NR_9$, and $X_2$ is O, $R_3$ or $R_4$ is an optionally substituted group selected from $(C_1-C_{10})$alkyl, hetero $(C_1-C_{10})$alkyl, $(C_3-C_9)$cycloalkyl, hetero $(C_3-C_9)$ cycloalkyl, aryl, and heteroaryl,
wherein $R_9$ is H or an optionally substituted alkyl.

In a second aspect, the present invention concerns pharmaceutical compositions comprising at least one compound of Formula (I) and pharmaceutically acceptable carrier.

In a third aspect the invention concerns the use of said compound in the medical field as an inhibitor of FAAH, COX-1 and/or COX-2 in the treatment of conditions related with the modulation of such enzymes such as in the treatment of cancer or precancerous conditions, inflammatory diseases, inflammatory related conditions or pain.

In a yet further aspect, the present invention relates to a method of treatment of conditions related to the modulation of FAAH, COX-1 and/or COX-2, such as in cancer, inflammatory diseases, pain, or precancerous conditions.

The characteristics and advantages of the present invention will be evident from the following detailed description and from the working examples provided for illustrative and non-limiting purposes.

DETAILED DESCRIPTION OF THE INVENTION

Figure 1:
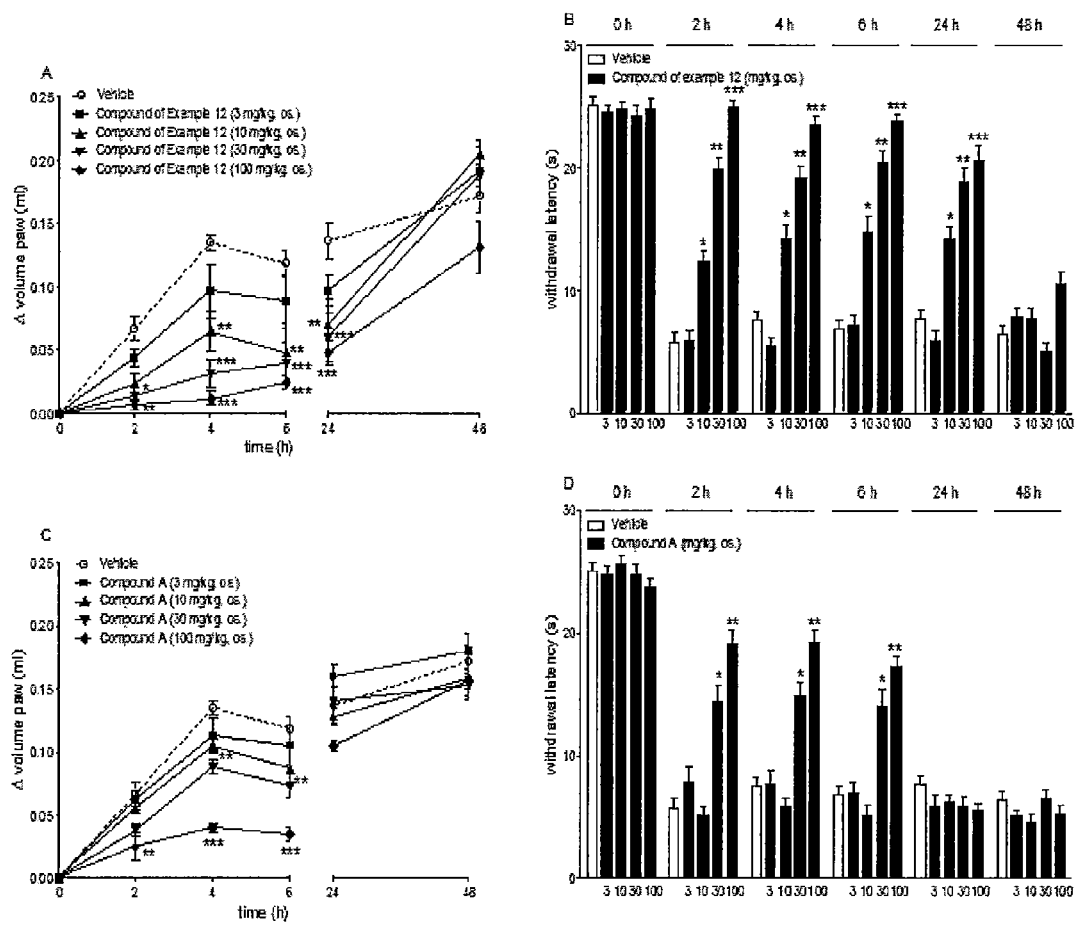
FIG. 1 shows four graphs illustrating the antinflammatory effects (graphics A and C) and antihyperalgesic effects (graphics B and D) of the compound of example 12 at different concentrations compared with the test compound A (flurbiprofen) on animal models.

In accordance with certain aspects of the present invention, the inventors have found that a selective combined or simultaneous inhibition of FAAH and COX-1 and/or COX-2 activities can be obtained by introducing a specific carbamate or reversed carbamate moiety on the meta or ortho position of the A ring of the substituted biphenyl core having an halogen in the ortho position of the B ring.

Typically, the compounds of the present invention have activity as FAAH and COX-1 or COX-2 inhibitors. In certain embodiments the compounds of the invention are active as FAAH and COX-1 and COX-2 inhibitors.

I. Compounds of Formula (I)

In accordance with a first aspect, the present invention thus provides a compound of Formula (I):

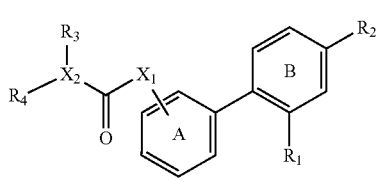

(I)

or a pharmaceutically acceptable salt thereof, wherein
the phenyl ring A is substituted in the meta or ortho position with the group

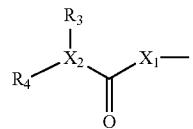

and wherein
$R_1$ is halogen,
$R_2$ is a substituted $(C_1-C_6)$ alkyl, or a group —$CHR_5$—(C=O)—$R_6$
where $R_5$ is H, or an optionally substituted $(C_1-C_6)$alkyl, and $R_6$ is —OH, or $NR_7R_8$,
where $R_7$ and $R_8$ are independently H, an optionally substituted group selected from $(C_1-C_{10})$alkyl, hetero$(C_1-C_{10})$alkyl, $(C_3-C_9)$cycloalkyl, hetero$(C_3-C_9)$cycloalkyl, aryl, and heteroaryl, or if taken together with the N atom to which they are attached, $R_7$ and $R_8$ form an optionally substituted N-heterocycle or an optionally substituted heteroaryl with the N atom to which they are each attached,
$X_1$ is O or $NR_9$, where $R_9$ is H or an optionally substituted alkyl,
$X_2$ is O or N,
$R_3$ and $R_4$ are independently H, an optionally substituted group selected from $(C_1-C_{10})$alkyl, hetero$(C_1-C_{10})$alkyl, $(C_3-C_9)$cycloalkyl, hetero$(C_3-C_9)$cycloalkyl, aryl and heteroaryl, or if taken together with the N atom to which they are attached, $R_3$ and $R_4$ form an optionally substituted N-heterocycle or an optionally substituted heteroaryl with the N atom to which they are each attached,
with the proviso that
when $X_1$ is O, $X_2$ is not O,
when $X_1$ is $NR_9$, $X_2$ is not N,
when $X_2$ is O, one of the groups $R_3$ or $R_4$ is absent,
when $X_1$ is $NR_9$, and $X_2$ is O, $R_3$ or $R_4$ is an optionally substituted group selected from $(C_1-C_{10})$alkyl, hetero $(C_1-C_{10})$alkyl, $(C_3-C_9)$cycloalkyl, hetero$(C_3-C_9)$cycloalkyl, aryl, and heteroaryl,
wherein $R_9$ is H or an optionally substituted alkyl.

In certain embodiments $R_1$ is F.
In certain embodiments $R_2$ is a $(C_1-C_6)$alkyl substituted with a group OH or COOH.
In certain embodiments $R_2$ is a group —$CHR_5$—(C=O)—$R_6$. In some of these embodiments $R_5$ is H, or an optionally substituted $(C_1-C_6)$alkyl, and $R_6$ may be OH or $NR_7R_8$ wherein $R_7$ and $R_8$ are as defined above or in the following embodiments.

In accordance with certain embodiments $R_7$ and $R_8$ independently are an optionally substituted $(C_3-C_9)$cycloalkyl $(C_0-C_4)$alkyl, wherein suitable $(C_3-C_9)$cycloalkyls include, but are not limited to, cyclopropyl, cyclobutyl, cyclopentyl, cyclohexyl, 1-cyclohexenyl, 3-cyclohexenyl, cycloheptyl, and the like.

In accordance with some embodiments $R_7$ and $R_8$ independently are an optionally substituted aryl($C_0-C_4$)alkyl wherein suitable aryl include but are not limited to, phenyl, 1-naphthyl, 2-naphthyl, 4-biphenyl, and the like.

In accordance with some embodiments $R_7$ and $R_8$ independently are an optionally substituted heteroaryl($C_0-C_4$) alkyl, wherein suitable heteroaryl include, but are not limited to, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, and the like.

In accordance with certain embodiments $R_7$ and $R_8$ independently are an optionally substituted hetero($C_3$-$C_9$)cycloalkyl($C_0$-$C_4$)alkyl wherein suitable hetero($C_3$-$C_9$)cycloalkyls include, but are not limited to, tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl) trioxane, hexahydro-1,3,5-triazine, tetrahydrothiophene, tetrahydrofuran (tetrahydrofuran-2-yl, tetrahydrofuran-3-yl), 1-(1,2,5,6-tetrahydropyridyl), pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane and the like.

In certain embodiments $R_2$ is a group —$CHR_5$—(C=O)—$R_6$, wherein $R_5$ is H, or an optionally substituted ($C_1$-$C_6$)alkyl, and $R_6$ is —OH or $NR_7R_8$, where $R_7$ and $R_8$ are as defined above and preferably are independently H, an optionally substituted group selected from ($C_1$-$C_{10}$)alkyl, hetero($C_1$-$C_{10}$)alkyl, ($C_3$-$C_9$)cycloalkyl, hetero($C_3$-$C_9$)cycloalkyl, aryl, and heteroaryl, or if taken together with the N atom to which they are attached, $R_7$ and $R_8$ form an optionally substituted N-heterocycle or an optionally substituted heteroaryl with the N atom to which they are each attached.

In accordance with certain embodiments $R_3$ and $R_4$ independently are an optionally substituted ($C_3$-$C_9$)cycloalkyl ($C_0$-$C_4$)alkyl, wherein suitable ($C_3$-$C_9$)cycloalkyls include, but are not limited to, cyclopropyl, cyclobutyl, cyclopentyl, cyclohexyl, 1-cyclohexenyl, 3-cyclohexenyl, cycloheptyl, and the like.

In accordance with certain embodiments $R_3$ and $R_4$ independently are an optionally substituted aryl($C_0$-$C_4$)alkyl, wherein a suitable aryl include, but are not limited to, phenyl, 1-naphthyl, 2-naphthyl, 4-biphenyl, and the like.

In accordance with certain embodiments $R_3$ and $R_4$ independently are an optionally substituted heteroaryl($C_0$-$C_4$) alkyl, wherein suitable heteroaryls include, but are not limited to, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, and the like.

In accordance with certain embodiments $R_3$ and $R_4$ independently are an optionally substituted hetero($C_3$-$C_9$)cycloalkyl($C_0$-$C_4$)alkyl, wherein suitable hetero($C_3$-$C_9$)cycloalkyls include, but are not limited to, tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl) trioxane, hexahydro-1,3,5-triazine, tetrahydrothiophene, tetrahydrofuran (tetrahydrofuran-2-yl, tetrahydrofuran-3-yl), 1-(1,2,5,6-tetrahydropyridyl), pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane and the like.

In accordance with certain embodiments wherein $X_1$ is $NR_9$ and $X_2$ is O, $R_3$ or $R_4$ is a substituted ($C_1$-$C_{10}$) alkyl, where $R_9$ is as defined above.

In accordance with certain embodiments wherein $X_1$ is $NR_9$ and $X_2$ is O, $R_3$ or $R_4$ are independently selected from optionally substituted ($C_3$-$C_9$) cycloalkyl($C_0$-$C_4$) alkyl, optionally substituted aryl($C_0$-$C_4$)alkyl, optionally substituted heteroaryl($C_0$-$C_4$)alkyl, optionally substituted hetero ($C_3$-$C_9$)cycloalkyl($C_0$-$C_4$)alkyl, where $R_9$ is as defined above.

In certain embodiments $R_9$ is an optionally substituted ($C_1$-$C_6$) alkyl.

In certain embodiments $R_9$ is H.

It has been surprisingly found that compounds of formula (I) are unexpectedly capable of acting as multitarget inhibitors of FAAH, COX-1 and/or COX-2, as will be shown in the working examples provided below.

Compounds of Formula (I) may contain one or more chiral centers. Compounds containing one chiral center can occur as single enantiomers or mixtures of the two enantiomers. Such mixtures occur as racemates or racemic mixtures. Compounds containing more than one chiral center can occur as single enantiomers and pairs of enantiomers, and as stereoisomers which are not enantiomers, referred to as diastereoisomers. Compounds of Formula (I), are meant to encompass all possible stereoisomers/enantiomers and mixtures thereof.

Some of the compounds described herein may exist with different points of attachment of a hydrogen atom, referred to as tautomers. Such an example may be a ketone and its enol form known as keto-enol tautomers. The individual tautomers as well as mixture thereof are encompassed by the Formula (I).

The compounds of Formula (I) may have unnatural ratios of atomic isotopes at one or more of their atoms. For example, the compounds may be radiolabeled with isotopes such as tritium or carbon-14. All isotopic variations of the compounds of the present invention, whether radioactive or not, are within the scope of the present invention Compounds of Formula (I) may be isolated in the form of their pharmaceutically acceptable salts. Preferably, when the compound of Formula (I) is in the form of a pharmaceutically acceptable salt, said salt is hydrochloride, hydrobromide, sulfate, phosphate, methane sulfonate, ethane sulfonate, acetate, malate, tartrate, citrate, lactate, oxalate, succinate, fumarate, maleate, benzoate, salicylate, phenylacetate, or mandelate and the like. Alternatively, said salt is a salt of a metal selected from the IA or IIA groups of the periodic table of elements.

The present invention also encompasses active metabolites of compounds of Formula (I).

II. Subset of Compounds of Formula (IA)

In accordance with certain aspects of the present invention, the inventors have found that the compounds of Formula (I) having a carbamoyl moiety wherein $X_1$ is O and $X_2$ is N, show an effective multitarget inhibitory activity on FAAH and COX-1 and/or COX-2.

In accordance with certain embodiments of the invention, a subset of compounds as defined in Formula (I) wherein $X_1$ is O and $X_2$ is N are provided, having the Formula (Ia)

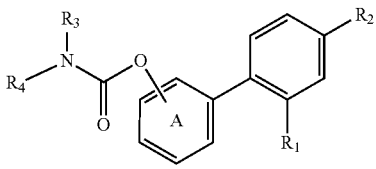

(Ia)

or pharmaceutically acceptable salts thereof,
wherein
the phenyl ring A is substituted in the meta or ortho position with the carbamoyl group, $R_1$ is halogen, $R_2$ is a substituted $(C_1-C_6)$alkyl, or a group —$CHR_5$—(C=O)—$R_6$ where $R_5$ is H, or an optionally substituted $(C_1-C_6)$alkyl, and $R_6$ is —OH, or $NR_7R_8$, where $R_7$ and $R_8$ are independently H, an optionally substituted group selected from $(C_1-C_{10})$alkyl, hetero$(C_1-C_{10})$alkyl, $(C_3-C_9)$cycloalkyl, hetero$(C_3-C_9)$cycloalkyl, aryl, and heteroaryl, or, if taken together with the N atom to which they are attached, $R_7$ and $R_8$ form an optionally substituted N-heterocycle or an optionally substituted heteroaryl with the N atom to which they are each attached, $R_3$ and $R_4$ are independently H, an optionally substituted group selected from $(C_1-C_{10})$alkyl, hetero$(C_1-C_{10})$alkyl, $(C_3-C_9)$cycloalkyl, hetero$(C_3-C_9)$cycloalkyl, aryl, and heteroaryl, or if taken together with the N atom to which they are attached, $R_3$ and $R_4$ form an optionally substituted N-heterocycle or an optionally substituted heteroaryl with the N atom to which they are each attached.

In certain embodiments $R_1$ is F.

In certain embodiments $R_2$ is a $(C_1-C_6)$alkyl substituted with a group OH or COOH.

In certain embodiments $R_2$ is a group —$CHR_5$—(C=O)—$R_6$. In some of these embodiments $R_5$ is H, or an optionally substituted $(C_1-C_6)$alkyl, and $R_6$ may be OH or $NR_7R_8$ wherein $R_7$ and $R_8$ are as herein defined.

In accordance with certain embodiments $R_5$ is H.

In certain embodiments $R_5$ is an optionally substituted $(C_1-C_6)$alkyl. In certain embodiments $R_5$ is $CH_3$.

In certain embodiments $R_6$ is OH.

In certain embodiments $R_1$ is F, $R_2$ is —$CHR_5$—(C=O)—$R_6$ wherein $R_5$ is H or a linear or branched $(C_1-C_6)$alkyl, typically $CH_3$, and $R_6$ is OH. In these embodiments, $R_3$ and $R_4$ may be a group or radical as defined in the present description or claims.

In certain embodiments $R_2$ is —$CHR_5$—(C=O)—$R_6$ wherein $R_5$ is $CH_3$, $R_6$ is OH.

In certain embodiments $R_1$ is F, $R_2$ is —$CHR_5$—(C=O)—$R_6$ wherein $R_5$ is $CH_3$, $R_6$ is OH, $R_3$ is H, $R_4$ is $(C_1-C_{10})$alkyl, $(C_3-C_9)$cycloalkyl$(C_0-C_4)$alkyl, or aryl$(C_0-C_4)$alkyl, for example phenyl$(C_0-C_4)$alkyl.

In accordance with certain embodiments $R_6$ is $NR_7R_8$ wherein $R_7$ and $R_8$ are as defined above or, independently, in each of the following embodiments.

In accordance with certain embodiments $R_7$ and $R_8$ independently are an optionally substituted $(C_3-C_9)$cycloalkyl $(C_0-C_4)$alkyl, wherein suitable $(C_3-C_9)$ cycloalkyls include, but are not limited to, cyclopropyl, cyclobutyl, cyclopentyl, cyclohexyl, 1-cyclohexenyl, 3-cyclohexenyl, cycloheptyl, and the like.

In accordance with some embodiments $R_7$ and $R_8$ independently are an optionally substituted aryl-$C_0-C_4$alkyl wherein suitable aryl include but are not limited to phenyl, 1-naphthyl, 2-naphthyl, 4-biphenyl, and the like.

In accordance with some embodiments $R_7$ and $R_8$ independently are an optionally substituted heteroaryl$(C_0-C_4)$ alkyl, wherein suitable heteroaryl include, but are not limited to, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, and the like.

In accordance with certain embodiments $R_7$ and $R_8$ independently are an optionally substituted hetero$(C_3-C_9)$cycloalkyl$(C_0-C_4)$alkyl wherein suitable heteroC$_3$-C$_9$(cycloalkyl) include, but are not limited to, tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl) trioxane, hexahydro-1,3,5-triazine, tetrahydrothiophene, tetrahydrofuran (tetrahydrofuran-2-yl, tetrahydrofuran-3-yl), 1-(1,2,5,6-tetrahydropyridyl), pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane and the like.

In accordance with certain embodiments $R_3$ and $R_4$ independently are an optionally substituted $(C_3-C_9)$cycloalkyl $(C_0-C_4)$alkyl, wherein suitable $(C_3-C_9)$ cycloalkyls include, but are not limited to cyclopropyl, cyclobutyl, cyclopentyl, cyclohexyl, 1-cyclohexenyl, 3-cyclohexenyl, cycloheptyl, and the like. In accordance with certain embodiments $R_3$ and $R_4$ independently are an optionally substituted aryl$(C_0-C_4)$ alkyl, wherein a suitable aryl include, but are not limited to, phenyl, 1-naphthyl, 2-naphthyl, 4-biphenyl, and the like.

In accordance with certain embodiments $R_3$ and $R_4$ independently are an optionally substituted heteroaryl$(C_0-C_4)$ alkyl, wherein suitable heteroaryl include, but are not limited to, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, and the like.

In accordance with certain embodiments $R_3$ and $R_4$ independently are an optionally substituted hetero$(C_3-C_9)$cycloalkyl$(C_0-C_4)$ alkyl, wherein suitable hetero$(C_3-C_9)$cycloalkyl include, but are not limited to, tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl) trioxane, hexahydro-1,3,5-triazine, tetrahydrothiophene, tetrahydrofuran (tetrahydrofuran-2-yl, tetrahydrofuran-3-yl), 1-(1,2,5,6-tetrahydropyridyl), pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane and the like.

In accordance with some embodiments $R_9$ is H.

In certain embodiments $R_9$ is an optionally substituted $(C_1-C_6)$alkyl.

In certain embodiments the phenyl ring A is substituted in one of the meta positions with the carbamoyl group.

In certain embodiments the phenyl ring A is substituted in one of the ortho positions with the carbamoyl group.

In certain aspects, compounds of Formula (Ia) are provided where the substituents groups $R_1$, $R_2$, $R_3$, $R_4$, $R_5$, $R_6$, $R_7$, $R_8$ are combinations of the above embodiments.

III. Subset of Compounds of Formula (Ib)

In accordance with certain aspects of the invention, the inventors have found that the compounds of Formula (I) having a reverse-carbamoyl moiety wherein $X_1$ is $NR_9$ and $X_2$ is O, also show an effective multitarget inhibitory activity on FAAH and at least one COX enzyme.

In accordance with certain embodiments of the invention, a subset of compounds as defined in Formula (I) wherein $X_1$ is $NR_9$ and $X_2$ is O are provided, having the formula (Ib)

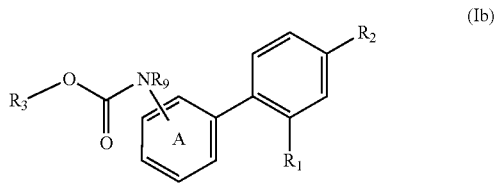

(Ib)

or pharmaceutically acceptable salts thereof,
wherein
the phenyl ring A is substituted in the meta or ortho position with the reverse-carbamoyl group,
$R_1$ is halogen,
$R_2$ is a substituted $(C_1-C_6)$alkyl, or a group —$CHR_5$—(C=O)—$R_6$
where $R_5$ is H, or an optionally substituted $(C_1-C_6)$alkyl, and $R_6$ is —OH or $NR_7R_8$,
where $R_7$ and $R_8$ are independently H, an optionally substituted group selected from $(C_1-C_{10})$alkyl, hetero$(C_1-C_{10})$alkyl, $(C_3-C_9)$cycloalkyl, hetero$(C_3-C_9)$cycloalkyl, aryl, and heteroaryl, or if taken together with the N atom to which they are attached, $R_7$ and $R_8$ form an optionally substituted N-heterocycle or an optionally substituted heteroaryl with the N atom to which they are each attached,
$R_3$ is an optionally substituted group selected from $(C_1-C10)$alkyl, hetero$(C_1-C_{10})$alkyl, $(C_3-C_9)$cycloalkyl, hetero$(C_3-C_9)$cycloalkyl, aryl and heteroaryl,
$R_9$ is H or an optionally substituted alkyl.

In certain embodiments $R_1$ is F.

In certain embodiments $R_2$ is a $(C_1-C_6)$alkyl substituted with a group OH or COOH.

In certain embodiments $R_2$ is a group —$CHR_5$—(C=O)—$R_6$. In some of these embodiments $R_5$ is H, or an optionally substituted $(C_1-C_6)$alkyl, and $R_6$ may be OH or $NR_7R_8$ wherein $R_7$ and $R_8$ are as herein defined.

In accordance with certain embodiments $R_5$ is H.

In certain embodiments $R_5$ is an optionally substituted $(C_1-C_6)$alkyl. In certain embodiments $R_5$ is $CH_3$.

In certain embodiments $R_6$ is OH.

In certain embodiments $R_2$ is —$CHR_5$—(C=O)—$R_6$ wherein $R_5$ is $CH_3$, $R_6$ is OH.

In certain embodiments $R_1$ is F, $R_2$ is —$CHR_5$—(C=O)—$R_6$ wherein $R_5$ is $CH_3$, $R_6$ is OH, $R_3$ is $(C_1-C_{10})$alkyl, $(C_3-C_9)$cycloalkyl$(C_0-C_4)$ alkyl, or aryl$(C_0-C_4)$alkyl, for example phenyl$(C_0-C_4)$alkyl.

In accordance with certain embodiments $R_7$ and $R_8$ independently are an optionally substituted $(C_3-C_9)$cycloalkyl $(C_0-C_4)$alkyl, wherein suitable $(C_3-C_9)$cycloalkyls include, but are not limited to, cyclopropyl, cyclobutyl, cyclopentyl, cyclohexyl, 1-cyclohexenyl, 3-cyclohexenyl, cycloheptyl, and the like.

In accordance with some embodiments $R_7$ and $R_8$ independently are an optionally substituted aryl $(C_0-C_4)$alkyl wherein suitable aryl include but are not limited to phenyl, 1-naphthyl, 2-naphthyl, 4-biphenyl, and the like.

In accordance with some embodiments $R_7$ and $R_8$ independently are an optionally substituted heteroaryl-$(C_0-C_4)$alkyl, wherein suitable heteroaryl include but are not limited to 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, and the like.

In accordance with certain embodiments $R_7$ and $R_8$ independently are an optionally substituted hetero$(C_3-C_9)$cycloalkyl$(C_0-C_4)$alkyl wherein suitable hetero$(C_3-C_9)$cycloalkyl include, but are not limited to, tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl) trioxane, hexahydro-1,3,5-triazine, tetrahydrothiophene, tetrahydrofuran (tetrahydrofuran-2-yl, tetrahydrofuran-3-yl), 1-(1,2,5,6-tetrahydropyridyl), pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane and the like.

In accordance with certain embodiments $R_3$ is an optionally substituted $(C_3-C_9)$cycloalkyl$(C_0-C_4)$alkyl, wherein suitable $(C_3-C_9)$cycloalkyls include but are not limited to cyclopropyl, cyclobutyl, cyclopentyl, cyclohexyl, 1-cyclohexenyl, 3-cyclohexenyl, cycloheptyl, and the like.

In accordance with certain embodiments $R_3$ is an optionally substituted aryl $(C_0-C_4)$alkyl, wherein a suitable aryl include, but are not limited to, phenyl, 1-naphthyl, 2-naphthyl, 4-biphenyl, and the like. In accordance with certain embodiments $R_3$ is an optionally substituted heteroaryl$(C_0-C_4)$alkyl, wherein suitable heteroaryl include, but are not limited to, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl, and the like.

In accordance with certain embodiments $R_3$ is an optionally substituted hetero$(C_3-C_9)$cycloalkyl$(C_0-C_4)$alkyl, wherein suitable hetero$(C_3-C_9)$cycloalkyl include, but are not limited to, tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl) trioxane, hexahydro-1,3,5-triazine, tetrahydrothiophene, tetrahydrofuran (tetrahydrofuran-2-yl, tetrahydrofuran-3-yl), 1-(1,2,5,6-tetrahydropyridyl), pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane and the like.

In accordance with certain embodiments $R_3$ is an optionally substituted ($C_1$-$C_{10}$ alkyl, hetero($C_1$-$C_{10}$)alkyl, ($C_3$-$C_9$) cycloalkyl, hetero ($C_3$-$C_9$)cycloalkyl, aryl or heteroaryl.

In accordance with some embodiments $R_9$ is H.

In accordance with some embodiments $R_9$ is ($C_1$-$C_6$) alkyl.

In certain embodiments the phenyl ring A is substituted in one of the meta positions with the reverse-carbamoyl group.

In certain embodiments the phenyl ring A is substituted in one of the ortho positions with the reverse-carbamoyl group.

In certain aspects, compounds of Formula (Ib) are provided where the substituents groups $R_1$, $R_2$, $R_3$, are combinations of the above embodiments.

According to additional aspects, the present invention provides embodiments of the compounds of Formula (I), (Ia) or (Ib) as defined in the appended claims.

IV. Definitions

All technical and scientific terms used herein have the same meaning as commonly understood by a person of ordinary skill in the art to which the claimed subject matter belongs, unless otherwise defined.

The following terms, used in the specification and claims of this application, have the meaning specified hereunder, unless otherwise defined.

The term "halogen" or "halo", as used herein, indicates fluorine (F), chlorine (Cl), bromine (Br) or iodine (I).

The term "alkyl", as used herein, by itself or as part of another substituent, indicates aliphatic hydrocarbon groups, including straight (unbranched) chains or branched chains, having 1 to 12 carbon atoms which may be fully saturated, mono- or polyunsaturated. The term "lower alkyl", as used herein, refers to straight chains or branched chains, having 1 to 6 carbon atoms.

By way of an example, saturated alkyls include, but are not limited to, groups such as methyl, ethyl, n-propyl, isopropyl, n-butyl, tert-butyl, isobutyl, sec-butyl, n-pentyl, n-hexyl, n-heptyl, n-octyl, and the like.

Alkyl groups according to the present invention may be unsubstituted or substituted by one or more substituents.

The alkyl group of the compounds described herein may be designated as "($C_1$-$C_{10}$)alkyl, ($C_1$-$C_6$)alkyl or ($C_0$-$C_4$) alkyl" or similar designations. By way of example only, "($C_1$-$C_{10}$) alkyl" indicates that there are from 1 to 10 carbon atoms in the alkyl chain, i.e., the alkyl chain, if present, is selected from among methyl, ethyl, propyl, iso-propyl, n-butyl, iso-butyl, sec-butyl, and tert-butyl, isobutyl, sec-butyl, n-pentyl, n-hexyl, n-heptyl, n-octyl, and the like.

Terms such as "haloalkyl," are meant to include monohaloalkyl and polyhaloalkyl. For example, the term "halo ($C_1$-$C_4$)alkyl" is mean to include, but not be limited to, trifluoromethyl, 2,2,2-trifluoroethyl, 4-chlorobutyl, 3-bromopropyl, and the like.

Alkyl groups according to the present invention may be saturated or unsaturated aliphatic hydrocarbon groups.

The term "unsaturated" aliphatic hydrocarbon group encompasses alkenyl and alkynyl. The term "alkenyl" indicates an alkyl group, as defined herein, comprising at least two carbon atoms and containing at least one carbon-carbon double bond. In certain embodiments, alkenyl refers to alkyl radicals of 2 to 6 carbon atoms and containing at least one carbon-carbon double bond. Examples include, but are not limited to, ethenyl, 1-propenyl, 2-propenyl, 1- or 2-butenyl, and the like. Alkenyl groups according to the present invention may be unsubstituted or substituted by one or more substituents.

The term "alkynyl" indicates an alkyl group, as defined herein, consisting of at least two carbon atoms and containing at least one carbon-carbon triple bond. In certain embodiments, alkynyl refers to alkyl radicals of 2 to 6 carbon atoms and containing at least one carbon-carbon triple bond. Representative examples include, but are not limited to, ethynyl, 1-propynyl, 2-propynyl, 1- or 2-butynyl, and the like. Alkynyl groups according to the present invention may be unsubstituted or substituted by one or more substituents.

The term "alkyl," unless otherwise noted, is also meant to include those derivatives of alkyl defined in more detail below, such as "heteroalkyl."

In general, the terms "cycloalkyl" and "heterocycloalkyl", by themselves or in combination with other terms, represent, unless otherwise stated, cyclic versions of "alkyl" and "heteroalkyl", respectively.

Specifically, "cycloalkyl" refers to a saturated carbocyclic group of from 3 to 9 carbon atoms having a single ring. Examples of cycloalkyl include, but are not limited to, cyclopentyl, cyclohexyl, 1-cyclohexenyl, 3-cyclohexenyl, cycloheptyl, and the like.

Cycloalkyl groups according to the present invention may be unsubstituted or substituted by one or more substituents.

Cycloalkyl groups according to the present invention may be saturated or unsaturated carbocyclic groups. The term unsaturated carbocyclic group encompasses cycloalkenyl and cycloalkynyl.

The term "cycloalkenyl", as used herein, refers to an unsaturated carbocyclic group of from 4 to 9 carbon atoms having a single ring and containing at least one carbon-carbon double bond but not having a completely conjugated pi-electron system. Non-limiting examples of cycloalkenyl are, for example, cyclopentenyl, cyclohexenyl, cyclohexadienyl. Cycloalkenyl groups according to the present invention may be unsubstituted or substituted by one or more substituents.

The term "cycloalkynyl", as used herein, refers to an unsaturated carbocyclic group of from 6 to 9 carbon atoms having a single ring and containing at least one carbon-carbon triple bond. Non-limiting examples of cycloalkynyl are, for example, cyclohexynyl, cycloheptynyl. cycloalkynyl groups according to the present invention may be unsubstituted or substituted by one or more substituents.

As used herein, the term 'heteroatom' refers to an atom other than carbon or hydrogen. Heteroatom typically is meant to include oxygen (O), nitrogen (N), and sulphur (S).

Specifically, the term "heteroalkyl", by itself or in combination with another term, means, unless otherwise stated, a stable straight or branched chain, or cyclic hydrocarbon radical, or combinations thereof, consisting of the stated number of carbon atoms and at least one heteroatom typically selected from the group consisting of O, N, and S, in particular wherein the nitrogen and sulfur atoms may optionally be oxidized and the nitrogen heteroatom may optionally be quaternized. The heteroatom(s) O, N and S may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$— N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—

CH$_3$, —CH=CH—O—CH$_3$, —Si(CH$_3$)$_3$, —CH$_2$—CH=NOCH$_3$, and —CH=CH—N(CH$_3$)—CH$_3$. Up to two heteroatoms may be consecutive, such as, for example, —CH$_2$—NH—OCH$_3$ and —CH$_2$—O—Si(CH$_3$)$_3$. Similarly, the term "heteroalkylene" by itself or as part of another substituent means a divalent radical derived from heteroalkyl, as exemplified, but not limited by, —CH$_2$—CH$_2$—S—CH$_2$—CH$_2$— and —CH$_2$—S—CH$_2$—CH$_2$—NHCH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the Formula of the linking group is written. For example, the Formula —C(O)$_2$R'— represents both —C(O)$_2$R'— and —R'C(O)$_2$—.

The term "heterocycloalkyl" group, ("non-aromatic heterocycle" group), refers to a cycloalkyl group (non aromatic group) that includes at least one heteroatom selected from nitrogen, oxygen and sulfur. The radicals may be fused with an aryl or heteroaryl. Heterocycloalkyl rings can be formed by three, four, five, six, seven, eight, nine atoms. Heterocycloalkyl groups can be optionally substituted.

Examples of heterocycloalkyls include, but are not limited to, lactams, lactones, cyclic imides, cyclic thioimides, cyclic carbamates, 1-(1,2,5,6-tetrahydropyridyl), tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl) trioxane, hexahydro-1,3,5-triazine, tetrahydrothiophene, tetrahydrofuran (tetra hydrofuran-2-yl, tetrahydrofuran-3-yl), pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "aryl" (Ar) means, unless otherwise stated, a polyunsaturated, cyclic aromatic hydrocarbon ring which can be a single ring or multiple rings (preferably from 1 to 3 rings) which are fused together and at least one of the carbocyclic ring is aromatic. By way of an example, aryl groups include phenyl, 1-naphthyl, 2-naphthyl, 9,10-dihydroanthracenyl, indanyl, fluorenyl and the like. Aryl groups according to the present invention may be unsubstituted or substituted by one or more substituents.

The term "heteroaryl" or alternatively, "heteroaromatic" refers to an aryl as defined above wherein one to four carbon atoms are independently replaced by heteroatoms selected from N, O, and S, wherein the nitrogen and sulfur atoms are optionally oxidized, and the nitrogen atom(s) are optionally quaternized. A heteroaryl group may be attached to the remainder of the molecule through a heteroatom.

Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

Heteroaryl groups according to the present invention may be unsubstituted or substituted by one or more substituents.

The term "aromatic ring", as used herein, refers to a moiety wherein the constituent carbon atoms make up an unsaturated ring system, all atoms in the ring system are sp$^2$ hybridized and the total number of pi electrons is equal to 4n+2, wherein n is an integer.

The term "heteroaromatic ring", as used herein, refers to an "aromatic ring" as defined above wherein one or more carbon atoms are independently replaced by heteroatoms chosen from the group consisting of nitrogen, oxygen and sulfur.

The term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like).

Each of the above terms (e.g., "alkyl" including "heteroalkyl", "aryl" and "heteroaryl") are meant to include both substituted and unsubstituted forms of the indicated radical. Preferred substituents for each type of radical are provided below.

Unless otherwise indicated, the term "substituted", as used herein, means that one or more hydrogen atoms of the above mentioned groups are replaced with another non-hydrogen atom or functional group, provided that normal valencies are maintained and that the substitution results in a stable compound.

Substituents for the alkyl and heteroalkyl radicals, including those groups often referred to as alkylene, alkenyl, heteroalkylene, heteroalkenyl, alkynyl, cycloalkyl, heterocycloalkyl, cycloalkenyl, heterocycloalkenyl, and cycloalkynyl, may be one or more of a variety of groups selected from, but not limited to: R', OH, —OR', =O, =NR', =N—OR', —NR'R", —SR', -halogen, —OC(O)R', —C(O)R', —CO$_2$R', —CONR'R", —OC(O)NR'R", —NR"C(O)R', —NR'—C(O)NR"R"', —NR"C(O)$_2$R', —NR—C(NR'R"R"') =NR"", —NRC(NR'R"), =NR"', —S(O)R', —S(O)$_2$R', —S(O)$_2$NR'R", —NRSO$_2$R', —CN and —NO$_2$.

R', R", R"' and R"" each preferably independently refer to hydrogen, substituted or unsubstituted alkyl, preferably C$_1$-C$_6$ alkyl, substituted or unsubstituted heteroalkyl, unsubstituted or substituted aryl, alkoxy, thioalkoxy groups, or aryl alkyl groups.

When a compound of the invention includes more than one R group, for example, each of the R groups is independently selected as are each R', R", R"' and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$), haloalkoxy (e.g., —OCF$_3$ and OCHF$_2$) and acyl (e.g., —C(O)CH$_3$, —C(O)CF$_3$, —C(O)CH$_2$OCH$_3$, and the like).

In certain embodiments the term "substituted alkyl" comprises alkyl groups as defined hereinabove in which one or more atoms or functional groups of the alkyl moiety are replaced with another atom or functional group including, by way of example, alkyl, halogen, aryl, substituted aryl, hydroxyl, alkoxy, amino, alkoxyl, alkylamino, sulfate.

In certain embodiments alkyl is substituted (i.e. a "substituted alkyl" for example a "substituted (C$_1$-C$_6$)alkyl") by one or more substituents independently selected from the group comprising hydroxy, alkoxy, amino, monoalkylamino, dialkylamino or carboxylic.

In certain embodiments the term "substituted ($C_1$-$C_6$) alkyl" means a ($C_1$-$C_6$)alkyl moiety/group substituted with OH, COOH, CN, SH, F, $NH_2$, NHR' or NR'R" wherein R', R" are as defined above; the groups OH, COOH, being preferred.

Similar to the substituents described for the alkyl radical, substituents for the aryl and heteroaryl groups are varied and are selected from, for example: halogen, —OR', =O, =NR', =N—OR', NR'R", —SR', —OC(O)R', —C(O)R', —$CO_2$R', —CONR'R", —OC(O)NR'R", —NR"C(O)R', —NR'—C(O)NR"R'", —NR"C(O)$_2$R', —NR—C(NR'R"R'")=NR"", —NRC(NR'R")=NR'", —S(O)R', —S(O)$_2$R', —S(O)$_2$NR'R", —NRSO$_2$R', —CN and —NO$_2$, —R', —N$_3$, CH(Ph)$_2$, fluoro($C_1$-$C_4$)alkoxy, and fluoro($C_1$-$C_4$)alkyl, in a number ranging from zero to the total number of hydrogen atoms on the aromatic ring system; and where R', R", R'" and R"" are preferably independently selected from hydrogen, ($C_1$-$C_8$)alkyl and heteroalkyl, unsubstituted aryl and heteroaryl, (unsubstituted aryl) ($C_1$-$C_4$)alkyl, and (unsubstituted aryl)oxy ($C_1$-$C_4$)alkyl. When a compound of the invention includes more than one R group, for example, each of the R groups is independently selected as are each R', R", R'" and R"" groups when more than one of these groups is present.

An "alkoxy" group refers to a (alkyl)O-group wherein alkyl is as defined above.

In general, the term "optionally substituted" or "substituted" means that the referenced group may be substituted with one or more additional group(s) individually and independently selected specifically from alkyl, cycloalkyl, aryl, heteroaryl, heteroalicyclic, hydroxy, alkoxy, aryloxy, mercapto, alkylthio, arylthio, alkylsulfoxide, arylsulfoxide, alkylsulfone, arylsulfone, cyano, halo, carbonyl, thiocarbonyl, isocyanato, thiocyanato, isothiocyanato, nitro, perhaloalkyl, perfluoroalkyl, silyl, and amino, including mono- and di-substituted amino groups, and the protected derivatives thereof.

Where substituent groups are specified by their conventional chemical formulae, written from left to right, they equally encompass the chemically identical substituents which would result from writing the structure from right to left, e.g., —OCH$_2$— is intended to also —CH$_2$O—.

The term "heterocycle" refers to heteroaromatic and heteroalicyclic groups containing one to four heteroatoms each selected from O, S and N, wherein each heterocyclic group has from 3 to 9 atoms in its ring system, and with the proviso that the ring of the group does not contain two adjacent O or S atoms.

Specifically, the term "N-heterocycle" refers to heterocyclic groups containing one to four N atoms wherein each heterocyclic group has from 3 to 9 atoms in its ring system.

Herein, whenever the number of carbon atoms in a heterocycle is indicated (for example hetero($C_3$-$C_9$)cycloalkyl, at least one other atom (the heteroatom) must be present in the ring. Designations such as "hetero($C_3$-$C_9$) cycloalkyl" refer only to the number of carbon atoms in the ring and do not refer to the total number of atoms in the ring. It is understood that the heterocyclic ring can have additional heteroatoms in the ring. Designations such as "4-6 membered heterocycle" refer to the total number of atoms that are contained in the ring (i.e., a four, five, or six membered ring, in which at least one atom is a carbon atom, at least one atom is a heteroatom and the remaining two to four atoms are either carbon atoms or heteroatoms). In heterocycles that have two or more heteroatoms, those two or more heteroatoms can be the same or different from one another. Heterocycles can be optionally substituted. The heterocyclic groups include benzo-fused ring systems. An example of a 4-membered heterocyclic group is azetidinyl (derived from azetidine). An example of a 5-membered heterocyclic group is thiazolyl. An example of a 6-membered heterocyclic group is pyridyl, and an example of a 10-membered heterocyclic group is quinolinyl.

Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, 5 dihydrofuranyl, pyrazolidinyl, imidazolinyl, imidazolidinyl, 3-azabicyclo[3.1.0]hexanyl, 3-azabicyclo[4.1-0]heptanyl, 3H-indolyl and quinolizinyl.

Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, 0 benzofurazanyl, benzothiophenyl, benzothiazolyl, benzoxazolyl, quinazolinyl, quinoxalinyl, naphthyridinyl, and furopyridinyl.

The foregoing groups, as derived from the groups listed above, may be C-attached or N-attached where such is possible. For instance, a group derived from pyrrole may be pyrrol-1-yl (N-attached) or pyrrol-3-yl (C attached). Further, a group derived from imidazole may be imidazol-1-yl or imidazol-3-yl (both N-attached) or imidazol-2-yl, imidazol-4-yl or imidazol-5-yl (all C-attached).

The heterocyclic groups include benzo-fused ring systems and ring systems substituted with one or two oxo (=O) moieties such as pyrrolidin-2-one. Depending on the structure, a heterocycle group can be a monoradical or a diradical (i.e., a heterocyclene group).

V. Pharmaceutically Acceptable Salts

It will be understood that, as used herein, references to the compounds of Formula (I) (Ia) or (Ib) are meant to include also the pharmaceutically acceptable salts or derivatives thereof.

Furthermore, the compound of the formula (I) (Ia), (Ib) may form an acid addition salt or a salt with a base, depending on the kind of the substituents, and these salts are included in the present invention, as long as they are pharmaceutically acceptable salts.

Derivatives of the compounds of the formula (I) (Ia), (Ib) may be pharmaceutically acceptable amides of amino acids such as glycine, L-phenylalanine, L-tryphtophan, L-valine, L-isoleucine, L-alanine, L-leucine, L-glutamic acid, L-aspartic acid and β-alanine (Ashutosh Mishra et al., *J. Braz. Chem. Soc.,* 2008, 19 (1), 89-100). Derivatives of the compounds of the formula (I) (Ia), (Ib) may also be pharmaceutically acceptable esters such as ethyl, methyl, isopropyl, glycerides (Yoshiharu Deguchi et al., *Journal of Drug Targeting,* 2000, 8(6), 371-381), glycosides (Qian Chen et al., *Journal of Drug Targeting,* 2009, 17(4), 318-328) and derivatives of amino acids such as L-tyrosine or L-lysine (Mikko Gynther et al., *J. Med. Chem.,* 2008, 51, 932-936; Mikko Gynther et al., *International J. Pharm.,* 2010, 399(1-2), 121-128).

The terms "the compound of the invention" and "the compounds of the present invention" and "the compounds of Formula (I)" refer to each of the compounds of Formulae (I), (Ia) or (Ib) and are meant to include their pharmaceutically acceptable salts, hydrates, solvates, and crystalline forms and also any suitable forms as illustrated hereinafter.

As used herein, the term "salt" refers to any salt of a compound according to the present invention prepared from an inorganic or organic acid or base and internally formed salts. Typically, such salts have a physiologically acceptable anion or cation.

Suitably physiologically or pharmaceutically acceptable salts of the compounds of the present invention include the hydrochloride, acetate, hydrobromide, sulfate, phosphate, methane or ethane sulfonate, acetate, citrate, gluconate, lactate, tartrate, phosphate, borate, maleate, oxalate, succinate, fumarate benzoate, salicylate, phenylacetate, or mandelate, sulphate and nitrate, the hydrochloride being preferred.

Alternatively, the salt may be a salt of a metal which typically is selected from the IA or IIA groups of the periodic table of elements.

The salts of compounds of Formula (I), (Ia), (Ib), may be prepared by reacting a basic compound with the desired acid in solution.

Physiologically or pharmaceutically acceptable salts are particularly suitable for medical applications because of their greater aqueous solubility relative to the parent compounds.

Pharmaceutical acceptable salts may also be prepared from other salts, including other pharmaceutically acceptable salts, of the compounds of Formula (I), (Ia), (Ib), using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of Formula I may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. For example, pharmaceutically acceptable prodrugs are described in T. Higuchi and V. Stella, *Prodrugs as Novel Delivery Systems*, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "*Improved oral drug delivery: solubility limitations overcome by the use of prodrugs*", Advanced Drug Delivery Reviews (1996) 19(2) 115-130, and in Jarkko Rautio e al., "*Prodrugs: design and clinical applications*", Nature Review Drug Discovery, (2008) 7, 255-270 each of which are incorporated herein by reference.

Prodrugs are any covalently bonded carriers that release a compound of structure I, Ia, Ib, Ic in vivo when such prodrug is administered to a patient. Prodrugs are generally prepared by modifying functional groups in a way such that the modification is cleaved, either by routine manipulation or in vivo, yielding the parent compound.

The compounds (I), (Ia), (Ib) of the invention may be in crystalline forms. In certain embodiments, the crystalline forms of the compounds (I) (Ia), (Ib) are polymorphs.

The subject invention also includes isotopically labelled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into wh ich radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula (I) and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers or in one or more tautomeric forms. Accordingly, in certain embodiments, the compound of the Formulae (I) (Ia), (Ib), may exist in the form of other tautomers or geometrical isomers in some cases, depending on the kinds of the substituents. In the present specification, the compound may be described in only one form of such isomers, but the present invention includes such isomers, isolated forms of the isomers, or a mixture thereof. Furthermore, the compound of the Formulae (I) (Ia) (Ib) may have asymmetric carbon atoms or axial asymmetries in some cases, and correspondingly, it may exist in the form of optical isomers such as an (R)-form, an (S)-form, and the like. The present invention includes within its scope all such isomers, including racemates, enantiomers and mixtures thereof. Optionally, the compound of formula (I) is further separated into its enantiomers, i.e. (R)-enantiomer and (S)-enantiomer. In this case, the enantiomeric separation is performed by chiral HPLC.

In particular, within the scope of the present invention are included all stereoisomeric forms, including enantiomers, diastereoisomers, and mixtures thereof, including racemates and the general reference to the compounds of Formulae (I), (Ia), (Ib), include all the stereoisomeric forms, unless otherwise indicated.

The compounds described herein can exist in unsolvated as well as solvated forms with pharmaceutically acceptable solvents such as water, ethanol, and the like. The solvated forms of the compounds presented herein are also considered to be disclosed herein.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertible in the mammalian (e.g. human) body to the inventive compounds are however included.

VI. Medical Uses of Compounds of Formula (I), (Ia), (Ib)

In accordance with second aspect of the present invention compounds of Formula I, Ia or Ib are provided for use as a medicament.

In accordance with an additional aspect, the present invention provides the compounds of Formula (I), (Ia), (Ib), for inhibiting the activity of fatty acid amidase hydrolase (FAAH) and COX enzymes.

In accordance with another aspect the present invention provides the compounds of Formula (I), (Ia), (Ib), for use in treating diseases or disorders associated with increased (relative to physiological or desired) levels of FAAH and cyclooxygenase-1 (COX-1) and/or cyclooxygenase-2 (COX-2) activity or function.

In general, FAAH as referred herein means each or both the isoforms FAAH-1, FAAH-2.

In some embodiments, the compounds of Formula (I), (Ia), (Ib), and their pharmaceutical compositions and methods of administering them, are useful in treating diseases or disorders involving increased (compared to physiological) FAAH and/or COX activity.

The treatment with the compounds of the invention may be prophylactic or therapeutic.

The subject to be treated may be an animal (e.g., mouse, rat, non-human primate and non-human mammal) or human.

The treatment may or may not be administered in a combination therapy with another anti-tumoral, anti-inflammatory or analgesic agent.

The diseases and disorders which may be treated with the compounds of the invention include, but are not limited to, primary and metastatic neoplastic diseases or, in general, involving cell overproliferation, inflammatory related conditions or pain.

Diseases and disorders involving cell overproliferation include, but are not limited to, pre-malignant conditions, for example hyperplasia, metaplasia or dysplasia, cancers, cancer metastasis, benign tumors, hyperproliferative disorders and benign dysproliferative disorders.

Primary and metastatic neoplastic diseases and related disorders that can be treated and/or prevented by the methods, compounds and compositions of the presently disclosed subject matter include, but are not limited to, prostate cancers, colorectal cancers, liver cancer, head and neck cancer, breast cancer, melanoma, metastatic melanoma, precancerous skin conditions such as actinic keratosis, skin cancers such as squamous cell carcinoma and basal cell carcinoma, and hematological malignancies such as chronic myelogeneous leukemia. In accordance with certain embodiments the present invention provides a method for the treatment or prevention of cancer, cancer metastasis, inflammation, neuropathic pain, asthma, atherosclerosis, stenosis, psoriasis or atopic dermatitis, comprising the administration of a therapeutically effective compound of Formula (I), (Ia), (Ib) according to one or more of the embodiments described above, in a subject in need of treatment.

Cancers and related disorders that can be treated and/or prevented by the methods and compositions of the presently disclosed subject matter include, but are not limited to acute and chronic leukemia; polycythemia vera; lymphomas such as Hodgkin's disease or non-Hodgkin's disease; multiple myelomas, plasmacytoma; Waldenstrom's acroglobulinemia; gammopathy; heavy chain disease; bone and connective tissue sarcomas; brain tumors; breast cancer; adrenal cancer; thyroid cancer; pancreatic cancer; pituitary cancers; eye cancers; vaginal cancers; vulvar cancer; cervical cancers; uterine cancers; ovarian cancers; head and neck squamous cell cancers (HNSCCs), esophageal cancers; stomach cancers; colon cancers; rectal cancers; liver cancers; cholangiocarcinomas; testicular cancers, prostate cancers; penal cancers; oral cancers; basal cancers; salivary gland cancers; pharynx cancers; skin cancers; kidney cancers; Wilms' tumor; bladder cancers, myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas. In certain embodiments, the present invention provides for compounds of Formula (I), (Ia), (Ib) for the use in the treatment and/or prevention of breast cancer, prostate cancer, melanoma, alveolar cancer, or head and neck cancer.

In some embodiments, the compounds of Formula (I), and their pharmaceutical compositions and methods of administering them, are useful in treating or preventing a disease or disorder when administered in combination with other treatments.

In an additional aspect the present invention also concerns combination therapies or treatment with a compound of formula (I), (Ia), (Ib) or pharmaceutical composition containing them.

In some embodiments, the compounds of Formula (I), and their pharmaceutical compositions and methods of administering them, are useful in treating various cancers when administered in combination with other pharmacological agents or active ingredients.

In certain embodiments these pharmacological agents are chemotherapeutic agents including, but not limited to, doxorubicin, daunorubicin, etoposide, cisplatin, oxaliplatin, carboplatin, gemcitabine, 5-fluorouracil, capecitabine, tegafururacil (UFT), dacarbazine, fenretinide, camptothecin, irinotecan, fludarabine, vinblastine, taxol, mitomycin C.

In some embodiments, the compounds of Formula (I), and their pharmaceutical compositions and methods of administering them, are useful in treating various cancers when administered before, during or after patient's treatment with radiation therapy.

In certain embodiments, the present invention concerns a compound of formula (I) for use as an inhibitor of FAAH, COX-1 and/or COX-2 in the treatment of inflammatory diseases or pain.

In certain embodiments, the inflammatory disease(s) treated by administration of the compounds of the invention include Ankylosing Spondylitis, Atopic Dermatitis, Behçet's Disease, Buerger's Disease, Crohn's Disease, Demyelinating Sensory Polyradiculoneuropathy Type 1, Diabetes Familial Cold Auto-Inflammatory Syndrome, Juvenile Idiopathic Arthritis, Cystic Fibrosis, Muckle-Wells Syndrome, Psoriasis, Rheumatoid Arthritis, Atherosclerosis, Alzheimer's Ankylosing Spondylitis, Asthma, Colitis, Diverticulitis, Fibromyalgia, Hepatitis, Irritable Bowel Syndrome, Hyperplastic polyps and inflammatory polyps, Systemic Lupus Erythematosus, Nephritis, Parkinson's Disease, Ulcerative Colitis, and Pelvic Inflammatory Disease.

Cancer-related inflammation is an important process contributing to malignant disease, with common and defined factors at different stages of progression. As discussed by A. Mantovani et al. ("*Cancer-related inflammation*", *Nature* 454, 436-444, 24 Jul. 2008), the mediators and cellular effectors of inflammation are important constituents of the local environment of tumors. In some types of cancer, inflammatory conditions are present before a malignant change occurs. Conversely, in other types of cancer, an oncogenic change induces an inflammatory microenvironment that promotes the development of tumors. Regardless of its origin, 'smoldering' inflammation in the tumor microenvironment has many tumor-promoting effects. It aids in the proliferation and survival of malignant cells, promotes angiogenesis and metastasis, subverts adaptive immune responses, and alters responses to hormones and chemotherapeutic agents.

In other embodiments, the compounds of Formula (I) are useful in the treatment of chronic, acute, inflammatory or nociceptive pain.

In some embodiments, the compounds of Formula (I), and their pharmaceutical compositions and methods of administering them, are useful in treating or preventing a disease or disorder when administered in combination with other treatments.

In an additional aspect the present invention also concerns combination therapies or treatment with a pharmacologically active ingredient with a compound of formula I, Ia, Ib or pharmaceutical composition containing them.

The combined treatment may be simultaneous or not.

In some embodiments, the compounds of Formula (I), and their pharmaceutical compositions and methods of administering them, are useful in treating various cancers when administered before, during or after patient's treatment with radiation therapy.

In accordance with certain aspects the present invention provides a method for inhibiting the enzymes FAAH and COX-1 and/or COX-2 or for treating a disorder, condition or disease that benefit from inhibition of FAAH and COX-1 and/or COX-2, in a subject in need of treatment, said method comprising administering to the subject in need of treatment a therapeutically effective amount of a compound of formula I, Ia or Ib, and/or a pharmaceutically acceptable salt, metabolite, prodrug, solvate or N-oxide thereof.

VII. Pharmaceutical Compositions

In a third aspect, the invention provides pharmaceutical compositions of compounds of Formula (I), (Ia), (Ib). The pharmaceutical compositions of the present invention encompass any compositions made by admixing a compound of the present invention and a pharmaceutically acceptable carrier. Such compositions are suitable for pharmaceutical use in an animal or human. The pharmaceutical compositions of the present invention comprise a therapeutically effective amount of one or more compounds of Formula (I), (Ia), (Ib), or a pharmaceutically acceptable salt thereof, and a pharmaceutically acceptable carrier. A pharmaceutical composition may optionally contain other active ingredients.

The term "carrier" refers to a vehicle, excipient, diluent, or adjuvant with which the therapeutic or active ingredient is administered. Any carrier and/or excipient suitable for the form of preparation desired for administration is contemplated for use with the compounds disclosed herein.

The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

In certain embodiments, the compounds of the present invention can be combined as the active ingredient in intimate admixture with a suitable pharmaceutical carrier and/or excipient according to conventional pharmaceutical compounding techniques.

The compositions include compositions suitable for parenteral including subcutaneous, intramuscular, and intravenous, pulmonary, nasal, rectal, topical or oral administration. Suitable route of administration in any given case will depend in part on the nature and severity of the conditions being treated and on the nature of the active ingredient. An exemplary route of administration is the oral route. The compositions may be conveniently presented in unit dosage form and prepared by any of the methods well-known in the art of pharmacy. The preferred compositions include compositions suitable for oral, parenteral, topical, subcutaneous, or pulmonary, in the form of nasal or buccal inhalation, administration. The compositions may be prepared by any of the methods well-known in the art of pharmacy. The pharmaceutical compositions may be in the form of tablets, pills, capsules, solutions, suspensions, emulsion, powders, suppository and as sustained release formulations. If desired, tablets may be coated by standard aqueous or non-aqueous techniques. In certain embodiments such compositions and preparations can contain at least 0.1 percent of active compound. The percentage of active compound in these compositions may, of course, be varied and may conveniently be between about 1 percent to about 60 percent of the weight of the unit. The amount of active compound in such therapeutically useful compositions is such that a therapeutically effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. To prevent breakdown during transit through the upper portion of the gastrointestinal tract, the composition may be an enteric coated formulation.

Compositions for topical administration include, but are not limited to, ointments, creams, lotions, solutions, pastes, gels, sticks, liposomes, nanoparticles, patches, bandages and wound dressings. In certain embodiments, the topical formulation comprises a penetration enhancer.

Compositions for pulmonary administration include, but are not limited to, dry powder compositions consisting of the powder of a compound of Formula (I), (Ia), (Ib) or a salt thereof, and the powder of a suitable carrier and/or lubricant. The compositions for pulmonary administration can be inhaled from any suitable dry powder inhaler device known to a person skilled in the art. Administration of the compositions is performed under a protocol and at a dosage sufficient to reduce the inflammation and pain in the subject. In some embodiments, in the pharmaceutical compositions of the present invention the active principle or active principles are generally formulated in dosage units. The dosage unit may contain from 0.1 to 1000 mg of a compound of Formula (I), (Ia), (Ib), per dosage unit for daily administration. In some embodiments, the amounts effective for topical formulation will depend on the severity of the disease, disorder or condition, previous therapy, the individual's health status and response to the drug. In some embodiments, the dose is in the range from 0.001% by weight to about 60% by weight of the formulation. When used in combination with one or more other active ingredients, the compound of the present invention and the other active ingredients may be used in lower doses than when each is used singly. With respect to formulations with respect to any variety of routes of administration, methods and formulations for the administration of drugs are disclosed in *Remington's Pharmaceutical Sciences*, 17$^{th}$ Edition, Gennaro et al. Eds., Mack Publishing Co., 1985, and *Remington's Pharmaceutical Sciences*, Gennaro AR ed. 20$^{th}$ edition, 2000, Williams & Wilkins PA, USA, and *Remington: The Science and Practice of Pharmacy*, 21$^{st}$ Edition, Lippincott Williams & Wilkins Eds., 2005; and in *Ansel's Pharmaceutical Dosage Forms and Drug Delivery Systems*, 8$^{th}$ Edition. Lippincott Williams & Wilkins Eds., 2005, which are herein incorporated as reference.

VIII. Methods For Preparing Compounds of Formula (I), (Ia), (Ib)

Compounds of Formula (I), (Ia), (Ib), provided herein that inhibit the activity of FAAH and COX-1 and/or COX-2, may be synthesized using standard synthetic techniques known to those of skill in the art or using methods known in the art in combination with methods described herein. As a further guide the following synthetic methods may also be utilized. The reactions can be employed in a linear sequence to provide the compounds described herein or they may be used to synthesize fragments which are subsequently joined by the methods described herein and/or known in the art.

IX. Preparation of Compounds of The Invention

Compounds/agents of the invention that inhibit the activity of FAAH, COX-1 and COX-2 may be synthesized using standard synthetic techniques known to those of skill in the art or using methods known in the art in combination with methods described herein. As a further guide the following synthetic methods may also be utilized to synthetize the compounds provided here. Compounds may be synthesized using methodologies analogues to those described below by the use of appropriate alternative starting materials.

In certain embodiments, methods for the manufacture of the compounds of general formula (I) are provided herein

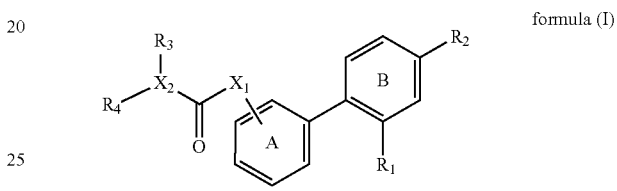

formula (I)

Wherein $X_1$, $X_2$, $R_1$, $R_2$, $R_3$, $R_4$, have the meanings as defined above, said methods comprising a carbamoylation reaction of compounds of formula (II)

formula (II)

in which $R_1$ and $R_2$ are as defined above and $Y_3$ is ortho-OH, meta-OH, ortho-NHR$_9$, meta-NHR$_9$ in which $R_9$ is as defined above under the condition reported in scheme 1, when, respectively, $Y_3$ is ortho-OH, meta-OH (formula IIa), or $Y_3$ is ortho-NR$_9$(CO)G, meta-NR$_9$(CO)G (formula IIb) in which $R_9$ is as defined above and G is Cl, 4-nitrophenoxy or imidazol-1-yl.

Scheme 1 formula IIa

RNCO,
DMAP, MeCN, rt
(where R = R$_3$ or R$_4$)

or triphosgene, DMAP,
NHR$_3$R$_4$, DCM
0° C. to rt

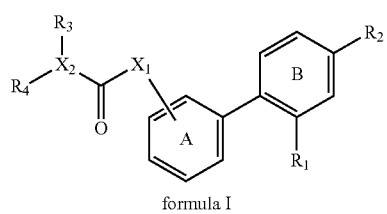

formula I

-continued
ROH,
DMAP, toluene
(where R = R₃ or R₄)

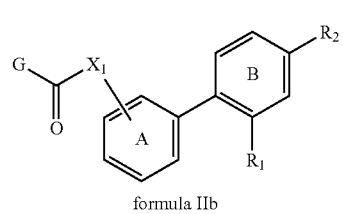

formula IIb

Treatment of compounds of formula (IIa) with an isocyanate in presence of a base, such as, N,N-dimethylaminopyridine (DMAP), in an organic solvent, such as, acetonitrile or treatment of compounds of formula (IIa) with triphosgene and amine NHR₃R₄ in which R₃ and R₄ are as defined above in presence of a base, such as, N,N-dimethylaminopyridine (DMAP), in an organic solvent, such as dichloromethane results in the formation of compounds of formula (I). Isocyanates are commercially available or methods for the preparation are well known in the art. Alternatively, the compounds of formula (I) can be prepared from compounds of formula (IIb) in which R₉ is as defined above and where G is Cl, 4-nitrophenoxy or imidazol-1-yl in the presence of a base, such as N,N-dimethylaminopyridine (DMAP), in an organic solvent, such as, toluene. Methods for the preparation of compounds of formula (IIb) are well known in the art.

The compounds of formula (II) can be prepared according to methods of literature by palladium-catalyzed reaction between an aryl halides or aryl triflates of formula (III)

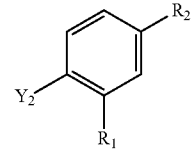

formula (III)

in which $R_1$ and $R_2$ are as defined above and $Y_2$ is bromine, or iodine, preferably iodine, or triflate with a boronic acid or ester Ar B(OL)$_2$ in which L is an alkyl chain. Boronic acids or the corresponding boronates are either commercially available or can be prepared from the corresponding halides according to methods known in literature. The compounds of formula (III) are commercially available or can be prepared according to methods known in literature.

In accordance with certain embodiments, a procedure for exemplary compounds according to Formula (I) is provided herein.

Scheme 2.
General procedures of exemplary compounds according to Formula (I)

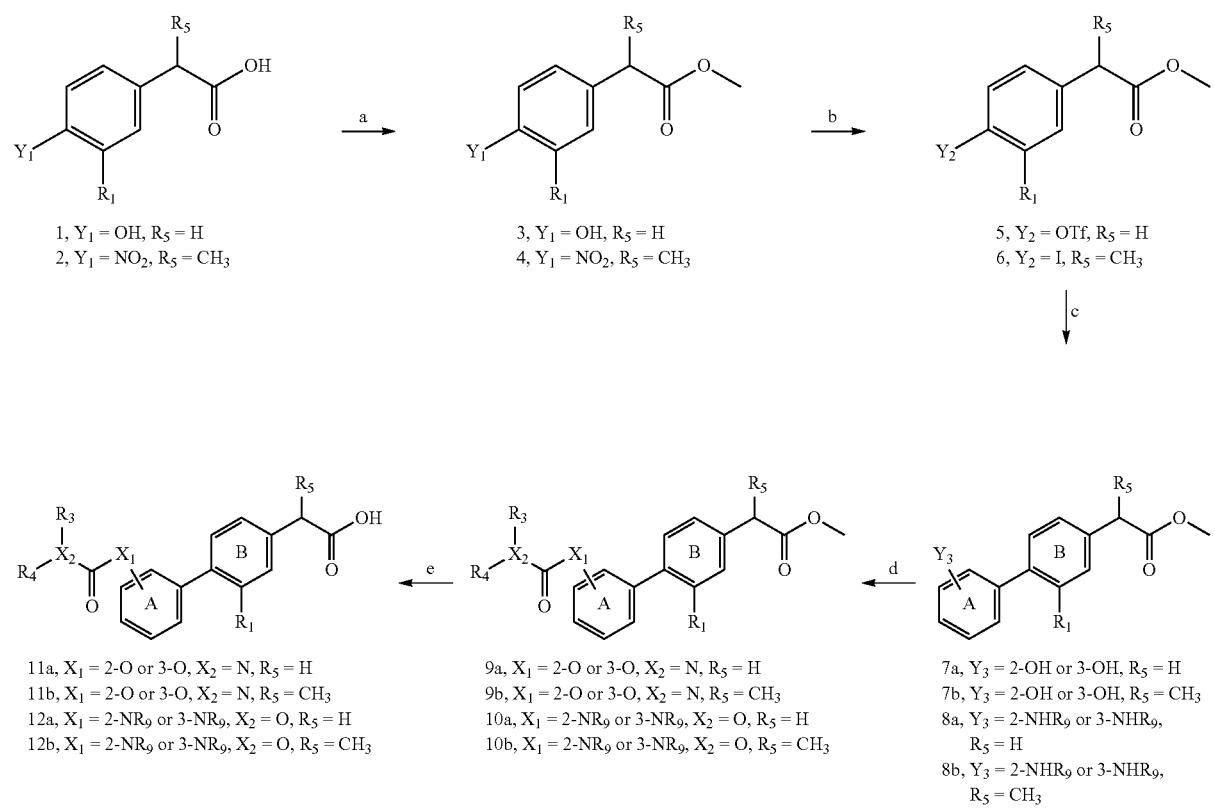

Reagents and conditions:
(a) MeOH, conc. H$_2$SO$_4$, rt, overnight;
(b) for compound 3: Tf$_2$O, Et$_3$N, DCM, rt, 1h; for compound 4: i) HCO$_2$NH$_4$, 10% Pd/C, MeOH, rt, 3 h;
   (ii) NaNO$_2$, 3M HCl, 0° C., 30 min, then NaI, 60° C., 2 h;
(c) ArB(OH)$_2$ or ArB(OL)$_2$, Pd(OAc)$_2$, K$_2$CO$_3$, EGME/H$_2$O, rt, 15 h;
(d) for compound 7a-b: RNCO (where R = R$_3$ or R$_4$), DMAP, MeCN, rt 15 h or triphosgene, DMAP, NHR$_3$R$_4$, DCM, 0° C. to rt; for compound 8a-b: triphosgene, toluene, reflux, 15 h, then ROH (where R = R$_3$ or R$_4$), DMAP, rt, 15 h;
(e) 6M HCl, THF, rt, 48 h.

Carbamate intermediates 9a-b of Scheme 2 were synthesized by a carbamoylation reaction of the phenol intermediates 7a-b of Scheme 2 with the corresponding isocyanates or alternatively activating the hydroxyl group of phenol intermediates 7a-b of Scheme 2 with triphosgene and then reacting with the corresponding amines. Reverse carbamate intermediates 10a-b of Scheme 2 were synthesized by a carbamoylation reaction by activating the amino group of aniline intermediates 8a-b of Scheme 2 with triphosgene and then reacting with corresponding alcohols. The acidic hydrolysis of the methyl ester functionalities of intermediates 9a-b and 10a-b of Scheme 2 afforded the corresponding acids 11a-b and 12a-b of Scheme 2. The intermediates 7a and 8a of Scheme 2 were prepared in three steps starting from carboxylic acid starting materials 1 of Scheme 2 which were converted in the corresponding methyl ester intermediates 3 of Scheme 2 under standard acidic conditions, to afford, after conversion to the corresponding triflate intermediates 5 of Scheme 2 and Suzuki cross coupling reactions, the biphenyl intermediates 7a and 8a. The intermediates 7b and 8b of Scheme 2 were prepared in four steps starting from carboxylic acid starting materials 2 of Scheme 2 (*Chinese Chem. Lett.*, 2006, 17, 461-464; *J. Med. Chem.*, 1983, 26(2), 222-226; *J. Med. Chem.*, 1977, 20(6), 797-801) which were converted in the corresponding methyl ester intermediates 4 of Scheme 2 under standard acidic conditions, to afford, after catalytic hydrogenation with ammonium formate and Pd in MeOH, and diazotation in presence of NaI, the aryl iodide intermediates 6 of Scheme 2. Finally, intermediates 6 of Scheme 2 were converted under Suzuki cross coupling conditions (*Eur. J. Org. Chem.*, 2009, 1, 110-116) in the biphenyl intermediates 7b and 8b of Scheme 2.

Any combinations of the substituents or groups as defined or described above for the various variables is contemplated herein.

The compounds of Formula (I), (Ia), (Ib), prepared with the methods described hereinabove may be treated or purified by conventional techniques or means for example by filtration, distillation, chromatography, recrystallization and combination thereof.

With the aim of better illustrating the present invention, without limiting it, the examples reported in Table 1 are provided herein.

The following are examples of compounds according to Formula (I), (Ia) or (Ib) of the invention.

TABLE 1

| Example | Structure | Formula | Name |
|---|---|---|---|
| 1 | 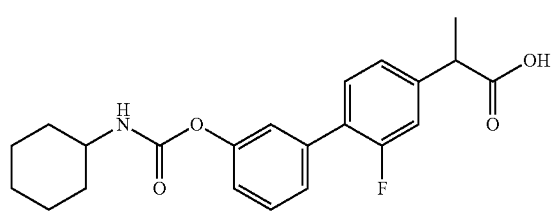 [SMILES: CC(C(=O)O)c1ccc(-c2cccc(OC(=O)NC3CCCCC3)c2)c(F)c1] | C$_{22}$H$_{24}$FNO$_4$ | 2-[4-[3-(cyclohexyl-carbamoyloxy)phenyl]-3-fluoro-phenyl]propanoic acid |
| 2 | 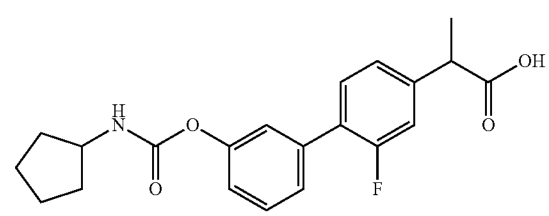 [SMILES: CC(C(=O)O)c1ccc(-c2cccc(OC(=O)NC3CCCC3)c2)c(F)c1] | C$_{21}$H$_{22}$FNO$_4$ | 2-[4-[3-(cyclopentyl-carbamoyloxy)phenyl]-3-fluoro-phenyl]propanoic acid |
| 3 | 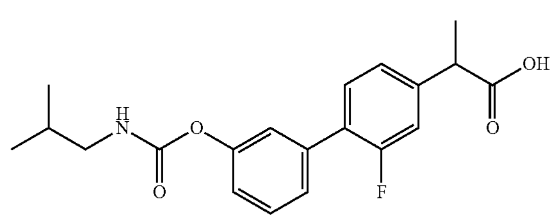 [SMILES: CC(C)CNC(=O)Oc1cccc(-c2ccc(C(C)C(=O)O)cc2F)c1] | C$_{20}$H$_{22}$FNO$_4$ | 2-[3-fluoro-4-[3-(isobutyl-carbamoyloxy)phenyl]phenyl]propanoic acid |

TABLE 1-continued

| Example | Structure | Formula | Name |
|---|---|---|---|
| 4 | 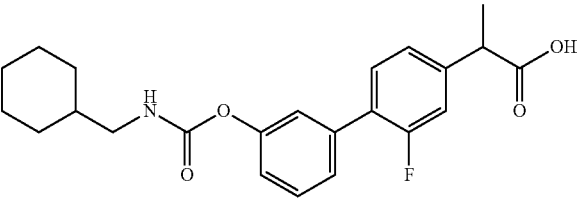 [SMILES: CC(C(=O)O)c1ccc(-c2cccc(OC(=O)NCC3CCCCC3)c2)c(F)c1] | $C_{23}H_{26}FNO_4$ | 2-[4-[3-(cyclohexylmethyl-carbamoyloxy)phenyl]-3-fluoro-phenyl]propanoic acid |
| 5 | 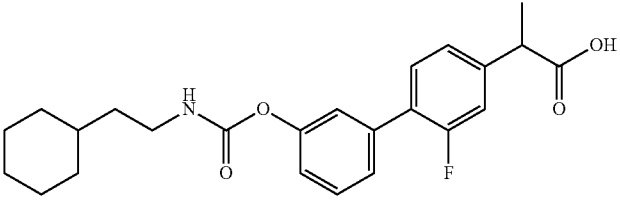 [SMILES: CC(C(=O)O)c1ccc(-c2cccc(OC(=O)NCCC3CCCCC3)c2)c(F)c1] | $C_{24}H_{28}FNO_4$ | 2-[4-[3-(2-cyclohexylethyl-carbamoyloxy)phenyl]-3-fluoro-phenyl]propanoic acid |
| 6 | 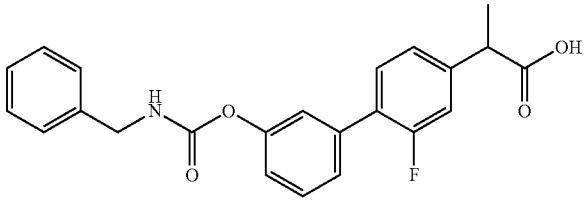 [SMILES: CC(C(=O)O)c1ccc(-c2cccc(OC(=O)NCc3ccccc3)c2)c(F)c1] | $C_{23}H_{20}FNO_4$ | 2-[4-[3-(benzyl-carbamoyloxy)phenyl]-3-fluoro-phenyl]propanoic acid |
| 7 | 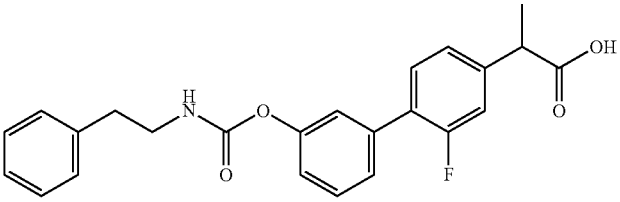 [SMILES: CC(C(=O)O)c1ccc(-c2cccc(OC(=O)NCCc3ccccc3)c2)c(F)c1] | $C_{24}H_{22}FNO_4$ | 2-[3-fluoro-4-[3-(phenethyl-carbamoyloxy)phenyl]phenyl]propanoic acid |
| 8 | 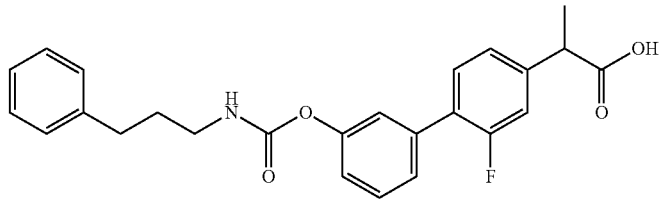 [SMILES: CC(C(=O)O)c1ccc(-c2cccc(OC(=O)NCCCc3ccccc3)c2)c(F)c1] | $C_{25}H_{24}FNO_4$ | 2-[3-fluoro-4-[3-(3-phenylpropyl-carbamoyloxy)phenyl]phenyl]propanoic acid |
| 9 | 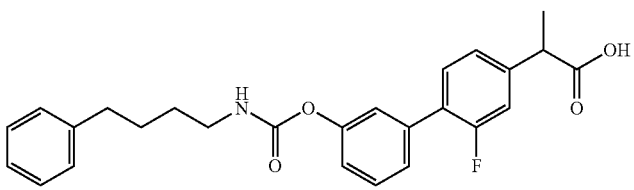 [SMILES: CC(C(=O)O)c1ccc(-c2cccc(OC(=O)NCCCCc3ccccc3)c2)c(F)c1] | $C_{26}H_{26}FNO_4$ | 2-[3-fluoro-4-[3-(4-phenylbutyl-carbamoyloxy)phenyl]phenyl]propanoic acid |
| 10 | 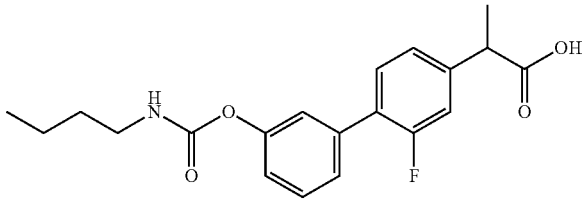 [SMILES: CCCCNC(=O)Oc1cccc(-c2ccc(C(C)C(=O)O)cc2F)c1] | $C_{20}H_{22}FNO_4$ | 2-[4-[3-(butylcarbamoyloxy)phenyl]-3-fluoro-phenyl]propanoic acid |

TABLE 1-continued

| Example | Structure | Formula | Name |
|---|---|---|---|
| 11 | 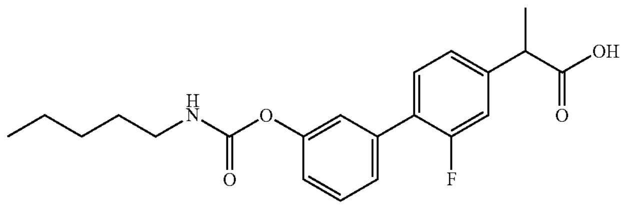 [SMILES: CCCCCNC(=O)Oc1cccc(-c2ccc(C(C)C(=O)O)cc2F)c1] | $C_{21}H_{24}FNO_4$ | 2-[3-fluoro-4-[3-(pentyl-carbamoyloxy)phenyl]phenyl] propanoic acid |
| 12 | 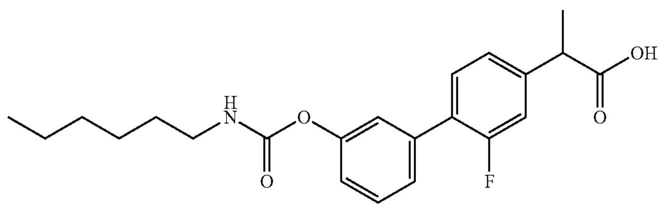 [SMILES: CCCCCCNC(=O)Oc1cccc(-c2ccc(C(C)C(=O)O)cc2F)c1] | $C_{22}H_{26}FNO_4$ | 2-[3-fluoro-4-[3-(hexyl-carbamoyloxy)phenyl]phenyl] propanoic acid |
| 13 | 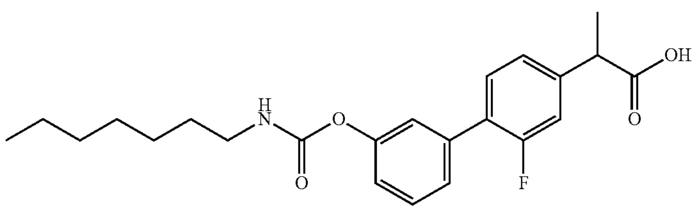 [SMILES: CCCCCCCNC(=O)Oc1cccc(-c2ccc(C(C)C(=O)O)cc2F)c1] | $C_{23}H_{28}FNO_4$ | 2-[3-fluoro-4-[3-(heptyl-carbamoyloxy)phenyl]phenyl] propanoic acid |
| 14 | 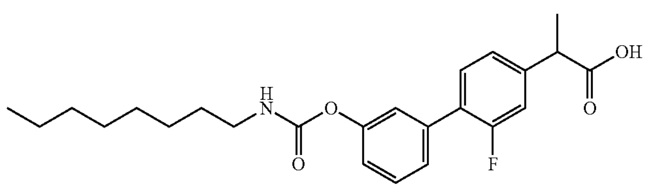 [SMILES: CCCCCCCCNC(=O)Oc1cccc(-c2ccc(C(C)C(=O)O)cc2F)c1] | $C_{24}H_{30}FNO_4$ | 2-[3-fluoro-4-[3-(octyl-carbamoyloxy)phenyl]phenyl] propanoic acid |
| 15 | 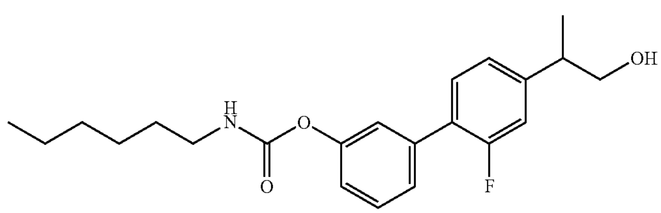 [SMILES: CCCCCCNC(=O)Oc1cccc(-c2ccc(C(C)CO)cc2F)c1] | $C_{22}H_{28}FNO_3$ | [3-[2-fluoro-4-(2-hydroxy-1-methyl-ethyl)phenyl]phenyl] N-hexylcarbamate |
| 16 | 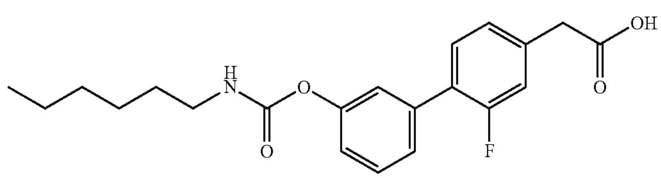 [SMILES: CCCCCCNC(=O)Oc1cccc(-c2ccc(CC(=O)O)cc2F)c1] | $C_{21}H_{24}FNO_4$ | 2-[3-fluoro-4-[3-(hexyl-carbamoyloxy)phenyl]phenyl] acetic acid |
| 17 | 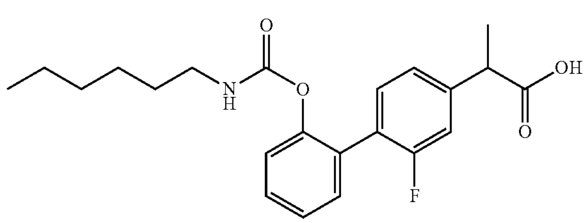 [SMILES: CCCCCCNC(=O)Oc1ccccc1-c1ccc(C(C)C(=O)O)cc1F] | $C_{22}H_{26}FNO_4$ | 2-[3-fluoro-4-[2-(hexyl-carbamoyloxy)phenyl]phenyl] propanoic acid |

TABLE 1-continued

| Example | Structure | Formula | Name |
|---|---|---|---|
| 18 | 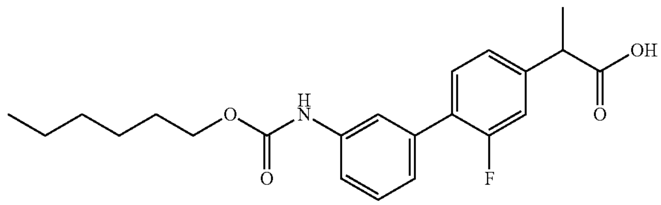 [SMILES: CCCCCCOC(=O)Nc1cccc(-c2ccc(C(C)C(=O)O)cc2F)c1] | $C_{22}H_{26}FNO_4$ | 2-[3-fluoro-4-[3-(hexoxy-carbonylamino)phenyl]phenyl] propanoic acid |
| 19 [(−)-12] | 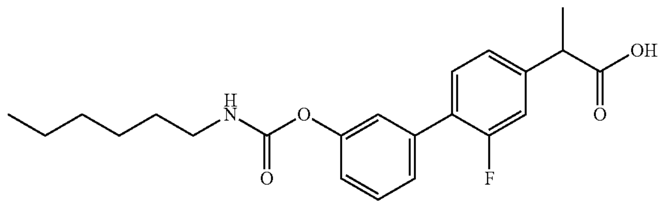 [SMILES: CCCCCCNC(=O)Oc1cccc(-c2ccc(C(C)C(=O)O)cc2F)c1] | $C_{22}H_{26}FNO_4$ | (−)-2-[3-fluoro-4-[3-(hexyl-carbamoyloxy)phenyl]phenyl] propanoic acid |
| 20 [(+)-12] | 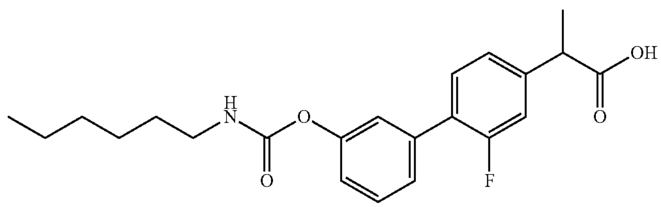 [SMILES: CCCCCCNC(=O)Oc1cccc(-c2ccc(C(C)C(=O)O)cc2F)c1] | $C_{22}H_{26}FNO_4$ | (+)-2-[3-fluoro-4-[3-(hexyl-carbamoyloxy)phenyl]phenyl] propanoic acid |

METHODS FOR TESTING COMPOUNDS OF THE INVENTION

In Vitro Rat FAAH Radiometric Assay

Rat FAAH was prepared from male Sprague Dawley rat brains, homogenized in a potter in 20 mM of Tris HCl pH 7.4, 0.32 M sucrose.

The radiometric assay used to measure FAAH activity was performed in eppendorf tubes: 50 μg of total rat brain homogenate were pre-incubated in 445.5 μL of assay buffer (50 mM Tris-HCl pH7.4, 0.05% Fatty acid-free bovine serum albumin (BSA)) with 4.5 μL of inhibitor (at appropriate concentration in DMSO) or DMSO alone (to measure FAAH total activity) for 10 minutes at 37° C. The blank (no activity control) was prepared using 445.5 μL of assay buffer and 4.5 μL of DMSO without the 50 μg of total rat brain homogenate.

After 10 minutes of pre-incubation with test compounds, the reaction was started by adding of 50 μL of substrate and incubating for 30 min at 37° C. The substrate was prepared in assay buffer in order to achieve the final concentration of 1 μM arachidonoyl ethanolamide (Cayman Chemical N. 90050) and 0.6 nM anandamide [ethanolamine-1-$^3$H] (American Radiolabeled Chemicals Inc., ART. 0626, conc. 1 mCi/mL, S.A. 60 Ci/mmol). The reaction was stopped by adding cold 1:1 CHCl$_3$/MeOH. After 10 minutes of centrifugation (845×g at 4° C.) 600 μL of aqueous phase were transferred into scintillation vials previously filled with 3 mL of scintillation fluid (Ultima Gold™, Perkin Elmer Inc., Cat. 6013329). Radioactivity was measured by liquid scintillation counting (MicroBeta2 LumiJET Perkin Elmer Inc.).

In Vitro Human FAAH Fluorescent Assay

Human recombinant FAAH was obtained from a HEK-293 FAAH-1 overexpressing stable cell line. Cells were grown in DMEM medium containing 10% FBS, 1% pen/strep, 1% glutamine and 500 μg/mL G418. To obtain membrane preparation cells were scraped off with cold phosphate-buffered saline (PBS) and collected by centrifugation (500×g, 10 minutes, 4° C.); the cell pellet was re-suspended in 20 mM Tris-HCl pH 7.4, 0.32 M sucrose, disrupted by sonication (10 pulses, 5 times) and centrifuged (800×g, 15 minutes, 4° C.); the collected supernatant was centrifuged at 105,000×g for 1 h at 4° C. and the pellet was re-suspended in PBS.

The fluorescent assay to measure FAAH activity was performed in 96 wells black plates: 2.5 μg of human FAAH-1 membrane preparation were pre-incubated for 50 minutes at 37° C., in 180 μL of assay buffer (50 mM TrisHCl pH 7.4, 0.05% Fatty acid-free BSA) with 10 μL of inhibitor or 10 μL DMSO to measure FAAH total activity. The background (no activity) samples were prepared using 180 μL of assay buffer without human FAAH-1 and 10 μL of DMSO. The reaction was then started by the addition of 10 μL of substrate (AMC arachidonyl amide, N. 10005098, Cayman Chemical) dissolved in ethanol and used at a final concentration of 2 μM. The reaction was carried out for 30 minutes at 37° C. and fluorescence was measured with a Tecan Infinite M200 nanoquant plate reader (excitation wavelength 350 nm/emission wavelength 460 nm).

In Vitro COX Assay

COX activity was measured using a commercial kit (COX Inhibitor Screening Assay Kit—Cayman Chemical N. 560131) which includes both ovine COX-1 and human recombinant COX-2 enzymes. Inhibitors were pre-incubated with either ovine COX-1 or human COX-2 in order to screen isozyme-specific inhibition. Differently than described in the kit protocol, the reaction was carried out in the presence of 5 μM arachidonic acid while for the blank sample (no activity) the two enzymes were inactivated for 40 minutes at 100° C. It was then measured the amount of PGF2α produced by reduction with SnCl$_2$ of COX-derived PGH2, via enzyme immunoassay (EIA) using a PG-specific antibody and competing with a PG-acetylcholinesterase conjugate.

Absorbance was measured at 412 nm with a Tecan Infinite M200 plate reader and data were processed according to manufacturer's instructions.

The median inhibitory concentrations ($IC_{50}$) were determined by non-linear regression analysis of the Log [concentration]/response curves generated with mean replicate values using a four parameter Hill equation curve fitting with GraphPad Prism 5 (GraphPad Software Inc., CA-USA). $IC_{50}$ of the examples 1-20 reported in aforementioned Table 1 are provided below. Values are means of ≥3 experiments performed in duplicate

| Example | rat FAAH $IC_{50}$ (μM) | human FAAH $IC_{50}$ (μM) | ovine COX-1 $IC_{50}$ (μM) | human COX-2 $IC_{50}$ (μM) |
|---|---|---|---|---|
| 1 | 8.2 | 1.8 | 7.9 | not active up to 30 μM |
| 2 | 4.8 | 1.8 | 4.4 | not active up to 30 μM |
| 3 | 5.6 | 1.6 | 8.2 | not active up to 30 μM |
| 4 | 0.36 | 0.28 | 0.60 | not active up to 30 μM |
| 5 | 0.018 | 0.009 | 0.15 | 11 |
| 6 | 4.2 | 7.2 | 1.3 | not active up to 30 μM |
| 7 | 0.17 | 0.070 | 6.3 | not active up to 30 μM |
| 8 | 0.09 | 0.022 | 0.58 | 6.2 |
| 9 | 0.027 | 0.013 | 3.7 | not active up to 30 μM |
| 10 | 7.0 | 1.5 | 0.26 | not active up to 30 μM |
| 11 | 0.57 | 0.092 | 0.020 | 0.16 |
| 12 | 0.031 | 0.010 | 0.012 | 0.43 |
| 13 | 0.011 | 0.006 | 0.37 | 0.32 |
| 14 | 0.0026 | 0.004 | 0.99 | 29 |
| 15 | 0.0033 | 0.0091 | 1.1 | not active up to 30 μM |
| 16 | 0.063 | 0.016 | 2.1 | 0.24 |
| 17 | 2.2 | 0.74 | 0.72 | not active up to 30 μM |
| 18 | 15 | 21 | 0.030 | 0.17 |
| 19 [(−)-12] | 0.0099 | 0.0086 | 13 | 54 |
| 20 [(+)-12] | 0.0094 | 0.0097 | 0.000010 | 0.010 |

Examples (5), (8), (11-14) (16) and (18-20) show a multitarget inhibition activity against FAAH, and both COX-1 and COX-2. These examples show a better multi-target FAAH/COX activity compared to the ibu-am5, which is the most active multitarget FAAH/COX compound reported to date in the literature. Ibu-am5 is reported to have FAAH $IC_{50}$=2.7 μM, and COX-inhibiting similar to ibuprofen (Holt S. et al., *J. Eur. J. Pharmacol.* 2007, 565, 26; Fowler C. J. et al. Br. J. Pharmacol. 2009, 156, 412; Fowler C. J. et al., *Journal of Enzyme Inhibition and Medicinal Chemistry*, 2012, 6, 1).

In Vivo Activity

Materials and Methods

Animals

Male CD1 mice, weighing 25-30 g, (Charles River, Calco, Italy) were used. Procedures were in accordance with the Ethical Guidelines of the International Association for the Study of Pain and were approved by Italian regulations on protection of animals used for experimental and other scientific purposes (D. M. 116192) as well as with European Economic Community regulations (O. J. of E. C. L 358/1 Dec. 18, 1986). Mice were housed in groups of 5 in ventilated cages containing autoclaved cellulose paper as nesting material, with free access to food and water. They were maintained under a 12 h light/dark cycle (lights on at 08:00 a.m.), at controlled temperature (21±1° C.) and relative humidity (55±10%). The animals are randomly divided in groups of 6 mice. Behavioral testing was performed between 9:00 a.m. and 5:00 p.m. Scientists running the experiments were not aware of the treatment protocol at the time of the test (blind procedure).

Carrageenan Test

The pro-inflammatory agent λ-carrageenan (1% weight-vol$^{-1}$ in sterile water, 50 μL) was injected into the left hind paw of slightly restrained mice, and paw volume was measured with a plethysmometer (Ugo Basile, Comerio, Italy), while thermal hyperalgesia was assessed by the method of Hargreaves et al. (1988), measuring the latency to withdraw the hind paw from a focused beam of radiant heat (thermal intensity: infrared 3.0) in a plantar test apparatus (Ugo Basile, Comerio, Italy). Cutoff time was set at 30 s. Withdrawal latencies were measured on both ipsilateral and contralateral paws at various time points after drug administration.

Drug solutions were prepared immediately before use in saline containing 10% PEG-400 and 10% Tween 80 and orally administered in a volume of 2.5 mL·kg$^{-1}$ before intraplantar injection of carrageenan.

TABLE 2

Structures and biological activities of Compound A and Compound of Example 12 of the invention are here reported.

| Compound | Structure | FAAH $IC_{50}$ (μM) | COX-1 $IC_{50}$ (μM) | COX-2 $IC_{50}$ (μM) |
|---|---|---|---|---|
| Compound A | 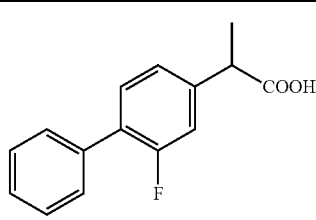 | >100 | 0.15 | 1.04 |

TABLE 2-continued

Structures and biological activities of Compound A and Compound of Example 12 of the invention are here reported.

| Compound | Structure | FAAH $IC_{50}$ (µM) | COX-1 $IC_{50}$ (µM) | COX-2 $IC_{50}$ (µM) |
|---|---|---|---|---|
| Example 12 | [structure: pentyl-NH-C(=O)-O-phenyl-phenyl(F)-CH(CH3)-COOH] | 0.031 | 0.012 | 0.430 |

The in vivo efficacy and toxicity of Compound A (selective COX inhibitor) is here compared with the in vivo efficacy and toxicity of the structurally related compound of example 12 (multitarget FAAH/COX inhibitor compound) (Table 2).

Gastric Lesions

To study the gastric irritation the protocol of Chan et al. (1995) was followed. Briefly, food-deprived (18-24 h) mice, using an oral gavage, received the COX inhibitor flurbiprofen (Kumar et al., 2008) (3-30 mg/kg, compound A in Table and figures), compound of the example 12 of the invention (3-100 mg/kg), or vehicle. Furthermore, a single pharmacologically effective dose of flurbiprofen (30 mg/kg), was studied in combination with compound of the example 12 (3-30 mg/kg). After 4 h, the mice were killed by $CO_2$ asphyxiation. The stomachs were removed, opened, rinsed in PBS, and the stomach lining was photographed. Scoring was done by observers blinded to experimental conditions, as previously reported (Jain et al., 2002): red coloration=0.5; spot ulcers=1; hemorrhagic streaks=1.5. If 3 or 4 ulcers were observed, a value of 2 was added to the score. If 5 or more ulcers were observed, a value of 3 was added to the score. The overall ulceration index was the sum of these scores, with a maximal value of 6.

Statistical Analyses

Results are expressed as the mean±S.E.M., or 95% confidence limits (95% CL). Efficacy data were compared using two-way analysis of variance (ANOVA) followed by Bonferroni's test for multiple comparisons. For gastric toxicity, the significance of differences between groups was determined by one-way ANOVA followed by a Bonferroni's test for multiple comparisons.

Results

Anti-inflammatory effects (FIG. 1, graphics A and C) and antihyperalgesic effects (FIG. 1, graphics B and D) in the mouse carrageenan model of acute inflammation. As shown in FIG. 1, the oral administration of compound of example 12 of the invention (3, 10, 30 and 100 mg/kg) produced a dose-dependent and persistent suppression of carrageenan-induced inflammation and hyperalgesia. $ED_{50}$ values for compound of the example 12 of the invention were 10 mg/kg on edema (Δ volume paw, CL 95%=14.2-119.8 mg/kg), and 10 mg/kg on thermal hyperalgesia (withdrawal latency, CL 95%=11.6-92.9 mg/kg). To further underline the unique pharmacological profile of multitarget FAAH/COX inhibitor compounds, we compare the potent FAAH/COX inhibitor of example 12 with compound A (selective COX inhibitor, Table 2). Compound of the example 12 of the invention given orally was more potent than oral compound A (3, 10, 30 and 100 mg/kg) at inhibiting the responses induced by carrageenan. $ED_{50}$ values for compound A were 30 mg/kg on edema (Δ volume paw, CL 95%=3.3-79.2 mg/kg), and 30 mg/kg on thermal hyperalgesia (withdrawal latency, CL 95%=7.2-72.8 mg/kg).

Effects on Gastric Ulcers

Irritation of the gastric mucosa is a common adverse event associated with the use of indomethacin and other NSAID COX inhibitors (Sostres et al., 2010).

Figure 2:
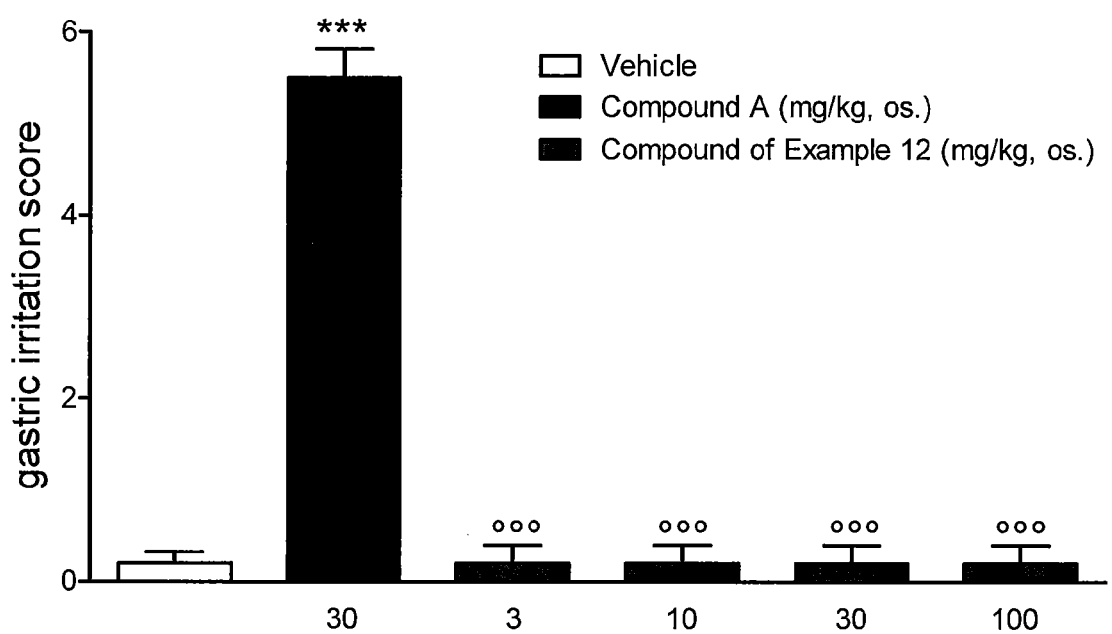
FIG. 2 shows bar graphs illustrating the side-effects following the administration of test compound A (flurbiprofen) compared to the low incidence of side effects following the administration of compound of example 12 of the invention.

Oral administration of flurbiprofen (30 mg/kg, compound A) to food-deprived mice was accompanied by profound gastric irritation and appearance of gastric ulcers, as shown in FIG. 2. It appears evident from FIG. 2 that the administration of compound of example 12 of the invention had no ulcerogenic effect up to 100 mg/kg.

EXAMPLES

The following Examples provide illustrative embodiments. In light of the present disclosure and the general level of skill in the art, those of skill can appreciate that the following Examples are intended to be exemplary only and that numerous changes, modifications, and alterations can be employed without departing from the scope of the presently disclosed subject matter.

Materials and Methods

In the procedure that follows, after the starting materials, reference to a description is typically provided. The starting material may not necessarily have been prepared from the description referred to.

Solvents and reagents were obtained from commercial suppliers and were used without further purification. For simplicity, solvents and reagents were indicated as follows: acetonitrile (MeCN), ammonium formate ($HCO_2NH_4$), chloroform ($CHCl_3$), cyclohexane (Cy), diatomaceous earth (Celite), dichloromethane (DCM), diethyl ether ($Et_2O$), dimethylsulfoxide (DMSO), N,N-dimethylformamide (DMF), 4-(dimethylamino)-pyridine (DMAP), ethyl acetate (EtOAc), ethylene glycol monomethyl ether (EGME), hydrochloric acid (HCl), methanol (MeOH), palladium acetate ($Pd(OAc)_2$), potassium carbonate ($K_2CO_3$), palladium on carbon (Pd/C), retention time (Rt), $SiO_2$ (silica gel), sodium bicarbonate ($NaHCO_3$), sodium iodide (NaI), sodium nitrite ($NaNO_2$), sodium sulphate ($Na_2SO_4$), sodium thiosulfate ($Na_2S_2O_3$), sulfuric acid ($H_2SO_4$), tetrahydrofuran (THF), triethylamine ($Et_3N$), t-butyl methyl ether (TBME), water ($H_2O$).

Automated column chromatography purifications were done using a Teledyne ISCO apparatus (CombiFlash® Rf) with pre-packed silica gel columns of different sizes (from 4 g until 120 g). Mixtures of increasing polarity of Cy and EtOAc or DCM and MeOH were used as eluents. Preparative TLC was performed using Macherey-Nagel pre-coated 0.5 mm TLC plates (SIL G-50 UV$_{254}$). NMR experiments were run on a Bruker Avance III 400 system (400.13 MHz for $^1$H, and 100.62 MHz for $^{13}$C), equipped with a BBI probe and Z-gradients. Spectra were acquired at 300 K, using deuterated dimethylsulfoxide (DMSO-d$_6$) or deuterated chloroform (CDCl$_3$) as solvents. Chemical shifts for 1H and $^{13}$C spectra were recorded using the residual non-deuterated solvent for calibration (CDCl$_3$: 7.26 ppm for $^1$H and 77.16 ppm for $^{13}$C; DMSO-d$_6$: 2.50 ppm for $^1$H; 39.52 ppm for $^{13}$C). Data are reported as follows: chemical shift (ppm), multiplicity (indicated as: bs, broad singlet; s, singlet; d, doublet; t, triplet; q, quartet; p, quintet, sx, sextet; m, multiplet and combinations thereof), coupling constants (J) in Hertz (Hz) and integrated intensity. UPLC/MS analyses were run on a Waters ACQUITY UPLC/MS system consisting of a SQD (Single Quadropole Detector) Mass Spectrometer equipped with an Electrospray Ionization interface and a Photodiode Array Detector. PDA range was 210-400 nm. Analyses were performed on an ACQUITY UPLC BEH C$_{18}$ column (50×2.1 mmID, particle size 1.7 μm) with a VanGuard BEH C$_{18}$ pre-column (5×2.1 mmID, particle size 1.7 μm). Mobile phase was either 10 mM NH$_4$OAc in H$_2$O at pH 5 adjusted with AcOH (A) and 10 mM NH$_4$OAc in MeCN—H$_2$O (95:5) at pH 5 (B). Electrospray ionization in positive and negative mode was applied. Purifications by preparative HPLC/MS were run on a Waters Autopurification system consisting of a 3100 Single Quadropole Mass Spectrometer equipped with an Electrospray Ionization interface and a 2998 Photodiode Array Detector. HPLC system included a 2747 Sample Manager, 2545 Binary Gradient Module, System Fluidic Organizer and 515 HPLC Pump. PDA range was 210-400 nm. Purifications were performed on a XBridge™ Prep C$_{18}$ OBD column (100×19 mmID, particle size 5 μm) with a XBridge™ Prep C$_{18}$ (10×19 mmID, particle size 5 μm) Guard Cartridge. Mobile phase was 10 mM NH$_4$OAc in H$_2$O at pH 5 adjusted with AcOH (A) and 10 mM NH$_4$OAc in MeCN—H$_2$O (95:5) at pH 5 (B). Electrospray ionization in positive and negative mode was used.

Compounds of the invention were subjected to chiral HPLC separation. Analyses by chiral HPLC were run on a Waters Alliance HPLC instrument consisting of an e2695 separation module and a 2998 photodiode array detector. The PDA range was 210-400 nm. Analyses were performed isocratic on a Daicel ChiralPak AD column (250×4.6 mm ID, particle size 10 μm). The mobile phase was 0.1% TFA heptane/EtOH (90:10), flow rate 1 mL/min, temperature 23° C. Separations by preparative chiral HPLC were run on a Waters Alliance HPLC instrument consisting of a 1525 binary HPLC pump, a Waters Fraction Collector III, and a 2998 photodiode array detector. UV detection was at 247.5 nm. Purifications were performed isocratic on a Daicel ChiralPak AD column (250×10 mm ID, particle size 10 μm). The mobile phase was 0.1% TFA heptane/EtOH (90:10), flow rate 5 mL/min, temperature 23° C. Optical rotations were measured on a Rudolf Research Analytical Autopol II automatic polarimeter using a sodium lamp (589 nm) as the light source (concentrations expressed in grams per 100 mL using CHCl$_3$ as the solvent and a 1 dm cell).

General Procedure for the Preparation of Biphenyl Intermediates 7-8 of Scheme 2 (Method A): To a solution of the corresponding boronic acid in EGME/H$_2$O (3:1, 4 ml) were added Pd(OAc)$_2$ (0.05 mmol) and K$_2$CO$_3$ (1.2 mmol), followed by the addition of aryl intermediates 5 or 6 of Scheme 2 (1 mmol). The dark reaction mixture was stirred at room temperature for 15 h, then diluted with EtOAc (40 ml) and filtered through a plug of Celite. The resulting filtrate was washed with H$_2$O (20 mL) and a 1 M solution of Na$_2$S$_2$O$_3$ (20 mL). After separation, the organic phase was dried over Na$_2$SO$_4$ and concentrated under reduced pressure. The residues were purified by column chromatography (Cy/EtOAc) to provide the corresponding biphenyls intermediates 7-8 of Scheme 2.

General Procedure for the Preparation of Carbamate Intermediates 9a-b of Scheme 2 (Method B): To a solution of the biphenyl intermediates 7a-b of Scheme 2 (1 mmol) in MeCN (0.5 M solution) was added DMAP (0.1 mmol) and the corresponding isocyanate (3 mmol). The resulting solution was stirred at room temperature for 15 h then the solvent was concentrated under reduced pressure. The residues were purified by column chromatography (Cy/EtOAc or DCM/MeOH) to provide the corresponding carbamate intermediates 9a-b of Scheme 2.

General Procedure for the Preparation of Reverse Carbamate Intermediates 10a-b of Scheme 2 (Method C): To a solution of the biphenyl intermediates 8a-b of Scheme 2 (1 mmol) in toluene (0.1 M solution) was added triphosgene (0.33 mmol) and the resulting mixture was refluxed for 15 h. DMAP (0.1 mmol) and the corresponding alcohol was then added (5 mmol). The resulting solution was stirred at room temperature for 15 h then the solvent was concentrated under reduced pressure. The residues were purified by column chromatography (Cy/EtOAc) to provide the corresponding reverse carbamate intermediates 10a-b of Scheme 2.

General Procedure for the Preparation of Acid Intermediates 11-12 of Scheme 2 (Method D): To a solution of the carbamate intermediates 9a-b of Scheme 2 or reverse carbamate intermediates 10a-b of Scheme 2 in THF (0.1 M solution) was added 6M HCl (5 mL) and the mixture was stirred at room temperature until the disappearance of the starting material was noted by UPLC-MS analysis. H$_2$O (10 mL) was added and the suspension was extracted with EtOAc (20 ml). After evaporation, the organic phase was dried over Na$_2$SO$_4$ and concentrated under reduced pressure. The residues were purified by crystallization (Et$_2$O/Cy, Et$_2$O/pentane, TBME), preparative TLC (Cy/EtOAc) or preparative HPLC.

Compound 1

2-(3-fluoro-4-nitro-phenyl)propanoic acid

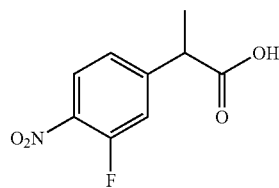

The title compound was obtained as brown clear oil (4.50 g, 81%), according to the procedure reported in the literature (*Chinese Chem. Lett.*, 2006,17, 461-464) starting from 2,4-difluoronitrobenzene (4.77 g, 30 mmol). $^1$H NMR (400 MHz, CDCl$_3$) δ 10.40 (bs, 1H), 8.06 (dd, J=8.1, $^4$J$_{H-F}$=8.1 HZ, 1H), 7.30 (m, 2H), 3.86 (q, J=7.2 Hz, 1H), 1.59 (d, J=7.2 Hz, 3H). MS (ES) C$_9$H$_8$FNO$_4$ requires 213, found 212 [M−H]$^-$.

Compound 2

Methyl 2-(4-amino-3-fluoro-phenyl)propanoate

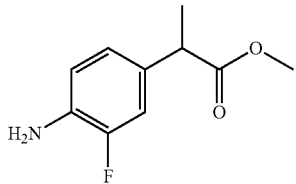

Step 1: To a solution of 2-(3-fluoro-4-nitrophenyl)propanoic acid (4.50 g, 21.11 mmol) in MeOH (40 mL), concentrated H$_2$SO$_4$ (0.1 mL) was added and the resulting solution was stirred overnight at room temperature. After solvent evaporation, the crude oil was diluted with Et$_2$O (15 mL) and filtered through a plug of SiO$_2$ to afford methyl 2-(3-fluoro-4-nitro-phenyl)propanoate as orange-brown oil (4.45 g, 93%). $^1$H NMR (400 MHz, CDCl$_3$) δ 8.03 (t, J=8.2 Hz, 1H), 7.26 (m, 2H), 3.83 (q, J=7.2 Hz, 1H), 3.70 (s, 3H), 1.54 (d, J=7.2 Hz, 3H). MS (ES) C$_{10}$H$_{10}$FNO$_4$ requires 227, found 226 [M−H]$^-$.

Step 2: To a solution of methyl 2-(3-fluoro-4-nitro-phenyl)propanoate (12.60 g, 55.46 mmol) in MeOH (222 mL) was added 10% Pd/C (2.35 g, 2.22 mmol) followed by addition of HCO$_2$NH$_4$ (20.98 g, 332.8 mmol). The solution was stirred at room temperature for 3 h. The solution was filtered through a plug of Celite and the filtrate was concentrated under reduced pressure. The residue was dissolved in EtOAc and filtered through a plug of SiO$_2$ to afford the title compound as an orange oil (10.33 g, 94%). $^1$H NMR (400 MHz, CDCl$_3$) δ 6.95 (dd, J=1.89, 12.07 Hz, 1H), 6.85 (dd, J=1.57, 8.15 Hz, 1H), 6.70 (dd, J=7.97, 9.37 Hz, 1H), 3.64 (s, 3H), 3.60 (q, J=7.10 Hz, 1H), 3.58 (s, 2H), 1.44 (d, J=7.22 Hz, 3H). MS (ES) C$_{10}$H$_{12}$FNO$_2$ requires: 197, found 198 [M+H]$^+$.

Compound 3

Methyl 2-(3-fluoro-4-iodo-phenyl)propanoate

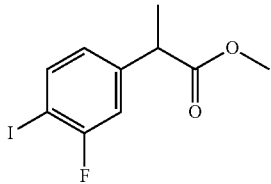

A solution of NaNO$_2$ (0.70 g, 10.21 mmol) in H$_2$O (1.5 mL) was added slowly to a solution of methyl 2-(4-amino-3-fluoro-phenyl)propanoate (1.75 g, 9.76 mmol) in a 3N HCl solution (29 mL) at 0° C. After 30 min, NaI (1.54 g, 10.25 mmol) was added at 0° C. under stirring. The resulting mixture was slowly warmed to room temperature in 5 min, and then heated at 60° C. for 3 h. After cooling down to room temperature, the mixture was extracted with Et$_2$O and the organic phase was then washed with a 1 M solution of Na$_2$S$_2$O$_3$ (15 mL) and dried over Na$_2$SO$_4$. The residue was dissolved in EtOAc (50 ml), treated with activated carbon and then filtered through a plug of Celite. The filtrate was concentrated under reduced pressure and the yellow oil was purified by column chromatography (Cy:EtOAc, 95:5) to give the title compound as a pale yellow oil (1.70 g, 55%). $^1$H NMR (400 MHz, CDCl$_3$) δ 7.67 (dd, J=6.64, 8.12 Hz, 1H), 7.03 (dd, J=1.99, 8.97 Hz, 1H), 6.85 (dd, J=2.00, 8.15 Hz, 1H), 3.67 (m, 4H), 1.48 (d, J=7.19 Hz, 3H). MS (ES) C$_{10}$H$_{10}$FIO$_2$ requires 308, found 325 [M+H$_2$O—H]$^-$.

Compound 4

Methyl 2-[3-fluoro-4-(2-hydroxyphenyl)phenyl]propanoate

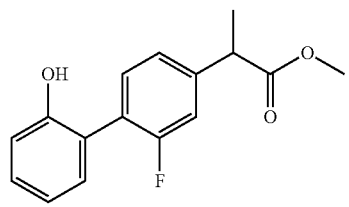 [SMILES: COC(=O)C(C)c1ccc(-c2ccccc2O)c(F)c1]

The title compound was prepared according to general method A using methyl 2-(3-fluoro-4-iodo-phenyl)propanoate (0.31 g, 1 mmol) and 3-hydroxyphenylboronic acid (0.17 g, 1.2 mmol). The crude was purified by column chromatography (Cy/EtOAc, 9:1) to afford the title compound as a white oil (230 mg, 84%). $^1$H NMR (400 MHz, CDCl$_3$) δ 7.34 (dd, J=8.3, 7.9 Hz, 1H), 7.30 (ddd, J=8.1, 7.5, 1.8 Hz, 1H), 7.23 (d, J=7.4 Hz, 1H), 7.19 (m, 2H), 7.00 (m, 2H), 4.98 (s, 1H), 3.78 (q, J=7.2 Hz, 1H), 3.71 (s, 3H), 1.55 (d, J=7.2 Hz, 3H). MS (ES) C$_{16}$H$_{15}$FO$_3$ requires 274, found 273 [M−H]$^-$.

Compound 5

Methyl 2-[3-fluoro-4-(3-hydroxyphenyl)phenyl]propanoate

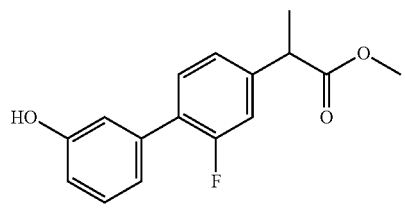 [SMILES: COC(=O)C(C)c1ccc(-c2cccc(O)c2)c(F)c1]

The title compound was prepared according to general method A using aryl iodide using methyl 2-(3-fluoro-4-iodo-phenyl)propanoate (3.27 g, 10.61 mmol) and 3-hydroxyphenylboronic acid (1.76 g, 12.74 mmol). The crude was purified by column chromatography (Cy/EtOAc 9:1) to afford the title compound as a white oil (2.46 g, 84%). $^1$H NMR (400 MHz, CDCl$_3$) δ 7.37 (t, J=8.1, 1H), 7.30 (t, J=7.9, 1H), 7.12 (m, 2H), 7.02 (m, 1H), 6.84 (dd, J=8.1, 2.4, 1H), 5.09 (s, 1H), 3.76 (q, J=7.2, 1H), 3.71 (s, 2H), 1.54 (d, J=7.2, 2H). $^{13}$C NMR (101 MHz, CDCl$_3$) δ 174.6, 159.6 (d, J=248.8), 155.5, 141.8 (d, J=7.5), 137.0, 130.7 (d, J=3.7), 129.6, 127.4 (d, J=13.3), 123.5 (d, J=2.0), 121.4, 115.9, 115.2 (d, J=23.6), 114.7, 52.2, 44.9, 18.3. MS (ES) C$_{16}$H$_{15}$FO$_3$ requires 274, found 273 [M−H]$^-$.

Compound 6

Methyl 2-[4-(3-aminophenyl)-3-fluoro-phenyl]propanoate

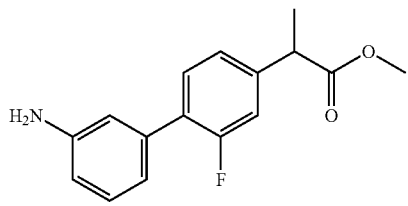 [SMILES: COC(=O)C(C)c1ccc(-c2cccc(N)c2)c(F)c1]

The title compound was prepared according to general method A using aryl iodide methyl 2-(3-fluoro-4-iodo-phenyl)propanoate (0.92 g, 3 mmol) and 3-aminobenzeneboronic acid monohydrate(0.56 g, 3.6 mmol). The crude was purified by column chromatography (Cy/EtOAc, 8:2) to afford the title compound as a yellow oil (750 mg, 91%) $^1$H NMR (400 MHz, CDCl$_3$) δ 7.37 (t, J=8.1 Hz, 1H), 7.23 (t, J=7.8 Hz, 1H), 7.11 (m, 2H), 6.95 (dq, J=7.6, 1.5 Hz, 1H), 6.90 (q, J=1.7 Hz, 1H), 6.74 (ddd, J=8.0, 2.3, 0.9 Hz, 1H), 3.75 (q, J=7.2 Hz, 1H), 3.70 (s, 3H), 1.53 (d, J=7.2 Hz, 3H). MS (ES) C$_{16}$H$_{16}$FNO$_2$ requires 273, found 274 [M+H]$^+$.

Compound 7

Methyl 2-[4-[3-(cyclohexylcarbamoyloxy)phenyl]-3-fluoro-phenyl]propanoate

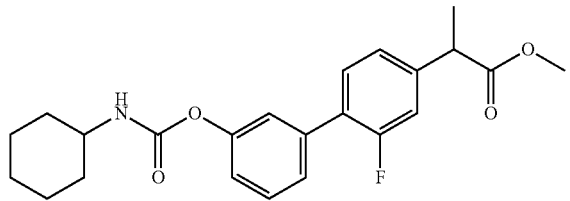 [SMILES: COC(=O)C(C)c1ccc(-c2cccc(OC(=O)NC3CCCCC3)c2)c(F)c1]

The title compound was prepared according to general method B using methyl 2-[3-fluoro-4-(3-hydroxyphenyl)phenyl]propanoate (274 mg, 1 mmol) and c-hexylisocianate (376 mg, 3 mmol). The crude was purified by column chromatography (Cy/EtOAc, 9:1) to afford the title compound as a white solid (261 mg, 65%). $^1$H NMR (400 MHz, CDCl$_3$) δ 7.38 (m, 3H), 7.30 (s, 1H), 7.12 (m, 3H), 4.93 (d, J=7.5, 1H), 3.75 (q, J=7.2, 1H), 3.70 (s, 3H), 3.57 (m, 1H), 2.02 (m, 2H), 1.74 (m, 2H), 1.62 (m, 1H), 1.53 (d, J=7.2, 3H), 1.37 (m, 2H), 1.23 (m, 3H). MS (ES) C$_{23}$H$_{26}$FNO$_4$ requires 399, found 400 [M+H]$^+$.

Compound 8 (Example 1)

2-[4-[3-(cyclohexylcarbamoyloxy)phenyl]-3-fluoro-phenyl]propanoic acid

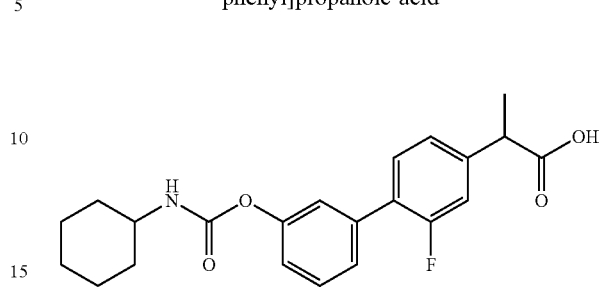

The title compound was prepared according to general method D using methyl 2-[4-[3-(cyclohexylcarbamoyloxy)phenyl]-3-fluoro-phenyl]propanoate (261 mg, 0.65 mmol). The crude was purified by preparative HPLC to afford the title compound as a white solid (65 mg, 26%). $^1$H NMR (400 MHz, DMSO-d$_6$) δ 12.45 (s, 1H), 7.73 (d, J=7.8, 1H), 7.50 (t, J=8.3, 1H), 7.47 (t, J=7.9, 1H), 7.37 (d, J=7.7, 1H), 7.24 (m, 3H), 7.14 (d, J=8.0, 1H), 3.78 (q, J=7.1, 1H), 3.33 (m, 1H), 1.84 (m, 2H), 1.71 (m, 2H), 1.56 (m, 1H), 1.41 (d, J=7.1, 3H), 1.23 (m, 5H). $^{13}$C NMR (101 MHz, DMSO-d$_6$) δ 174.7, 158.7 (d, J=246.1 Hz), 153.3, 151.2, 143.4 (d, J=8.0 Hz), 135.9, 130.6, 129.4, 125.7 (d, J=13.0 Hz), 125.1, 124.0, 121.8, 121.1, 115.1 (d, J=23.2 Hz), 49.7, 44.0, 32.4, 25.1, 24.5, 18.2. MS (ES) C$_{22}$H$_{24}$FNO$_4$ requires 385, found 386 [M+H]$^+$.

Compound 9

Methyl 2-[4-[3-(cyclopentylcarbamoyloxy)phenyl]-3-fluoro-phenyl]propanoate

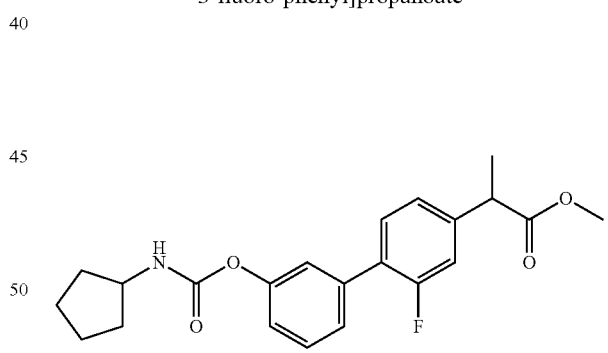

The title compound was prepared according to general method B using methyl 2-[3-fluoro-4-(3-hydroxyphenyl)phenyl]propanoate (274 mg, 1 mmol) and c-pentylisocianate (333 mg, 3 mmol). The crude was purified by column chromatography (Cy/EtOAc, 9:1) to afford the title compound as a white solid (235 mg, 61%). $^1$H NMR (400 MHz, CDCl$_3$) δ 7.38 (m, 3H), 7.30 (s, 1H), 7.12 (m, 3H), 4.98 (d, J=6.5 Hz, 1H), 4.07 (h, J=6.6 Hz, 1H), 3.75 (q, J=7.2 Hz, 1H), 3.70 (s, 3H), 2.02 (dt, J=12.1, 5.8 Hz, 2H), 1.66 (m, 4H), 1.53 (d, J=7.2 Hz, 3H), 1.49 (m, 2H). MS (ES) C$_{22}$H$_{24}$FNO$_4$ requires 385, found 386 [M+H]$^+$.

Compound 10 (Example 2)

2-[4-[3-(cyclopentylcarbamoyloxy)phenyl]-3-fluoro-phenyl]propanoic acid

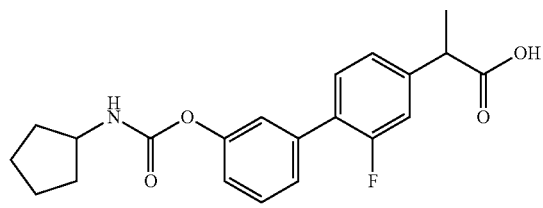 [SMILES: CC(C(=O)O)c1ccc(-c2cccc(OC(=O)NC3CCCC3)c2)c(F)c1]

The title compound was prepared according to general method D using methyl 2-[4-[3-(cyclopentylcarbamoyloxy) phenyl]-3-fluoro-phenyl]propanoate (235 mg, 0.61 mmol). The crude was purified by crystallization from TBME to afford the title compound as a white solid (95 mg, 42%). $^1$H NMR (400 MHz, DMSO-$d_6$) δ 12.47 (s, 1H), 7.81 (d, J=7.2, 1H), 7.50 (t, J=8.3, 1H), 7.47 (t, J=7.9, 1H), 7.37 (d, J=7.5, 1H), 7.23 (m, 3H), 7.14 (dd, J=7.9, 2.3, 1H), 3.85 (h, J=6.6, 1H), 3.78 (q, J=7.1, 1H), 1.83 (m, 2H), 1.67 (m, 2H), 1.50 (m, 4H), 1.41 (d, J=7.1, 3H). $^{13}$C NMR (101 MHz, DMSO-$d_6$) δ 174.7, 158.7 (d, J=247.4 Hz), 153.6, 151.1, 143.4 (d, J=7.8 Hz), 135.9, 130.6, 129.4, 125.7 (d, J=13.0 Hz), 125.1, 124.0, 121.8, 121.2, 115.1 (d, J=23.2 Hz), 52.3, 44.0, 32.1, 23.2, 18.2. MS (ES) $C_{21}H_{22}FNO_4$ requires 371, found 372 [M+H]$^+$.

Compound 11

Methyl 2-[4-[3-(cyclobutylcarbamoyloxy)phenyl]-3-fluoro-phenyl]propanoate

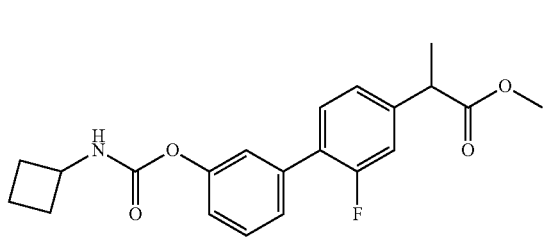 [SMILES: COC(=O)C(C)c1ccc(-c2cccc(OC(=O)NC3CCC3)c2)c(F)c1]

The title compound was prepared according to general method B using using methyl 2-[3-fluoro-4-(3-hydroxyphenyl)phenyl]propanoate (274 mg, 1 mmol) and c-butylisocianate (291 mg, 3 mmol). The crude colorless oil was used in the next step without further purification. MS (ES) $C_{21}H_{22}FNO_4$ requires 371, found 372 [M+H]$^+$.

Compound 12

2-[4-[3-(cyclobutylcarbamoyloxy)phenyl]-3-fluoro-phenyl]propanoic acid

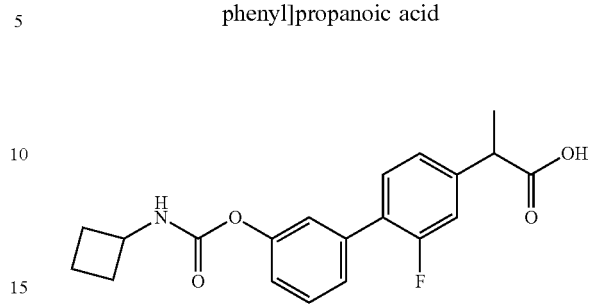

The title compound was prepared according to general method D using methyl 2-[4-[3-(cyclobutylcarbamoyloxy) phenyl]-3-fluoro-phenyl]propanoate. The crude was purified by preparative HPLC to afford the title compound as a white solid (66 mg, 37% over 2 steps). $^1$H NMR (400 MHz, DMSO-$d_6$) δ 12.47 (s, 1H), 8.10 (d, J=7.9, 1H), 7.49 (t, J=8.3, 1H), 7.46 (t, J=7.9, 1H), 7.38 (d, J=7.0, 1H), 7.23 (m, 3H), 7.13 (m, 1H), 4.02 (h, J=8.2, 1H), 3.78 (q, J=7.1, 1H), 2.18 (m, 2H), 1.98 (m, 2H), 1.61 (m, 2H), 1.41 (d, J=7.1, 3H). $^{13}$C NMR (101 MHz, DMSO-$d_6$) δ 174.7, 158.7 (d, J=246.2 Hz), 152.9, 151.0, 143.43 (d, J=7.7 Hz), 135.9, 130.6 (d, J=2.9 Hz), 129.4, 125.7 (d, J=12.7 Hz), 125.2, 124.0, 121.9, 121.2, 115.1 (d, J=23.3 Hz), 45.7, 44.0, 30.1, 18.2, 14.3. MS (ES) $C_{20}H_{20}FNO_4$ requires 357, found 358 [M+H]$^+$.

Compound 13

Methyl 2-[4-[3-(cyclopropylcarbamoyloxy)phenyl]-3-fluoro-phenyl]propanoate

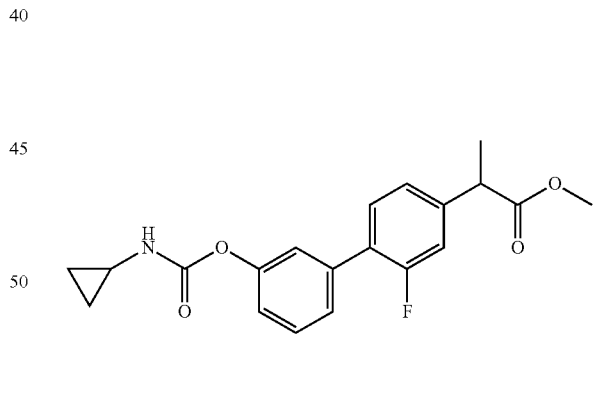

The title compound was prepared according to general method B using methyl 2-[3-fluoro-4-(3-hydroxyphenyl) phenyl]propanoate (274 mg, 1 mmol) and c-propylisocianate (250 mg, 3 mmol). The crude was purified by column chromatography (Cy/EtOAc, 9:1) to afford the title compound as a white solid (59 mg, 38%). $^1$H NMR (400 MHz, CDCl$_3$) δ 7.38 (m, 3H), 7.31 (s, 1H), 7.12 (m, 3H), 5.24 (s, 1H), 3.75 (q, J=7.2 Hz, 1H), 3.70 (s, 3H), 2.70 (m, 1H), 1.53 (d, J=7.2 Hz, 3H), 0.79 (m, 2H), 0.64 (m, 2H). MS (ES) $C_{20}H_{20}FNO_4$ requires 357, found 358 [M+H]$^+$.

Compound 14

2-[4-[3-(cyclopropylcarbamoyloxy)phenyl]-3-fluoro-phenyl]propanoic acid

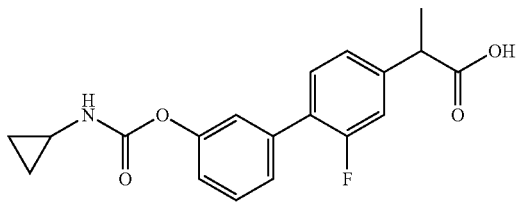 [SMILES: CC(C(=O)O)c1ccc(-c2cccc(OC(=O)NC3CC3)c2)c(F)c1]

The title compound was prepared according to general method D using methyl 2-[4-[3-(cyclopropylcarbamoyloxy)phenyl]-3-fluoro-phenyl]propanoate (59 mg, 0.17 mmol). The crude was purified by preparative HPLC to afford the title compound as a white solid (35 mg, 60%). $^1$H NMR (400 MHz, DMSO-$d_6$) δ 12.48 (s, 1H), 7.97 (d, J=2.3, 1H), 7.50 (t, J=8.4, 1H), 7.47 (t, J=7.9, 1H), 7.38 (d, J=7.5, 1H), 7.23 (m, 3H), 7.14 (d, J=7.9, 1H), 3.78 (q, J=7.1, 1H), 2.57 (m, 1H), 1.41 (d, J=7.1, 3H), 0.64 (m, 2H), 0.50 (m, 2H). $^{13}$C NMR (101 MHz, DMSO-$d_6$) δ 174.7, 158.7 (d, J=246.5 Hz), 154.8, 151.0, 143.4 (d, J=7.9 Hz), 135.9, 130.6 (d, J=2.2 Hz), 129.4, 125.7 (d, J=13.1 Hz), 125.2, 124.0, 121.8, 121.2, 115.1 (d, J=23.0 Hz), 44.0, 23.0, 18.2, 5.7. MS (ES) $C_{19}H_{18}FNO_4$ requires 343, found 344 [M+H]$^+$.

Compound 15

Methyl 2-[3-fluoro-4-[3-(isopropylcarbamoyloxy)phenyl]phenyl]propanoate

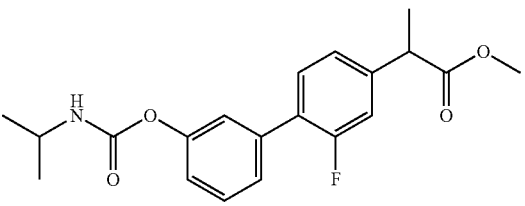 [SMILES: COC(=O)C(C)c1ccc(-c2cccc(OC(=O)NC(C)C)c2)c(F)c1]

The title compound was prepared according to general method B using methyl 2-[3-fluoro-4-(3-hydroxyphenyl)phenyl]propanoate (157 mg, 0.57 mmol) and isopropylisocyanate (145 mg, 1.71 mmol). The crude was purified by column chromatography (Cy/EtOAc, 8:2) to afford the title compound as a white solid (159 mg, 77%). $^1$H NMR (400 MHz, CDCl$_3$) δ 7.37 (m, 3H), 7.30 (s, 1H), 7.12 (m, 3H), 5.04 (d, J=7.1 Hz, 1H), 3.89 (m, 1H), 3.75 (q, J=7.2 Hz, 1H), 3.68 (s, 3H), 1.52 (d, J=7.2 Hz, 3H), 1.21 (d, J=6.6 Hz, 6H). MS (ES) $C_{20}H_{22}FNO_4$ requires 359, found 360 [M+H]$^+$.

Compound 16

2-[3-fluoro-4-[3-(isopropylcarbamoyloxy)phenyl]phenyl]propanoic acid

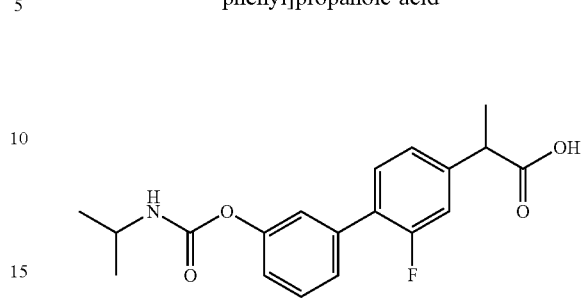

The title compound was prepared according to general method D using methyl 2-[3-fluoro-4-[3-(isopropylcarbamoyloxy)phenyl]phenyl]propanoate (159 mg, 0.44 mmol). The crude was purified by crystallization from pentane/Et$_2$O to afford the title compound as a white solid (65 mg, 43%). $^1$H NMR (400 MHz, DMSO-$d_6$) δ 12.43 (s, 1H), 7.73 (d, J=7.6 Hz, 1H), 7.51 (t, J=8.1 Hz, 1H), 7.48 (t, J=7.9 Hz, 1H), 7.39 (d, J=7.5 Hz, 1H), 7.25 (m, 3H), 7.15 (d, J=7.9 Hz, 1H), 3.79 (q, J=7.1 Hz, 1H), 3.67 (m, J=6.9 Hz, 1H), 1.42 (d, J=7.1 Hz, 3H), 1.15 (d, J=6.5 Hz, 6H). $^{13}$C NMR (101 MHz, DMSO-$d_6$) δ 175.3, 159.2 (d, J=246.5 Hz), 153.7, 151.6, 143.9 (d, J=8.0 Hz), 136.4, 131.1 (d, J=3.7 Hz), 129.8, 126.2 (d, J=13.1 Hz), 125.6, 124.5 (d, J=3.2 Hz), 122.3, 121.7, 115.6 (d, J=23.1 Hz), 44.5, 43.1, 22.8, 18.7. MS (ES) $C_{19}H_{20}FNO_4$ requires 345, found 346 [M+H]$^+$.

Compound 17

Methyl 2-[3-fluoro-4-[3-(isobutylcarbamoyloxy)phenyl]phenyl]propanoate

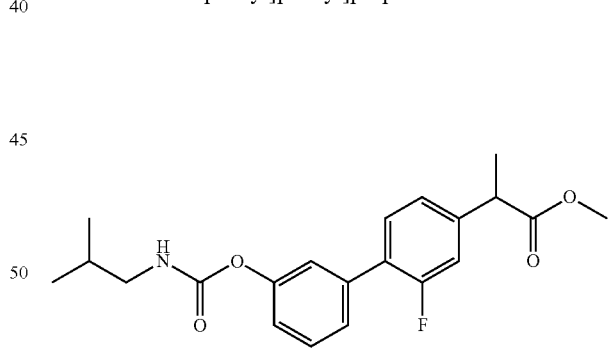

The title compound was prepared according to general method B using methyl 2-[3-fluoro-4-(3-hydroxyphenyl)phenyl]propanoate (129 mg, 0.47 mmol) and isobutylisocyanate (140 mg, 1.41 mmol). The crude was purified by column chromatography (Cy/EtOAc, 9:1) to afford the title compound as a white solid (138 mg, 78%). $^1$H NMR (400 MHz, CDCl$_3$) δ 7.39 (p, J=7.6 Hz, 3H), 7.30 (d, J=1.7 Hz, 1H), 7.12 (m, 3H), 5.09 (m, 1H), 3.75 (q, J=7.2 Hz, 1H), 3.70 (s, 3H), 3.11 (t, J=6.4 Hz, 2H), 1.85 (m, 1H), 1.53 (d, J=7.2 Hz, 3H), 0.97 (d, J=6.7 Hz, 6H). MS (ES) $C_{21}H_{24}FNO_4$ requires 373, found 374 [M+H]$^+$.

Compound 18 (Example 3)

2-[3-fluoro-4-[3-(isobutylcarbamoyloxy)phenyl]phenyl]propanoic acid

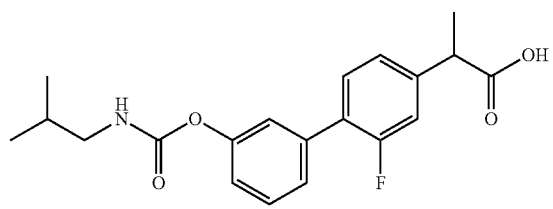 [SMILES: CC(C)CNC(=O)Oc1cccc(-c2ccc(C(C)C(=O)O)cc2F)c1]

The title compound was prepared according to general method D using methyl 2-[3-fluoro-4-[3-(isobutylcarbamoyloxy)phenyl]phenyl]propanoate (138 mg, 0.38 mmol). The crude was purified by crystallization from pentane/Et$_2$O to afford the title compound as a white solid (57 mg, 42%). $^1$H NMR (400 MHz, DMSO-d$_6$) δ 7.84 (t, J=5.9 Hz, 1H), 7.51 (t, J=8.1 Hz, 1H), 7.48 (t, J=7.9 Hz, 1H), 7.39 (d, J=7.7 Hz, 1H), 7.25 (m, 3H), 7.15 (dd, J=8.0, 1.5 Hz, 1H), 3.79 (q, J=7.1 Hz, 2H), 2.91 (t, J=6.4 Hz, 2H), 1.76 (hept, J=6.7 Hz, 1H), 1.42 (d, J=7.1 Hz, 3H), 0.90 (d, J=6.7 Hz, 6H). $^{13}$C NMR (101 MHz, DMSO-d$_6$) δ 175.2, 159.2 (d, J=246.3 Hz), 154.9, 151.7, 143.9 (d, J=7.7 Hz), 136.4, 131.1 (d, J=3.5 Hz), 129.9, 126.2 (d, J=13.1 Hz), 125.6, 124.5 (d, J=3.1 Hz), 122.3 (d, J=2.9 Hz), 121.6, 115.6 (d, J=23.1 Hz), 48.5, 44.5, 28.7, 20.4, 18.7. MS (ES) C$_{20}$H$_{22}$FNO$_4$ requires 359, found 360 [M+H]$^+$.

Compound 20 (Example 4)

2-[4-[3-(cyclohexylmethylcarbamoyloxy)phenyl]-3-fluoro-phenyl]propanoic acid

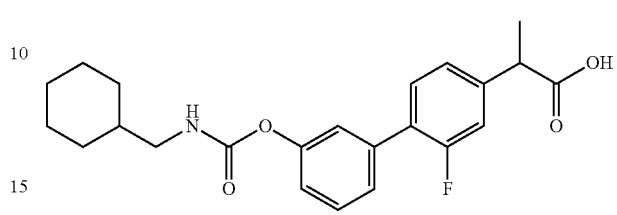

The title compound was prepared according to general method D using methyl 2-[4-[3-(cyclohexylmethylcarbamoyloxy)phenyl]-3-fluoro-phenyl]propanoate (157 mg, 0.38 mmol). The crude was purified by crystallization from pentane/Et$_2$O to afford the title compound as a white solid (93 mg, 61%). $^1$H NMR (400 MHz, DMSO-d$_6$) δ 12.46 (s, 1H), 7.79 (t, J=5.9 Hz, 1H), 7.48 (m, 2H), 7.37 (d, J=7.6 Hz, 1H), 7.24 (m, 3H), 7.13 (dd, J=7.6, 1.8 Hz, 1H), 3.78 (q, J=7.1 Hz, 1H), 2.92 (t, J=6.3 Hz, 2H), 1.67 (m, 5H), 1.46 (m, 1H), 1.41 (d, J=7.1 Hz, 3H), 1.18 (m, 3H), 0.90 (m, 2H). $^{13}$C NMR (101 MHz, DMSO-d$_6$) δ 175.2, 159.2 (d, J=246.4 Hz), 154.8, 151.7, 143.9 (d, J=7.6 Hz), 136.4, 131.1 (d, J=3.7 Hz), 129.9, 126.2 (d, J=13.0 Hz), 125.6, 124.5 (d, J=2.9 Hz), 122.3 (d, J=3.0 Hz), 121.6, 115.6 (d, J=23.3 Hz), 47.2, 44.5, 38.1, 30.7, 26.5, 25.8, 18.7. MS (ES) C$_{23}$H$_{26}$FNO$_4$ requires 399, found 400 [M+H]$^+$.

Compound 19

Methyl 2-[4-[3-(cyclohexylmethylcarbamoyloxy)phenyl]-3-fluoro-phenyl]propanoate

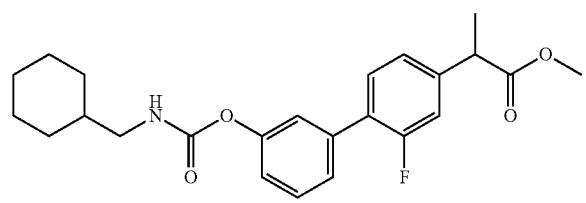 [SMILES: COC(=O)C(C)c1ccc(-c2cccc(OC(=O)NCC3CCCCC3)c2)c(F)c1]

The title compound was prepared according to general method B using methyl 2-[3-fluoro-4-(3-hydroxyphenyl)phenyl]propanoate (137 mg, 0.50 mmol) and c-hexylmethylisocyanate (209 mg, 1.5 mmol). The crude was purified by column chromatography (Cy/EtOAc, 9:1) to afford the title compound as a white solid (165 mg, 80%). $^1$H NMR (400 MHz, CDCl$_3$) δ 7.40 (m, 3H), 7.30 (dt, J=2.6, 1.6 Hz, 1H), 7.12 (m, 3H), 5.08 (t, J=5.5 Hz, 1H), 3.75 (q, J=7.2 Hz, 1H), 3.70 (s, 3H), 3.12 (t, J=6.4 Hz, 2H), 1.75 (m, 5H), 1.53 (m, 4H), 1.22 (m, 3H), 1.00 (m, 2H). MS (ES) C$_{24}$H$_{28}$FNO$_4$ requires 413, found 414 [M+H]$^+$.

Compound 21

Methyl 2-[4-[3-(2-cyclohexylethylcarbamoyloxyl)phenyl]-3-fluoro-phenyl]propanoate

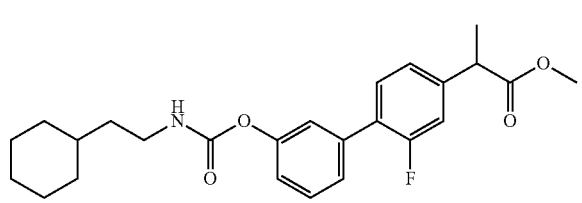 [SMILES: COC(=O)C(C)c1ccc(-c2cccc(OC(=O)NCCC3CCCCC3)c2)c(F)c1]

The title compound was prepared according to general method B using methyl 2-[3-fluoro-4-(3-hydroxyphenyl)phenyl]propanoate (137 mg, 0.50 mmol) and c-hexylethylisocyanate (230 mg, 1.5 mmol). The crude was purified by column chromatography (Cy/EtOAc, 9:1) to afford the title compound as a white solid (179 mg, 84%). $^1$H NMR (400 MHz, CDCl$_3$) δ 7.39 (m, 3H), 7.30 (m, 1H), 7.13 (m, 3H), 4.97 (t, J=5.3 Hz, 1H), 3.75 (q, J=7.2 Hz, 1H), 3.70 (s, 3H), 3.30 (q, J=7.2, 6.8 Hz, 2H), 1.70 (m, 5H), 1.53 (m, 6H), 1.24 (m, 3H), 0.96 (m, 2H). MS (ES) C$_{25}$H$_{30}$FNO$_4$ requires 427, found 428 [M+H]$^+$.

Compound 22 (Example 5)

2-[4-[3-(2-cyclohexylethylcarbamoyloxyl)phenyl]-3-fluoro-phenyl]propanoic acid (5)

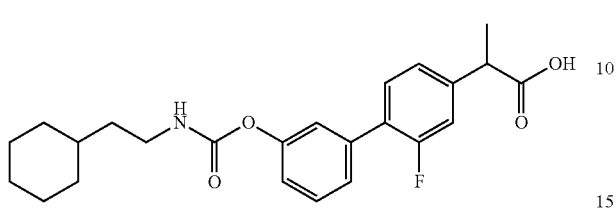

The title compound was prepared according to general method D using methyl 2-[4-[3-(2-cyclohexylethylcarbamoyloxyl)phenyl]-3-fluoro-phenyl]propanoate (149 mg, 0.35 mmol). The crude was purified by crystallization from pentane/Et$_2$O to afford the title compound as a white solid (98 mg, 68%). $^1$H NMR (400 MHz, DMSO-d$_6$) δ 12.07 (s, 1H), 7.74 (t, J=5.6 Hz, 1H), 7.48 (m, 2H), 7.37 (d, J=7.0 Hz, 1H), 7.23 (m, 3H), 7.13 (dd, J=7.7, 1.8 Hz, 1H), 3.78 (q, J=7.1 Hz, 1H), 3.09 (q, J=6.7 Hz, 2H), 1.66 (q, J=17.4, 15.6 Hz, 5H), 1.41 (d, J=7.1 Hz, 3H), 1.26 (m, 6H), 0.88 (q, J=10.4, 9.6 Hz, 2H). $^{13}$C NMR (101 MHz, DMSO-d$_6$) δ 174.7, 158.7 (d, J=246.5 Hz), 154.1, 151.2, 143.4 (d, J=7.8 Hz), 135.9, 130.6 (d, J=3.5 Hz), 129.4, 125.7 (d, J=13.1 Hz), 125.1, 124.0 (d, J=3.1 Hz), 121.8, 121.1, 115.1 (d, J=23.1 Hz), 44.0, 38.2, 36.6, 34.4, 32.6, 26.0, 25.7, 18.2. MS (ES) C$_{24}$H$_{28}$FNO$_4$ requires 413, found 414 [M+H]$^+$.

Compound 23

Methyl 2-[3-fluoro-4-[3-(phenylcarbamoyloxy)phenyl]phenyl]propanoate

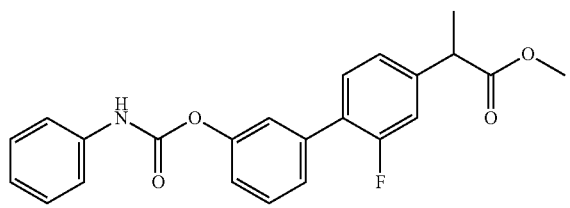 [SMILES: COC(=O)C(C)c1ccc(-c2cccc(OC(=O)Nc3ccccc3)c2)c(F)c1]

The title compound was prepared according to general method B using methyl 2-[3-fluoro-4-(3-hydroxyphenyl)phenyl]propanoate (137 mg, 0.5 mmol) and phenylisocyanate (179 mg, 3 mmol) as a colorless oil (161 mg) which was used in the next step without further purification. MS (ES) C$_{23}$H$_{20}$FNO$_4$ requires 393, found 394 [M+H]$^+$.

Compound 24

2-[3-fluoro-4-[3-(phenylcarbamoyloxy)phenyl]phenyl]propanoic acid

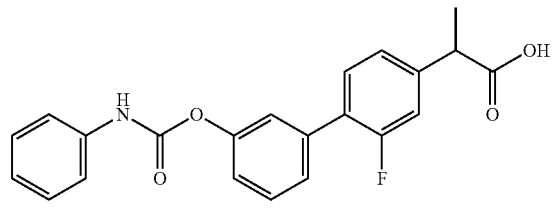 [SMILES: CC(C(=O)O)c1ccc(-c2cccc(OC(=O)Nc3ccccc3)c2)c(F)c1]

The title compound was prepared according to general method D using methyl 2-[3-fluoro-4-[3-(phenylcarbamoyloxy)phenyl]phenyl]propanoate (161 mg). The crude was purified by preparative HPLC to afford the title compound as a white solid (31 mg, 20% over last two steps). $^1$H NMR (400 MHz, DMSO-d$_6$) δ 12.48 (s, 1H), 10.26 (s, 1H), 7.53 (t, J=7.3 Hz, 4H), 7.45 (d, J=6.8 Hz, 1H), 7.40 (s, 1H), 7.33 (t, J=7.9 Hz, 2H), 7.26 (m, 3H), 7.05 (t, J=7.4 Hz, 1H), 3.78 (q, J=7.1 Hz, 1H), 1.41 (d, J=7.1 Hz, 3H). $^{13}$C NMR (101 MHz, DMSO-d$_6$) δ 174.7, 158.8 (d, J=246.5 Hz), 151.5, 150.5, 143.5 (d, J=8.0 Hz), 138.5, 136.1, 130.6 (d, J=2.9 Hz), 129.6, 128.8, 125.7, 125.6 (d, J=13.1 Hz), 124.0, 122.9, 122.0, 121.3, 118.4, 115.2 (d, J=23.3 Hz), 44.1, 18.2. MS (ES) C$_{22}$H$_{18}$FNO$_4$ requires 379, found 380 [M+H]$^+$.

Compound 25

Methyl 2-[4-[3-(benzylcarbamoyloxy)phenyl]-3-fluoro-phenyl]propanoate

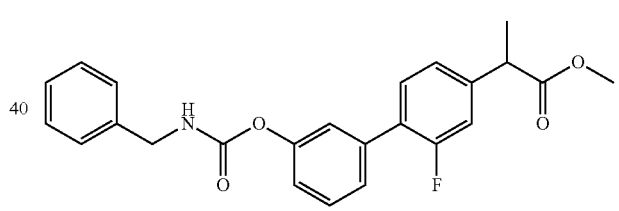

The title compound was prepared according to general method B using methyl 2-[3-fluoro-4-(3-hydroxyphenyl)phenyl]propanoate (137 mg, 0.5 mmol) and benzylisocyanate (199 mg, 1.5 mmol) as a colorless oil which was used in the next step without further purification. MS (ES) C$_{24}$H$_{22}$FNO$_4$ requires 407, found 408 [M+H]$^+$.

Compound 26 (Example 6)

2-[4-[3-(benzylcarbamoyloxy)phenyl]-3-fluoro-phenyl]propanoicacid

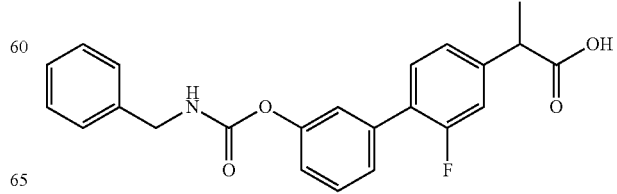

The title compound was prepared according to general method D using methyl 2-[4-[3-(benzylcarbamoyloxy)phenyl]-3-fluoro-phenyl]propanoate. The crude was purified by preparative HPLC to afford the title compound as a white solid (69 mg, 35%). ¹H NMR (400 MHz, DMSO-d₆) δ 12.47 (s, 1H), 8.36 (t, J=6.1, 1H), 7.49 (m, 2H), 7.36 (m, 5H), 7.25 (m, 4H), 7.17 (dd, J=7.8, 1.7, 1H), 4.29 (d, J=6.1, 2H), 3.78 (q, J=7.1, 1H), 1.41 (d, J=7.1, 3H). ¹³C NMR (101 MHz, DMSO-d₆) δ 174.7, 158.7 (d, J=246.3 Hz), 154.5, 151.1, 143.4 (d, J=7.6 Hz), 139.1, 135.9, 130.6, 129.4, 128.3, 127.1, 126.9, 125.7 (d, J=12.9 Hz), 125.3, 124.0, 121.8, 121.22, 115.1 (d, J=23.2 Hz), 44.0, 44.0, 18.2. MS (ES) C₂₃H₂₀FNO₄ requires 393, found 394 [M+H]⁺.

Compound 27

Methyl 2-[3-fluoro-4-[3-(phenethylcarbamoyloxy)phenyl]phenyl]

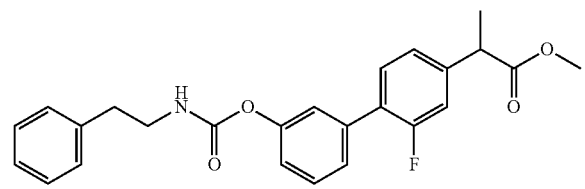 [SMILES: COC(=O)C(C)c1ccc(-c2cccc(OC(=O)NCCc3ccccc3)c2)c(F)c1]

The title compound was prepared according to general method B using methyl 2-[3-fluoro-4-(3-hydroxyphenyl)phenyl]propanoate (137 mg, 0.5 mmol) and phenylethylisocyanate (221 mg, 1.5 mmol). The crude was purified by column chromatography (Cy/EtOAc, 9:1) to afford the title compound as a white solid (165 mg, 71%). ¹H NMR (400 MHz, CDCl₃) δ 7.32 (m, 9H), 7.13 (m, 3H), 5.12 (t, J=5.6 Hz, 1H), 3.76 (q, J=7.2 Hz, 1H), 3.70 (s, 3H), 3.55 (q, J=6.8 Hz, 2H), 2.90 (t, J=7.0 Hz, 2H), 1.54 (d, J=7.2 Hz, 3H). MS (ES) C₂₅H₂₄FNO₄ requires 421, found 422 [M+H]⁺.

Compound 28 (Example 7)

2-[3-fluoro-4-[3-(phenethylcarbamoyloxy)phenyl]phenyl]propanoic acid

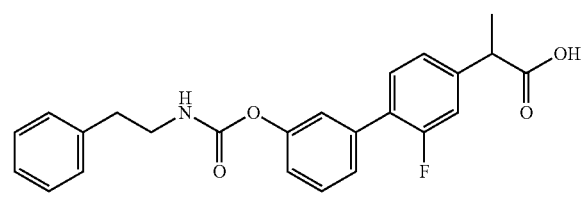 [SMILES: CC(C(=O)O)c1ccc(-c2cccc(OC(=O)NCCc3ccccc3)c2)c(F)c1]

The title compound was prepared according to general method D using methyl 2-[3-fluoro-4-[3-(phenethylcarbamoyloxy)phenyl]phenyl]propanoate. The crude was purified by crystallization from Et₂O/pentane to afford the title compound as a white solid (58 mg, 41%). ¹H NMR (400 MHz, DMSO-d₆) δ 12.45 (s, 1H), 7.88 (t, J=5.6 Hz, 1H), 7.48 (m, 2H), 7.37 (d, J=7.6 Hz, 1H), 7.26 (m, 8H), 7.11 (dd, J=7.7, 1.7 Hz, 1H), 3.78 (q, J=7.1 Hz, 1H), 3.31 (m, 2H), 2.80 (t, J=7.4 Hz, 2H), 1.41 (d, J=7.1 Hz, 3H). ¹³C NMR (101 MHz, DMSO-d₆) δ 175.2, 159.2 (d, J=245.8 Hz), 154.6, 151, 143.9 (d, J=7.7 Hz), 139.5, 136.4, 131.1 (d, J=3.4 Hz), 129.9, 129.1, 128.8, 126.6, 126.2 (d, J=13.0 Hz), 125.7, 124.5 (d, J=2.8 Hz), 122.3 (d, J=2.6 Hz), 121.6, 115.6 (d, J=23.1 Hz), 44.5, 42.5, 35.6, 18.7. MS (ES) C₂₄H₂₂FNO₄ requires 407, found 408 [M+H]⁺.

Compound 29

Methyl 2-[3-fluoro-4-[3-(3-phenylpropylcarbamoyloxyl)phenyl]phenyl]-propanoate

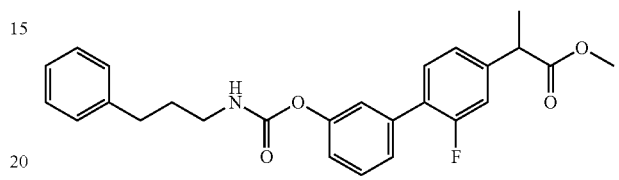

The title compound was prepared according to general method B using methyl 2-[3-fluoro-4-(3-hydroxyphenyl)phenyl]propanoate (137 mg, 0.5 mmol) and phenylpropylisocyanate (241 mg, 1.5 mmol). The crude was purified by column chromatography (Cy/EtOAc, 9:1) to afford the title compound as a white solid (174 mg, 79%). ¹H NMR (400 MHz, CDCl₃) δ 7.39 (m, 3H), 7.30 (m, 3H), 7.21 (m, 3H), 7.13 (m, 3H), 5.11 (t, J=5.5 Hz, 1H), 3.76 (q, J=7.2 Hz, 1H), 3.70 (s, 3H), 3.31 (q, J=6.8 Hz, 2H), 2.71 (t, J=7.7 Hz, 2H), 1.92 (p, J=7.3 Hz, 2H), 1.54 (d, J=7.2 Hz, 3H). MS (ES) C₂₆H₂₆FNO₄ requires 435, found 436 [M+H]⁺.

Compound 30 (Example 8)

2-[3-fluoro-4-[3-(3-phenylpropylcarbamoyloxyl)phenyl]phenyl]propanoic acid

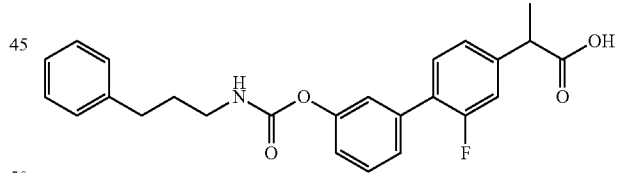

The title compound was prepared according to general method D using methyl 2-[3-fluoro-4-[3-(3-phenylpropylcarbamoyloxyl)phenyl]phenyl]propanoate (174 mg, 0.40 mmol). The crude was purified by preparative TLC (Cy:EtOAc, 5:5) to afford the title compound as a white solid (44 mg, 26%). ¹H NMR (400 MHz, DMSO-d₆) δ 12.47 (s, 1H), 7.85 (s, 1H), 7.48 (m, 2H), 7.38 (d, J=7.2 Hz, 1H), 7.22 (m, 9H), 3.78 (q, J=6.5 Hz, 1H), 3.09 (q, J=6.3 Hz, 2H), 2.63 (t, J=7.3 Hz, 2H), 1.78 (p, J=6.7 Hz, 2H), 1.41 (d, J=6.9 Hz, 3H). ¹³C NMR (101 MHz, DMSO-d₆) δ 175.2, 159.2 (d, J=246.1 Hz), 154.7, 151.6, 143.9 (d, J=8.1 Hz), 142.0, 136.4, 131.1, 129.9, 128.7, 128.7, 126.2, 125.7 (d, J=3.5 Hz), 124.5 (d, J=3.4 Hz), 122.3, 121.70, 115.6 (d, J=23.5 Hz), 44.5, 40.5, 32.8, 31.4, 18.7. MS (ES) C₂₅H₂₄FNO₄ requires 421, found 422 [M+H]⁺.

Compound 31

Methyl 2-[3-fluoro-4-[3-(4-phenylbutylcarbamoyloxyl)phenyl]phenyl]propanoate

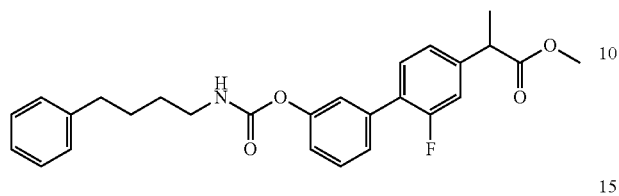

The title compound was prepared according to general method B using methyl 2-[3-fluoro-4-(3-hydroxyphenyl)phenyl]propanoate (121 mg, 0.44 mmol) and phenylpropyllisocyanate (231 mg, 1.32 mmol). The crude was purified by column chromatography (Cy/EtOAc, 8:2) to afford the title compound as a white solid (171 mg, 86%). $^1$H NMR (400 MHz, CDCl$_3$) δ 7.38 (m, 3H), 7.27 (m, 3H), 7.19 (m, 3H), 7.12 (m, 3H), 5.02 (t, J=4.9 Hz, 1H), 3.76 (q, J=7.2 Hz, 1H), 3.70 (s, 3H), 3.30 (q, J=6.7 Hz, 2H), 2.67 (t, J=7.4 Hz, 2H), 1.71 (m, 2H), 1.63 (m, 2H), 1.54 (s, 3H). MS (ES) C$_{27}$H$_{28}$FNO$_4$ requires 449, found 450 [M+H]$^+$.

Compound 32 (Example 9)

2-[3-fluoro-4-[3-(4-phenylbutylcarbamoyloxyl)phenyl]phenyl]propanoic acid

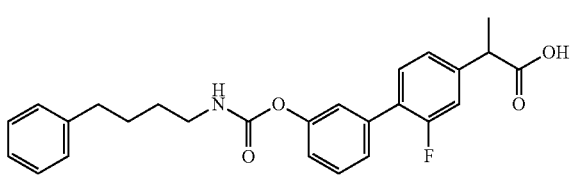 [SMILES: CC(C(=O)O)c1ccc(-c2cccc(OC(=O)NCCCCc3ccccc3)c2)c(F)c1]

The title compound was prepared according to general method D using methyl 2-[3-fluoro-4-[3-(4-phenylbutylcarbamoyloxyl)phenyl]phenyl]propanoate (171 mg, 0.38 mmol). The crude was purified by preparative TLC (Cy:EtOAc, 5:5) to afford the title compound as a white solid (70 mg, 43%). $^1$H NMR (400 MHz, DMSO-d$_6$) δ 12.47 (s, 1H), 7.80 (t, J=5.7 Hz, 1H), 7.47 (m, 2H), 7.37 (d, J=7.3 Hz, 1H), 7.19 (m, 9H), 3.78 (q, J=7.1 Hz, 1H), 3.10 (q, J=6.6 Hz, 2H), 2.60 (t, J=7.5 Hz, 2H), 1.60 (q, J=7.9 Hz, 2H), 1.50 (q, J=7.2 Hz, 2H), 1.41 (d, J=7.1 Hz, 3H). $^{13}$C NMR (101 MHz, DMSO-d$_6$) δ 175.2, 159.2 (d, J=246.3 Hz), 154.7, 151.6, 143.9 (d, J=7.5 Hz), 142.5, 136.4, 131.0 (d, J=3.6 Hz), 129.9, 128.7, 128.6, 126.2 (d, J=13.1 Hz), 126.1, 125.7 (d, J=2.4 Hz), 124.5 (d, J=3.3 Hz), 122.3 (d, J=3.1 Hz), 121.6, 115.6 (d, J=23.2 Hz), 44.5, 40.7, 35.2, 29.3, 28.7, 18.74. MS (ES) C$_{26}$H$_{26}$FNO$_4$ requires 435, found 436 [M+H]$^+$.

Compound 33

Methyl 2-[4-[3-(ethylcarbamoyloxy)phenyl]-3-fluoro-phenyl]propanoate

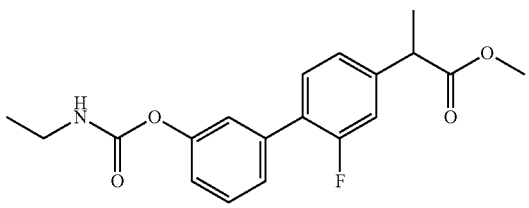 [SMILES: CCNC(=O)Oc1cccc(-c2ccc(C(C)C(=O)OC)cc2F)c1]

The title compound was prepared according to general method B using methyl 2-[3-fluoro-4-(3-hydroxyphenyl)phenyl]propanoate (185 mg, 0.68 mmol) and ethylisocyanate (145 mg, 2.04 mmol). The crude was purified by column chromatography (Cy/EtOAc, 8:2) to afford the title compound as a white solid (176 mg, 75%). $^1$H NMR (400 MHz, CDCl$_3$) δ 7.39 (m, 3H), 7.31 (s, 1H), 7.12 (m, 3H), 5.09 (s, 1H), 3.75 (q, J=7.2 Hz, 1H), 3.70 (s, 3H), 3.31 (p, J=7.1 Hz, 2H), 1.53 (d, J=7.2 Hz, 3H), 1.21 (t, J=7.2 Hz, 3H). MS (ES) C$_{19}$H$_{20}$FNO$_4$ requires 345, found 346 [M+H]$^+$.

Compound 34

2-[4-[3-(ethylcarbamoyloxy)phenyl]-3-fluoro-phenyl]propanoic acid

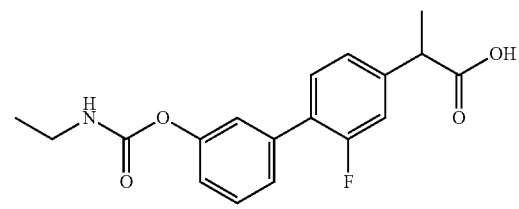 [SMILES: CCNC(=O)Oc1cccc(-c2ccc(C(C)C(=O)O)cc2F)c1]

The title compound was prepared according to general method D using methyl 2-[4-[3-(ethylcarbamoyloxy)phenyl]-3-fluoro-phenyl]propanoate (104 mg, 0.30 mmol). The crude was purified by crystallization from Et$_2$O/pentane to afford the title compound as a white solid (37 mg, 37%). $^1$H NMR (400 MHz, DMSO-d$_6$) δ 12.48 (s, 1H), 7.79 (t, J=5.5 Hz, 1H), 7.51 (t, J=8.3 Hz, 1H), 7.48 (t, J=7.9 Hz, 1H), 7.39 (d, J=7.5 Hz, 1H), 7.25 (m, 3H), 7.15 (d, J=7.9 Hz, 1H), 3.79 (q, J=7.1 Hz, 1H), 3.12 (p, J=7.1 Hz, 2H), 1.42 (d, J=7.1 Hz, 3H), 1.10 (t, J=7.2 Hz, 3H). $^{13}$C NMR (101 MHz, DMSO-d$_6$) δ 175.3, 159.2 (d, J=245.9 Hz), 154.5, 151.6, 143.9 (d, J=7.6 Hz), 136.4, 131.1 (d, J=3.6 Hz), 129.9, 126.2 (d, J=13.0 Hz), 125.7, 124.5 (d, J=3.0 Hz), 122.3 (d, J=3.1 Hz), 121.7, 115.6 (d, J=23.4 Hz), 44.5, 35.7, 18.7, 15.3. MS (ES) C$_{18}$H$_{18}$FNO$_4$ requires 331, found 332 [M+H]$^+$.

Compound 35

Methyl 2-[3-fluoro-4-[3-(propylcarbamoyloxy)phenyl]phenyl]propanoate

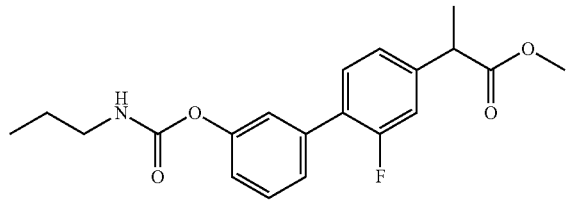 [SMILES: CCCNC(=O)Oc1cccc(-c2ccc(C(C)C(=O)OC)cc2F)c1]

The title compound was prepared according to general method B using methyl 2-[3-fluoro-4-(3-hydroxyphenyl)phenyl]propanoate (137 mg, 0.50 mmol) and n-propylisocyanate (128 mg, 1.5 mmol). The crude was purified by column chromatography (Cy/EtOAc, 9:1) to afford the title compound as a white solid (87 mg, 48%). $^1$H NMR (400 MHz, CDCl$_3$) δ 7.39 (m, 3H), 7.31 (m, 1H), 7.12 (m, 3H), 5.04 (t, J=5.6 Hz, 1H), 3.75 (q, J=7.2 Hz, 1H), 3.70 (s, 3H), 3.25 (q, J=6.8 Hz, 2H), 1.61 (h, J=7.3 Hz, 2H), 1.53 (d, J=7.2 Hz, 3H), 0.98 (t, J=7.4 Hz, 3H). MS (ES) C$_{20}$H$_{22}$FNO$_4$ requires 359, found 360 [M+H]$^+$

Compound 36

2-[3-fluoro-4-[3-(propylcarbamoyloxy)phenyl]phenyl]propanoic acid

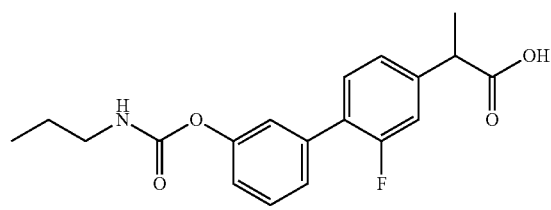 [SMILES: CCCNC(=O)Oc1cccc(-c2ccc(C(C)C(=O)O)cc2F)c1]

The title compound was prepared according to general method D using methyl 2-[3-fluoro-4-[3-(propylcarbamoyloxy)phenyl]phenyl]propanoate (87 mg, 0.24 mmol). The crude was purified by preparative TLC (Cy/EtOAc, 5:5) to afford the title compound as a white solid (57 mg, 68%). $^1$H NMR (400 MHz, DMSO-d$_6$) δ 12.47 (s, 1H), 7.79 (t, J=5.7 Hz, 1H), 7.50 (t, J=8.3 Hz, 1H), 7.47 (t, J=7.9 Hz, 1H), 7.37 (d, J=6.9 Hz, 1H), 7.24 (ddt, J=9.9, 3.9, 1.7 Hz, 3H), 7.14 (ddd, J=8.2, 2.4, 1.1 Hz, 1H), 3.78 (q, J=7.1 Hz, 1H), 3.03 (td, J=7.1, 5.9 Hz, 2H), 1.49 (h, J=7.3 Hz, 2H), 1.41 (d, J=7.2 Hz, 3H), 0.89 (t, J=7.4 Hz, 3H). $^{13}$C NMR (101 MHz, DMSO-d$_6$) δ 174.7, 158.7 (d, J=246.5 Hz), 154.2, 151.2, 143.4 (d, J=7.8 Hz), 135.9, 130.6, 129.4, 125.7 (d, J=12.9 Hz), 125.1, 124.0, 121.8, 121.1, 115.1 (d, J=23.2 Hz), 44.0, 42.2, 22.4, 18.2, 11.2. MS (ES) C$_{19}$H$_{20}$FNO$_4$ requires 345, found 346 [M+H]$^+$.

Compound 37

Methyl 2-[4-[3-(butylcarbamoyloxy)phenyl]-3-fluoro-phenyl]propanoate

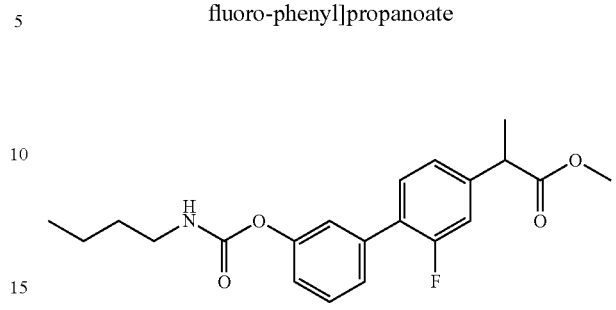

The title compound was prepared according to general method B using methyl 2-[3-fluoro-4-(3-hydroxyphenyl)phenyl]propanoate (137 mg, 0.50 mmol) and n-butylisocyanate (149 mg, 1.5 mmol). The crude was purified by column chromatography (Cy/EtOAc, 9:1) to afford the title compound as a white solid (135 mg, 61%). $^1$H NMR (400 MHz, CDCl$_3$) δ 7.39 (p, J=7.4, 1H), 7.30 (s, OH), 7.12 (t, J=8.9, 1H), 5.04 (s, OH), 3.75 (q, J=7.2, OH), 3.70 (s, 1H), 3.28 (q, J=6.7, 1H), 1.58 (m, 1H), 1.53 (d, J=7.2, 1H), 1.40 (dq, J=14.4, 7.1, 1H), 0.96 (t, J=7.3, 1H). MS (ES) C$_{21}$H$_{24}$FNO$_4$ requires 373, found 374 [M+H]$^+$.

Compound 38 (Example 10)

2-[4-[3-(butylcarbamoyloxy)phenyl]-3-fluoro-phenyl]propanoic acid

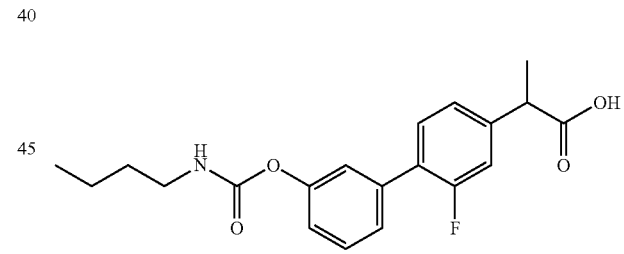

The title compound was prepared according to general method D using methyl 2-[4-[3-(butylcarbamoyloxy)phenyl]-3-fluoro-phenyl]propanoate (135 mg, 0.36 mmol). The crude was purified by crystallization from Cy/Et$_2$O to afford the title compound as a white solid (75 mg, 58%). $^1$H NMR (400 MHz, DMSO-d$_6$) δ 12.48 (s, 1H), 7.79 (t, J=5.7 Hz, 1H), 7.50 (t, J=8.3 Hz, 1H), 7.47 (t, J=7.9 Hz, 1H), 7.37 (d, J=7.0 Hz, 1H), 7.23 (m, 3H), 7.13 (ddd, J=8.1, 2.4, 1.0 Hz, 1H), 3.78 (q, J=7.1 Hz, 1H), 3.06 (q, J=6.8 Hz, 2H), 1.46 (p, J=6.9 Hz, 2H), 1.40 (d, J=7.2 Hz, 3H), 1.32 (h, J=7.1 Hz, 2H), 0.89 (t, J=7.3 Hz, 3H). $^{13}$C NMR (101 MHz, DMSO-d$_6$) δ 174.8, 158.8 (d, J=246.0 Hz), 154.2, 151.2, 143.4 (d, J=8.0 Hz), 135.9, 130.6 (d, J=2.9 Hz), 129.4, 125.7 (d, J=12.8 Hz), 125.2, 124.0, 121.8, 121.2, 115.2 (d, J=23.3 Hz), 44.1, 40.1, 31.3, 19.4, 18.2, 13.6. MS (ES) C$_{20}$H$_{22}$FNO$_4$ requires 359, found 360 [M+H]$^+$.

Compound 39

Methyl 2-[3-fluoro-4-[3-(pentylcarbamoyloxy)phenyl]phenyl]propanoate

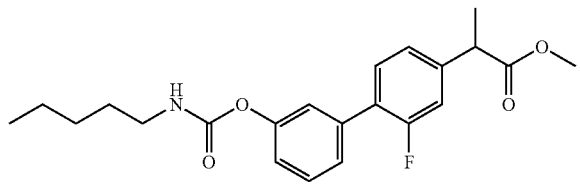 [SMILES: CCCCCNC(=O)Oc1cccc(-c2ccc(C(C)C(=O)OC)cc2F)c1]

The title compound was prepared according to general method B using methyl 2-[3-fluoro-4-(3-hydroxyphenyl)phenyl]propanoate (128 mg, 0.47 mmol) and n-pentylisocyanate (159 mg, 1.41 mmol). The crude was purified by column chromatography (Cy/EtOAc, 9:1) to afford the title compound as a white solid (158 mg, 87%). $^1$H NMR (400 MHz, CDCl$_3$) δ 7.39 (m, 3H), 7.30 (q, J=1.5 Hz, 1H), 7.12 (m, 3H), 5.02 (t, J=5.2 Hz, 1H), 3.75 (q, J=7.2 Hz, 1H), 3.70 (s, 3H), 3.27 (q, J=6.8 Hz, 2H), 1.58 (m, 2H), 1.53 (d, J=7.2 Hz, 3H), 1.36 (m, 4H), 0.92 (t, J=6.9 Hz, 3H). MS (ES) C$_{22}$H$_{26}$FNO$_4$ requires 387, found 388 [M+H]$^+$.

Compound 40 (Example 11)

2-[3-fluoro-4-[3-(pentylcarbamoyloxy)phenyl]phenyl]propanoic acid

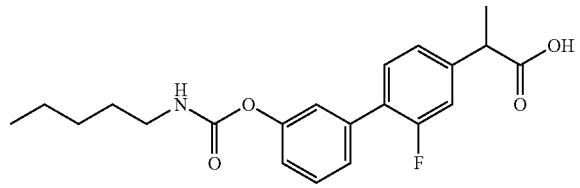 [SMILES: CCCCCNC(=O)Oc1cccc(-c2ccc(C(C)C(=O)O)cc2F)c1]

The title compound was prepared according to general method D using methyl 2-[3-fluoro-4-[3-(pentylcarbamoyloxy)phenyl]phenyl]propanoate (149 mg, 0.39 mmol). The crude was purified by crystallization from pentane/Et$_2$O to afford the title compound as a white solid (85 mg, 59%). $^1$H NMR (400 MHz, DMSO-d$_6$) δ 12.40 (s, 1H), 7.77 (t, J=5.7 Hz, 1H), 7.48 (m, 2H), 7.37 (d, J=8.6 Hz, 1H), 7.23 (m, 3H), 7.14 (dd, J=8.1, 2.2 Hz, 1H), 3.78 (q, J=7.1 Hz, 1H), 3.06 (q, J=6.8 Hz, 2H), 1.48 (p, J=7.2 Hz, 2H), 1.41 (d, J=7.2 Hz, 3H), 1.29 (m, 4H), 0.88 (t, J=6.9 Hz, 3H). $^{13}$C NMR (101 MHz, DMSO-d$_6$) δ 175.2, 159.2 (d, J=246.4 Hz), 154.6, 151.7, 143.9 (d, J=7.6 Hz), 136.4, 131.1 (d, J=3.6 Hz), 129.9, 126.2 (d, J=13.2 Hz), 125.6, 124.5 (d, J=3.3 Hz), 122.3, 121.6, 115.6 (d, J=23.4 Hz), 44.5, 40.9, 29.3, 28.9, 22.2, 18.7, 14.38. MS (ES) C$_{21}$H$_{24}$FNO$_4$ requires 373, found 374 [M+H]$^+$.

Compound 41

Methyl 2-[3-fluoro-4-[3-(hexylcarbamoyloxy)phenyl]phenyl]propanoate

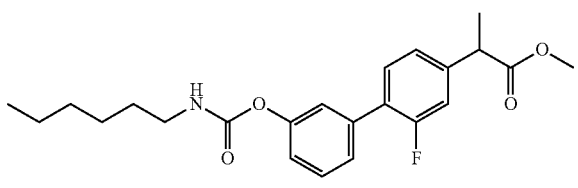 [SMILES: CCCCCCNC(=O)Oc1cccc(-c2ccc(C(C)C(=O)OC)cc2F)c1]

The title compound was prepared according to general method B using methyl 2-[3-fluoro-4-(3-hydroxyphenyl)phenyl]propanoate (137 mg, 0.5 mmol) and n hexylisocyanate (191 mg, 1.5 mmol). The crude was purified by column chromatography (Cy/EtOAc, 9:1) to afford the title compound as a white solid (170 mg, 85%). $^1$H NMR (400 MHz, DMSO-d6) δ 7.77 (t, J=5.6 Hz, 1H), 7.50 (t, J=8.2 Hz, 1H), 7.47 (t, J=7.9 Hz, 1H), 7.37 (d, J=7.2 Hz, 1H), 7.24 (m, 3H), 7.13 (dd, J=8.0, 1.4 Hz, 1H), 3.91 (q, J=7.1 Hz, 1H), 3.62 (s, 3H), 3.06 (q, J=6.7 Hz, 2H), 1.48 (m, 2H), 1.43 (d, J=7.2 Hz, 3H), 1.28 (m, 6H), 0.87 (t, J=6.9 Hz, 3H). MS (ES) C$_{23}$H$_{28}$FNO$_4$ requires: 401, found 402 [M+H]$^+$.

Compound 42 (Example 12)

2-[3-fluoro-4-[3-(hexylcarbamoyloxy)phenyl]phenyl]propanoic acid

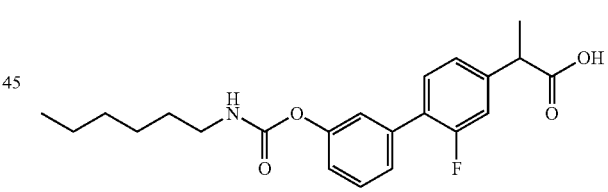

The title compound was prepared according to general method D using methyl 2-[3-fluoro-4-[3-(hexylcarbamoyloxy)phenyl]phenyl]propanoate (142 mg, 0.35 mmol). The crude was purified by crystallization from Et$_2$O/pentane to afford the title compound as a white solid (41 mg, 30%) $^1$H NMR (400 MHz, DMSO-d$_6$) δ 12.29 (s, 1H), 7.79 (t, J=5.7 Hz, 1H), 7.51 (t, J=8.1 Hz, 1H), 7.48 (t, J=7.9 Hz, 1H), 7.39 (d, J=7.7 Hz, 1H), 7.25 (m, 3H), 7.15 (dd, J=8.7, 1.5 Hz, 1H), 3.79 (q, J=7.1 Hz, 1H), 3.07 (q, J=6.8 Hz, 2H), 1.47 (m, 2H), 1.42 (d, J=7.1 Hz, 3H), 1.30 (m, 6H), 0.88 (t, J=7.0 Hz, 3H). $^{13}$C NMR (101 MHz, DMSO-d$_6$) δ 175.2, 159.2 (d, J=246.4 Hz), 154.6, 151.7, 143.9 (d, J=8.0 Hz), 136.4, 131.0, 129.9, 126.2 (d, J=13.1 Hz), 125.6, 124.5 (d, J=3.0 Hz), 122.3 (d, J=2.6 Hz), 121.6, 115.6 (d, J=23.2 Hz), 44.5, 40.9, 31.4, 29.6, 26.3, 22.5, 18.7, 14.3. MS (ES) C$_{22}$H$_{26}$FNO$_4$ requires 387, found 388 [M+H]$^+$.

Compound 43

Methyl 2-[3-fluoro-4-[3-(heptylcarbamoyloxy)phenyl]phenyl]propanoate

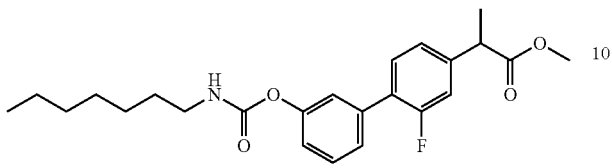

The title compound was prepared according to general method B using methyl 2-[3-fluoro-4-(3-hydroxyphenyl)phenyl]propanoate (137 mg, 0.50 mmol) and n-heptylisocyanate (212 mg, 1.5 mmol). The crude was purified by column chromatography (Cy/EtOAc, 9:1) to afford the title compound as a white solid (171 mg, 82%). $^1$H NMR (400 MHz, CDCl$_3$) δ 7.39 (m, 3H), 7.30 (q, J=1.7 Hz, 1H), 7.12 (m, 3H), 5.01 (t, J=5.0 Hz, 1H), 3.75 (q, J=7.2 Hz, 1H), 3.70 (s, 3H), 3.27 (q, J=6.8 Hz, 2H), 1.57 (m, 2H), 1.53 (d, J=7.2 Hz, 3H), 1.33 (m, 8H), 0.89 (t, J=6.9 Hz, 3H). MS (ES) C$_{24}$H$_{30}$FNO$_4$ requires 415, found 416 [M+H]$^+$.

Compound 44 (Example 13)

2-[3-fluoro-4-[3-(heptylcarbamoyloxy)phenyl]phenyl]propanoic acid

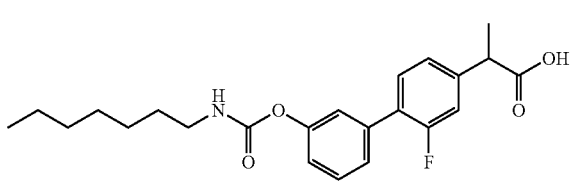 [SMILES: CCCCCCCNC(=O)Oc1cccc(-c2ccc(C(C)C(=O)O)cc2F)c1]

The title compound was prepared according to general method D using methyl 2-[3-fluoro-4-[3-(heptylcarbamoyloxy)phenyl]phenyl]propanoate (160 mg, 0.38 mmol). The crude was purified by crystallization from pentane/Et$_2$O to afford the title compound as a white solid (85 mg, 55%). $^1$H NMR (400 MHz, DMSO-d$_6$) δ 12.47 (s, 1H), 7.77 (t, J=5.7 Hz, 1H), 7.48 (m, 2H), 7.37 (d, J=7.7 Hz, 1H), 7.24 (m, 3H), 7.13 (dd, J=8.0, 2.2 Hz, 1H), 3.78 (q, J=7.1 Hz, 1H), 3.06 (q, J=6.8 Hz, 2H), 1.47 (m, 2H), 1.41 (d, J=7.1 Hz, 3H), 1.27 (m, 8H), 0.86 (t, J=6.8 Hz, 3H). $^{13}$C NMR (101 MHz, DMSO-d$_6$) δ 174.7, 158.7 (d, J=246.5 Hz), 154.1, 151.2, 143.4 (d, J=7.6 Hz), 135.9, 130.6 (d, J=3.6 Hz), 129.4, 125.7 (d, J=13.1 Hz), 125.2, 124.0 (d, J=3.2 Hz), 121.8, 121.1, 115.1 (d, J=23.3 Hz), 44.0, 40.4, 31.2, 29.1, 28.3, 26.1, 22.0, 18.2, 13.9 MS (ES) C$_{23}$H$_{28}$FNO$_4$ requires 401, found 402 [M+H]$^+$.

Compound 45

Methyl 2-[3-fluoro-4-[3-(octylcarbamoyloxy)phenyl]phenyl]propanoate

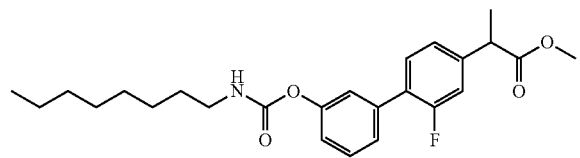 [SMILES: CCCCCCCCNC(=O)Oc1cccc(-c2ccc(C(C)C(=O)OC)cc2F)c1]

The title compound was prepared according to general method B using methyl 2-[3-fluoro-4-(3-hydroxyphenyl)phenyl]propanoate (109 mg, 0.40 mmol) and n-octylisocyanate (186 mg, 1.2 mmol). The crude was purified by column chromatography (Cy/EtOAc, 9:1) to afford the title compound as a white solid (171 mg, 99%). $^1$H NMR (400 MHz, CDCl$_3$) δ 7.39 (p, J=7.4 Hz, 3H), 7.30 (s, 1H), 7.12 (m, 3H), 5.08 (t, J=4.9 Hz, 1H), 3.75 (q, J=7.2 Hz, 1H), 3.70 (s, 3H), 3.26 (q, J=6.8 Hz, 2H), 1.57 (m, 2H), 1.53 (d, J=7.2 Hz, 3H), 1.30 (m, 10H), 0.88 (t, J=6.8 Hz, 3H). MS (ES) C$_{25}$H$_{32}$FNO$_4$ requires 429, found 430 [M+H]$^+$.

Compound 46 (Example 14)

2-[3-fluoro-4-[3-(octylcarbamoyloxy)phenyl]phenyl]propanoic acid

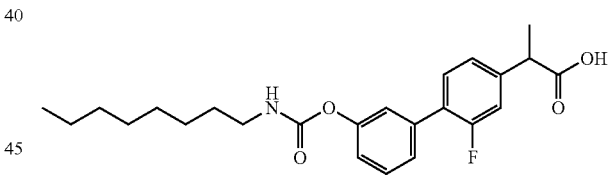

The title compound was prepared according to general method D using methyl 2-[3-fluoro-4-[3-(octylcarbamoyloxy)phenyl]phenyl]propanoate (141 mg, 0.33 mmol). The crude was purified by crystallization from pentane/Et$_2$O to afford the title compound as a white solid (41 mg, 30%). $^1$H NMR (400 MHz, DMSO-d$_6$) δ 12.49 (s, 1H), 7.78 (t, J=5.6 Hz, 1H), 7.50 (m, 2H), 7.39 (d, J=7.3 Hz, 1H), 7.25 (m, 3H), 7.15 (d, J=7.9 Hz, 1H), 3.79 (q, J=7.1 Hz, 1H), 3.07 (q, J=6.7 Hz, 2H), 1.48 (m, 2H), 1.42 (d, J=7.1 Hz, 3H), 1.28 (d, J=6.2 Hz, 10H), 0.87 (t, J=6.6 Hz, 3H). $^{13}$C NMR (101 MHz, DMSO-d$_6$) δ 175.2, 159.2 (d, J=246.4 Hz), 154.6, 151.7, 143.9 (d, J=8.0 Hz), 136.4, 131.0 (d, J=3.6 Hz), 129.9, 126.23 (d, J=13.1 Hz), 125.6 (d, J=2.8 Hz), 124.5 (d, J=3.1 Hz), 122.3, 121.6, 115.6 (d, J=23.3 Hz), 44.5, 40.9, 31.7, 29.6, 29.1, 29.1, 26.7, 22.5, 18.7, 14.4. MS (ES) C$_{24}$H$_{30}$FNO$_4$ requires 415, found 416 [M+H]$^+$.

Compound 47

3-[2-fluoro-4-(2-hydroxy-1-methyl-ethyl)phenyl]phenol

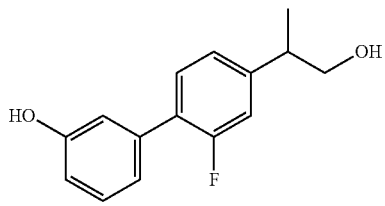 [SMILES: CC(CO)c1ccc(-c2cccc(O)c2)c(F)c1]

To a solution of ZrCl$_4$ (291 mg, 1.25 mmol) in THF (5 mL), NaBH$_4$ (189 mg, 5 mmol) was added at room temperature. Upon mixing the reagents, gas evolution is immediately observed and a cream colored suspension was obtained. A solution of methyl 2-[3-fluoro-4-(3-hydroxyphenyl)phenyl]propanoate (274 mg, 1 mmol) in THF (1 mL) was added and the mixture was stirred at room temperature for 2 h. The reaction was carefully quenched by the addition of 2M HCl (5 mL) and then extracted with EtOAc. The solvent was removed under reduced pressure and the residue was purified by column chromatography (Cy/EtOAc, 7:3) to afford the title compound as a white solid (235 mg, 96%). $^1$H NMR (400 MHz, CDCl$_3$) δ 7.37 (t, J=8.0 Hz, 1H), 7.30 (t, J=7.9 Hz, 1H), 7.09 (m, 2H), 7.04 (dd, J=11.8, 1.7 Hz, 1H), 7.01 (dt, J=2.9, 1.6 Hz, 1H), 6.83 (ddd, J=8.1, 2.6, 1.0 Hz, 1H), 3.75 (m, 2H), 3.00 (h, J=6.9 Hz, 1H), 1.30 (d, J=7.0 Hz, 3H). $^{13}$C NMR (101 MHz, CDCl$_3$) δ 159.9 (d, J=245.0 Hz), 155.7, 145.7 (d, J=7.5 Hz), 137.3, 130.8 (d, J=4.0 Hz), 129.8, 126.9 (d, J=12.3 Hz), 123.6, 121.5, 116.0, 115.1 (d, J=23.1 Hz), 114.7, 68.5, 42.1, 17.6. MS (ES) C$_{15}$H$_{15}$FO$_2$ requires 246, found 245 [M−H]$^-$.

Compound 48 (Example 15)

[3-[2-fluoro-4-(2-hydroxy-1-methyl-ethyl)phenyl]phenyl]N-hexylcarbamate

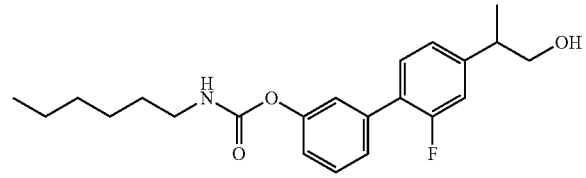 [SMILES: CCCCCCNC(=O)Oc1cccc(-c2ccc(C(C)CO)cc2F)c1]

The title compound was prepared according to general method B using 3-[2-fluoro-4-(2-hydroxy-1-methyl-ethyl)phenyl]phenol (123 mg, 0.50 mmol) and n-hexylisocyanate (127 mg, 1 mmol). The crude was purified by column chromatography (Cy/EtOAc, 9:1) to afford the title compound as a colorless oil (137 mg, 73%). $^1$H NMR (400 MHz, DMSO-d$_6$) δ 7.77 (t, J=5.7 Hz, 1H), 7.45 (m, 2H), 7.36 (m, 1H), 7.23 (m, 1H), 7.17 (m, 2H), 7.12 (ddd, J=8.1, 2.3, 1.1 Hz, 1H), 4.69 (t, J=5.2 Hz, 1H), 3.51 (m, 2H), 3.06 (q, J=6.8 Hz, OH), 2.87 (h, J=6.8 Hz, 1H), 1.46 (m, 2H), 1.29 (m, 7H), 1.21 (d, J=7.0 Hz, 3H), 0.87 (t, J=6.7 Hz, 3H). $^{13}$C NMR (101 MHz, DMSO-d$_6$) δ 158.8 (d, J=246.0 Hz), 154.1, 151.1, 147.7 (d, J=7.3 Hz), 136.2, 130.1, 129.3, 125.1, 124.8 (d, J=12.7 Hz), 124.0, 121.7, 120.9, 114.9 (d, J=22.4 Hz), 66.5, 41.4, 40.4, 30.9, 29.1, 25.8, 22.0, 17.7, 13.8. MS (ES) C$_{22}$H$_{28}$FNO$_3$ requires 373, found 374[M+H]$^+$.

Compound 49

Methyl 2-(3-fluoro-4-hydroxy-phenyl)acetate

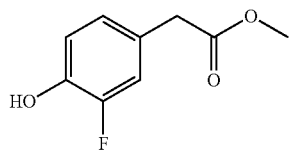

To a solution of 2-(3-fluoro-4-hydroxy-phenyl)acetic acid (1 g, 5.88 mmol) in MeOH (17 mL), concentrated H$_2$SO$_4$ (0.1 mL) was added and the resulting solution was stirred overnight at room temperature. After solvent evaporation, the crude oil was diluted with Et$_2$O (15 mL) and filtered through a plug of SiO$_2$ to afford the title compound as a yellow liquid (1.08 g, quant.). $^1$H NMR (400 MHz, CDCl$_3$) δ 7.03 (m, 1H), 6.92 (m, 2H), 5.25 (s, 1H), 3.70 (s, 3H), 3.54 (s, 2H). MS (ES) C$_9$H$_9$FO$_3$ requires 184, found 183 [M−H]$^-$.

Compound 50

Methyl 2-[3-fluoro-4-(trifluoromethylsulfonyloxy)phenyl]acetate

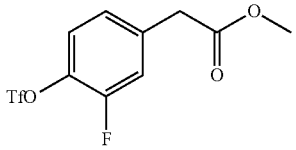

To a solution of methyl 2-(3-fluoro-4-hydroxy-phenyl)acetate (1.08 g, 5.88 mmol) in DCM (24 mL) trifluoromethanesulphonic anhydride (1.48 ml, 8.82 mmol) was added dropwise at 0° C. under stirring over a period of 5 min under nitrogen atmosphere followed by the addition of Et$_3$N (2.46 mL, 17.64 mmol) over a period of 5 min. The resulting solution was stirred at room temperature for 1 h. The reaction mixture was then diluted with DCM (20 mL), and washed sequentially with H$_2$O (20 mL), saturated aqueous NaHCO$_3$ solution (20 mL), and H$_2$O (20 mL). The organic layer was dried by passing through a phase separating cartridge and evaporated under reduced pressure. The crude product was purified by column chromatography (0 to 20% EtOAc in Cy) to give the title compound as a yellow oil (1.86 g, quant.). $^1$H NMR (400 MHz, CDCl$_3$) δ 7.29 (dd, J=8.4, 7.6 Hz, 1H), 7.24 (dd, J=10.4, 2.1 Hz, 1H), 7.13 (dt, J=8.5, 1.6 Hz, 1H), 3.73 (s, 3H), 3.65 (s, 2H). MS (ES) C$_{10}$H$_8$F$_4$O$_5$S requires 316, found 315 [M−H]$^-$.

Compound 51

Methyl 2-[3-fluoro-4-(3-hydroxyphenyl)phenyl]acetate

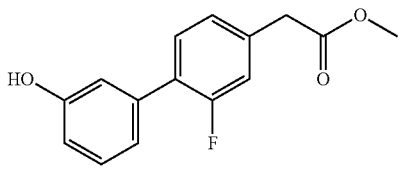 [SMILES: COC(=O)Cc1ccc(-c2cccc(O)c2)c(F)c1]

The title compound was prepared according to general method A using methyl 2-[3-fluoro-4-(trifluoromethylsulfonyloxy)phenyl]acetate (1.86 g, 5.88 mmol) and 3-hydroxyphenylboronic acid (0.97 g, 7.06 mmol). The crude was purified by column chromatography (Cy/EtOAc, 9:1) to afford the title compound as colorless oil (350 mg, purity 81% as measured by UPLC/MS analysis). MS (ES) $C_{15}H_{13}FO_3$ requires 260, found 259 [M–H]$^-$.

Compound 52

Methyl 2-[3-fluoro-4-[3-(hexylcarbamoyloxy)phenyl]phenyl]acetate

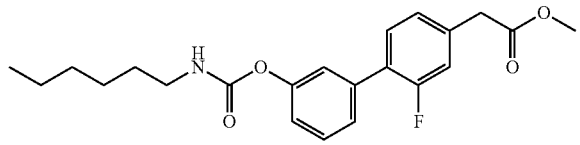 [SMILES: CCCCCCNC(=O)Oc1cccc(-c2ccc(CC(=O)OC)cc2F)c1]

The title compound was prepared according to general method B using methyl 2-[3-fluoro-4-(3-hydroxyphenyl)phenyl]acetate (130 mg, 0.50 mmol) and n-hexylisocyanate (191 mg, 1.5 mmol). The crude was purified by column chromatography (Cy/EtOAc, 9:1) to afford the title compound as a white solid (123 mg, 64%). $^1$H NMR (400 MHz, CDCl$_3$) δ 7.41 (m, 1H), 7.31 (m, OH), 7.12 (m, 1H), 5.03 (t, J=5.3 Hz, OH), 3.73 (s, 1H), 3.65 (s, 1H), 3.27 (q, J=6.9 Hz, 1H), 1.58 (m, 1H), 1.34 (m, 2H), 0.90 (t, J=6.7 Hz, 1H). MS (ES) $C_{22}H_{26}FNO_4$ requires 387, found 388 [M+H]$^+$.

Compound 53 (Example 16)

2-[3-fluoro-4-[3-(hexylcarbamoyloxy)phenyl]phenyl]acetic acid

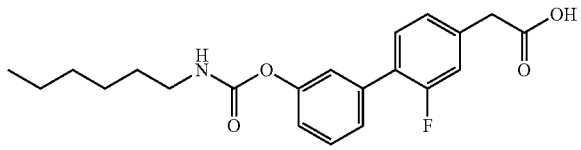 [SMILES: CCCCCCNC(=O)Oc1cccc(-c2ccc(CC(=O)O)cc2F)c1]

The title compound was prepared according to general method D using methyl 2-[3-fluoro-4-[3-(hexylcarbamoyloxy)phenyl]phenyl]acetate (123 mg, 0.32 mmol). The crude was purified by crystallization from pentane/Et$_2$O to afford the title compound as a white solid (73 mg, 62%). $^1$H NMR (400 MHz, DMSO-d$_6$) δ 12.44 (s, 1H), 7.77 (t, J=5.7 Hz, 1H), 7.48 (t, J=8.1 Hz, 1H), 7.47 (t, J=8.0 Hz, 1H), 7.37 (dq, J=7.8, 1.5 Hz, 1H), 7.23 (m, 2H), 7.20 (dd, J=7.9, 1.7 Hz, 1H), 7.13 (ddd, J=8.1, 2.4, 1.0 Hz, 1H), 3.66 (s, 2H), 3.06 (td, J=7.1, 5.8 Hz, 2H), 1.47 (p, J=7.1 Hz, 2H), 1.29 (m, 6H), 0.87 (t, J=7.0 Hz, 3H). $^{13}$C NMR (101 MHz, DMSO-d$_6$) δ 172.1, 158.6 (d, J=245.9 Hz), 154.2, 151.2, 137.2 (d, J=8.4 Hz), 136.0, 130.3 (d, J=3.5 Hz), 129.4, 126.0 (d, J=3.1 Hz), 125.5 (d, J=13.2 Hz), 125.2, 121.8, 121.1, 117.1 (d, J=23.2 Hz), 40.4, 39.8, 30.9, 29.1, 25.89, 22.0, 13.8. MS (ES) $C_{21}H_{24}FNO_4$ requires 373, found 374 [M+H]$^+$.

Compound 54

Methyl 2-[3-fluoro-4-[2-(hexylcarbamoyloxy)phenyl]phenyl]propanoate

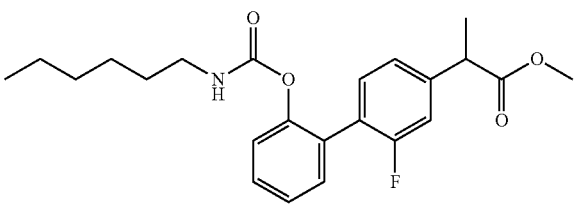 [SMILES: CCCCCCNC(=O)Oc1ccccc1-c1ccc(C(C)C(=O)OC)cc1F]

The title compound was prepared according to general method B using methyl 2-[3-fluoro-4-(2-hydroxyphenyl)phenyl]propanoate (137 mg, 0.5 mmol) and n-hexylisocyanate (191 mg, 1.5 mmol). The crude was purified by column chromatography (Cy/EtOAc, 9:1) to afford the title compound as a white oil (178 mg, 88%). $^1$H NMR (400 MHz, CDCl$_3$) δ 7.39 (td, J=7.7, 1.9 Hz, 1H), 7.34 (d, J=6.3 Hz, 1H), 7.27 (m, 3H), 7.10 (m, 2H), 4.84 (t, J=5.3 Hz, 1H), 3.76 (q, J=7.2 Hz, 1H), 3.70 (s, 3H), 3.14 (q, J=6.7 Hz, 2H), 1.53 (d, J=7.2 Hz, 3H), 1.43 (m, 2H), 1.27 (m, 6H), 0.89 (t, J=6.8 Hz, 3H). MS (ES) $C_{23}H_{28}FNO_4$ requires 401, found 402 [M+H]$^+$.

Compound 55 (Example 17)

2-[3-fluoro-4-[2-(hexylcarbamoyloxy)phenyl]phenyl]propanoic acid

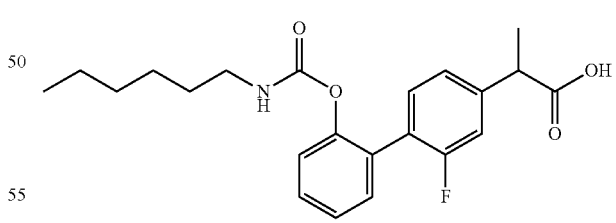

The title compound was prepared according to general method D using methyl 2-[3-fluoro-4-[2-(hexylcarbamoyloxy)phenyl]phenyl]propanoate (200 mg, 0.5 mmol). The crude was purified by preparative TLC (Cy/EtOAc, 5:5) to afford the title compound as a white oil (175 mg, 90%). $^1$H NMR (400 MHz, DMSO-d$_6$) δ 12.47 (s, 1H), 7.55 (t, J=5.7 Hz, 1H), 7.42 (td, J=7.6, 1.9 Hz, 1H), 7.36 (dd, J=7.7, 1.9 Hz, 1H), 7.28 (m, 2H), 7.17 (m, 3H), 3.76 (q, J=7.1 Hz, 1H), 2.92 (q, J=6.6 Hz, 2H), 1.40 (d, J=7.1 Hz, 3H), 1.25 (m, 8H), 0.86 (t, J=6.8 Hz, 3H). $^{13}$C NMR (101 MHz, DMSO-d$_6$) δ

174.8, 158.9 (d, J=246.2 Hz), 154.0, 148.5, 143.2 (d, J=7.5 Hz), 131.3, 131.0, 128.9, 128.1, 125.0, 123.3, 123.3, 123.1, 114.5 (d, J=22.9 Hz), 44.1, 40.2, 30.8, 28.9, 25.6, 22.0, 18.3, 13.8. MS (ES) $C_{22}H_{26}FNO_4$ requires 387, found 388 $[M+H]^+$.

Compound 56

Methyl 2-[3-fluoro-4-[3-(hexoxycarbonylamino)phenyl]phenyl]propanoate

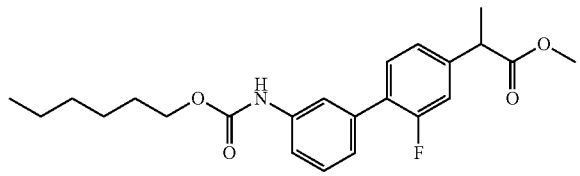 [SMILES: CCCCCCOC(=O)Nc1cccc(-c2ccc(C(C)C(=O)OC)cc2F)c1]

The title compound was prepared according to general method C using methyl 2-[4-(3-aminophenyl)-3-fluoro-phenyl]propanoate (114 mg, 0.44 mmol) and n-hexanol (224 mg, 2.20 mmol). The crude was purified by column chromatography (Cy/EtOAc, 9:1) to obtain the title compound as a white solid (145 mg, 82%). $^1$H NMR (400 MHz, CDCl$_3$) δ 7.56 (s, 1H), 7.37 (m, 3H), 7.22 (dd, J=7.4, 1.2 Hz, 1H), 7.12 (m, 2H), 6.78 (s, 1H), 4.17 (t, J=6.7 Hz, 2H), 3.75 (q, J=7.2 Hz, 1H), 3.70 (s, 3H), 1.67 (m, 2H), 1.53 (d, J=7.2 Hz, 3H), 1.34 (m, 6H), 0.90 (t, J=6.9 Hz, 3H). MS (ES) $C_{23}H_{28}FNO_4$ requires 401, found 402 $[M+H]^+$.

Compound 57 (Example 18)

2-[3-fluoro-4-[3-(hexoxycarbonylamino)phenyl]phenyl]propanoic acid

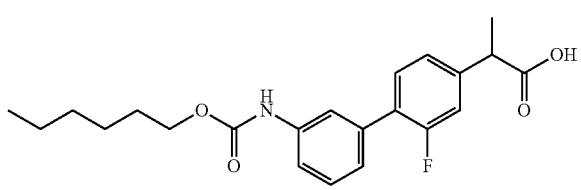 [SMILES: CCCCCCOC(=O)Nc1cccc(-c2ccc(C(C)C(=O)O)cc2F)c1]

The title compound was prepared according to general method D using methyl 2-[3-fluoro-4-[3-(hexoxycarbonylamino)phenyl]phenyl]propanoate (143 mg, 0.36 mmol). The crude was purified by preparative TLC (Cy/EtOAc, 5:5) to afford the title compound as a white solid (82 mg, 59%). $^1$H NMR (400 MHz, DMSO-d$_6$) δ 12.46 (s, 1H), 9.70 (s, 1H), 7.66 (s, 1H), 7.49 (d, J=8.3 Hz, 1H), 7.42 (t, J=8.3 Hz, 1H), 7.36 (t, J=7.9 Hz, 1H), 7.23 (m, 1H), 7.21 (s, 1H), 7.14 (d, J=6.8 Hz, 1H), 4.08 (t, J=6.6 Hz, 2H), 3.77 (q, J=7.1 Hz, 1H), 1.62 (p, J=6.7 Hz, 2H), 1.40 (d, J=7.1 Hz, 3H), 1.30 (m, 6H), 0.87 (t, J=6.9 Hz, 3H). $^{13}$C NMR (101 MHz, DMSO-d$_6$) δ 175.3, 159.2 (d, J=246.1 Hz), 154.1, 143.6 (d, J=8.0 Hz), 139.9, 135.8, 130.9 (d, J=3.7 Hz), 129.44, 127.0 (d, J=13.2 Hz), 124.4 (d, J=3.1 Hz), 123.1, 118.9, 118.0, 115.6 (d, J=23.4 Hz), 64.7, 44.5, 31.3, 28.9, 25.5, 22.5, 18.7, 14.3. MS (ES) $C_{22}H_{26}FNO_4$ requires 387, found 388 $[M+H]^+$.

From the detailed description and examples provided above, the advantages achieved by means of the compounds of the present invention are evident. In particular, said compounds have proven to be surprisingly and advantageously able to act as single-target or multiple-target inhibitors of FAAH and COXs.

Compound 58 (Example 19)

(−)-2-[3-fluoro-4-[3-(hexylcarbamoyloxy)phenyl]phenyl]propanoic acid, (−)-Example 12: $[α]^D_{20}$=−29±1.6 (c=0.1, CHCl$_3$). ee % (detector UV 247.5 nm)≥99%. $^1$H NMR (400 MHz, DMSO-d$_6$) δ 12.29 (s, 1H), 7.79 (t, J=5.7 Hz, 1H), 7.51 (t, J=8.1 Hz, 1H), 7.48 (t, J=7.9 Hz, 1H), 7.39 (d, J=7.7 Hz, 1H), 7.25 (m, 3H), 7.15 (dd, J=8.7, 1.5 Hz, 1H), 3.79 (q, J=7.1 Hz, 1H), 3.07 (q, J=6.8 Hz, 2H), 1.47 (m, 2H), 1.42 (d, J=7.1 Hz, 3H), 1.30 (m, 6H), 0.88 (t, J=7.0 Hz, 3H). $^{13}$C NMR (101 MHz, DMSO-d6) δ 175.2, 159.2 (d, J=246.4 Hz), 154.6, 151.7, 143.9 (d, J=8.0 Hz), 136.4, 131.0, 129.9, 126.2 (d, J=13.1 Hz), 125.6, 124.5 (d, J=3.0 Hz), 122.3 (d, J=2.6 Hz), 121.6, 115.6 (d, J=23.2 Hz), 44.5, 40.9, 31.4, 29.6, 26.3, 22.5, 18.7, 14.3. MS (ES) $C_{22}H_{26}FNO_4$ requires 387, found 388 $[M+H]^+$. Rt on analytical chiral HPLC, 15.90 min and Rt on preparative chiral HPLC, 19.67 min.

Compound 59 (Example 20)

(+)-2-[3-fluoro-4-[3-(hexylcarbamoyloxy)phenyl]phenyl]propanoic acid, (+)-Example 12: $[α]^D_{20}$=+27±2.2 (c=0.1, CHCl$_3$). ee % (detector UV 247.5 nm)≥99%. $^1$H NMR (400 MHz, DMSO-d$_6$) δ 12.29 (s, 1H), 7.79 (t, J=5.7 Hz, 1H), 7.51 (t, J=8.1 Hz, 1H), 7.48 (t, J=7.9 Hz, 1H), 7.39 (d, J=7.7 Hz, 1H), 7.25 (m, 3H), 7.15 (dd, J=8.7, 1.5 Hz, 1H), 3.79 (q, J=7.1 Hz, 1H), 3.07 (q, J=6.8 Hz, 2H), 1.47 (m, 2H), 1.42 (d, J=7.1 Hz, 3H), 1.30 (m, 6H), 0.88 (t, J=7.0 Hz, 3H). $^{13}$C NMR (101 MHz, DMSO-d$_6$) δ 175.2, 159.2 (d, J=246.4 Hz), 154.6, 151.7, 143.9 (d, J=8.0 Hz), 136.4, 131.0, 129.9, 126.2 (d, J=13.1 Hz), 125.6, 124.5 (d, J=3.0 Hz), 122.3 (d, J=2.6 Hz), 121.6, 115.6 (d, J=23.2 Hz), 44.5, 40.9, 31.4, 29.6, 26.3, 22.5, 18.7, 14.3. MS (ES) $C_{22}H_{26}FNO_4$ requires 387, found 388 $[M+H]^+$. Rt on analytical chiral HPLC, 26.80 min and Rt on preparative chiral HPLC, 34.08 min.

What is claimed is:
1. A compound that simultaneously inhibits the enzymes Fatty Acid Amide Hydrolase (FAAH), Cyclooxygenase-1 (COX-1) and/or Cyclooxygenase-2 (COX-2) having the formula (Ia)

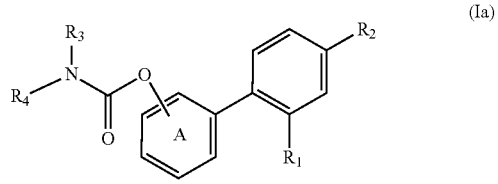

or pharmaceutically acceptable salts thereof,
wherein
the phenyl ring A is substituted in the meta or ortho position with the carbamoyl group,
$R_1$ is halogen,
$R_2$ is a group —CHR$_5$—(C═O)—R$_6$
wherein R$_5$ is (C$_1$-C$_6$)_alkyl, and R$_6$ is —OH, and R$_3$ and R$_4$ are independently selected from a group consisting of H, $(C_1-C_{10})$ alkyl, $(C_3-C_9)$ cycloalkyl $(C_0-C_4)$ alkyl, phenyl $(C_0-C_4)$ alkyl, phenyl and $(C_3-C_9)$ cycloalkyl.

2. A compound according to claim 1, wherein $R_1$ is F and $R_2$ is
   a group —$CHR_5$—(C=O)—$R_6$, wherein $R_5$ is $(C_1-C_6)$ alkyl, and $R_6$ is —OH.

3. A compound according to claim 1, wherein $R_3$ and $R_4$ are independently selected from a group consisting of $(C_1-C_{10})$ alkyl, $(C_3-C_9)$ cycloalkyl $(C_0-C_4)$ alkyl, and phenyl $(C_0-C_4)$ alkyl.

4. A compound according to claim 1, wherein
   $R_3$ is H, and
   $R_4$ is $(C_1-C_{10})$ alkyl, $(C_3-C_9)$ cycloalkyl $(C_0-C_4)$ alkyl, or phenyl $(C_0-C_4)$ alkyl.

5. A compound according to claim 1, wherein
   $R_1$ is F; $R_2$ is —$CHR_5$—(C=O)—$R_6$ wherein $R_5$ is $CH_3$, $R_6$ is OH,
   $R_3$ is H, and
   $R_4$ is $(C_1-C_{10})$ alkyl, $(C_3-C_9)$ cycloalkyl $(C_0-C_4)$ alkyl, or phenyl $(C_0-C_4)$ alkyl.

6. A pharmaceutical composition comprising a compound of formula (Ia) or a pharmaceutically acceptable salt thereof of claim 1 and a pharmaceutical acceptable carrier and/or excipient.

* * * * *